(12) United States Patent
Makale et al.

(10) Patent No.: US 10,864,272 B2
(45) Date of Patent: Dec. 15, 2020

(54) SCINTILLATOR NANOCRYSTAL-CONTAINING COMPOSITIONS AND METHODS FOR THEIR USE

(71) Applicant: The Regents of the University of California, Oakland, CA (US)

(72) Inventors: Milan T. Makale, San Diego, CA (US); Wolfgang J. Wrasidlo, La Jolla, CA (US); Santosh Kesari, La Jolla, CA (US); Joanna McKittrick, La Jolla, CA (US); Gustavo A. Hirata Flores, Ensenada (MX); Olivia Graeve, La Mesa, CA (US)

(73) Assignee: The Regents of the University of California, Oakland, CA (US)

( * ) Notice: Subject to any disclaimer, the term of this patent is extended or adjusted under 35 U.S.C. 154(b) by 333 days.

(21) Appl. No.: 15/052,526

(22) Filed: Feb. 24, 2016

(65) Prior Publication Data
US 2016/0250330 A1 Sep. 1, 2016

Related U.S. Application Data

(63) Continuation of application No. PCT/US2014/053487, filed on Aug. 29, 2014.

(60) Provisional application No. 61/872,122, filed on Aug. 30, 2013.

(51) Int. Cl.
| | | |
|---|---|---|
| *A61K 41/00* | (2020.01) | |
| *A61K 47/69* | (2017.01) | |
| *A61K 31/704* | (2006.01) | |
| *A61N 5/06* | (2006.01) | |
| *A61N 5/10* | (2006.01) | |

(52) U.S. Cl.
CPC ........ *A61K 41/0042* (2013.01); *A61K 31/704* (2013.01); *A61K 47/6923* (2017.08); *A61K 47/6929* (2017.08); *A61N 5/06* (2013.01); *A61N 5/10* (2013.01); *A61N 2005/0661* (2013.01); *A61N 2005/1098* (2013.01)

(58) Field of Classification Search
None
See application file for complete search history.

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,212,162 A | 5/1993 | Missel et al. |

(Continued)

FOREIGN PATENT DOCUMENTS

| | | | |
|---|---|---|---|
| WO | WO-96/05309 A2 | 2/1996 | |
| WO | WO-96/05309 A3 | 2/1996 | |
| WO | WO-2013049521 A2 * | 4/2013 | ............. A61K 47/54 |

OTHER PUBLICATIONS

Wang et al., Theranostics (Mar. 25, 2013), vol. 3, No. 5, pp. 317-330. (Year: 2013).*

(Continued)

*Primary Examiner* — Aradhana Sasan
(74) *Attorney, Agent, or Firm* — Mintz, Levin, Cohn, Ferris, Glovsky and Popeo, P.C.

(57) ABSTRACT

There are provided, inter alia, compositions including a scintillator nanocrystal linked to a chemical agent moiety through a scintillator-activated photocleavable linker, and methods of use thereof.

21 Claims, 22 Drawing Sheets

(56) References Cited

U.S. PATENT DOCUMENTS

| | | | |
|---|---|---|---|
| 5,403,841 A | 4/1995 | Lang et al. | |
| 2004/0178388 A1* | 9/2004 | Mumper | G01T 1/204 252/301.17 |
| 2005/0136439 A1 | 6/2005 | Eaton et al. | |
| 2008/0213151 A1 | 9/2008 | Yoshikawa et al. | |
| 2009/0302225 A1 | 12/2009 | Cherepy et al. | |
| 2010/0048378 A1* | 2/2010 | Tang | B82Y 30/00 501/133 |
| 2013/0171060 A1 | 7/2013 | Vo-Dinh et al. | |

OTHER PUBLICATIONS

Klan et al., Chemical Reviews, vol. 113, pp. 119-191. (Year: 2012).*

Lee, Liposomes as Carriers for Drug Delivery, pp. 1-29. (Year: 2010).*

International Search Report dated Dec. 18, 2014, for PCT Application No. PCT/US2014/053487, filed Aug. 29, 2014, 3 pages.

Written Opinion dated Dec. 18, 2014, for PCT Application No. PCT/US2014/053487, filed Aug. 29, 2014, 4 pages.

Bosze, E.J. et al. (2003). "Investigation of the physical properties of a blue-emitting phosphor produced using a rapid exothermic reaction" *Materials Science and Engineering* B97:265-274.

Bosze, E.J. et al. (2007). "Long-Ultraviolet-Excited White-Light Emission in Rare-Earth-Activated Yttrium-Oxyorthosolicate," *J Am Ceram Soc* 90(8):2484-2488.

Chen, D. et al. (2008). "Sol-Gel Combustion Synthesis of Nanocrystalline YAG Powder from Metal-Organic Precursors," *J Am Ceram Soc* 91(8):2759-2762.

Hess, N.J. et al. (1994). "Syntheis and crystallization of yttrium-aluminium garnet and related compounds," *Journal of Materials Science* 29:1873-1878.

Jayaramaiah, J.R. et al. (2011). "Thermoluminescence studies of solution combustion synthesized $Y^2O^3$:$Nd^{3+}$ nanophosphor," *Materials Chemistry and Physics* 130:175-178.

Jung, J.Y. et al. (2014). "Identification and development of nanoscintillators for biotechnology applications," *Journal of Luminescence* 154:569-577.

Lopez, O.A. et al. (1997). "Fluorescence properties of polycrystalline $Tm^{3+}$-activated $Y_3Al_5O_{12}$ and $Tm^{3+}$-$Li^+$ co-activated $Y_3Al_5O_{12}$ in the visible and near IR ranges," *Journal of Luminescence* 71:1-11.

Milliken, E.D. et al. (2012). "Testing a model-guided approach to the development of new thermoluminescent materials using YAG:Ln produced by solution combustion synthesis," *Journal of Luminescence* 132:2495-2504.

Premkumar, H.B. et al. (Oct. 2012, e-published Apr. 23, 2012). "YAlO3:Cr3+ nanophosphor: synthesis, photoluminescence, EPR, dosimetric studies," *Spectrochim Acta A Mol Biomol Spectrosc* 96:154-162.

Puzyrev, I.S. et al. (2012). "Development of Methods for Preparation of Nd:YAG Nanoparticles," *Glass Physics and Chemistry* 38(4):427-430.

Rodríguez, R.A. et al. (2005). "Thermoluminescence and optically stimulated luminescence properties of nanocrystalline $Er^{3+}$ and $Yb^{3+}$ doped $Y_3Al_5O_{12}$ exposed to β-rays," *Journal of Physics D:Applied Physics* 38:3854-3859.

Rodríguez,-García, C.E. et al. (2008). "Red-emitting $SrIn_2O_4$:$Eu^{3+}$ phosphor powders for applications in solid state white lamps," *Journal of Physics D:Applied Physics* 41:092005.

Yukihara, E.G. et al. (2013). "Systematic development of new thermoluminescence and optically stimulated luminescence materials," *Journal of Luminescence* 133:203-210.

\* cited by examiner

UV light at 365 nm

SCINTILLATOR NANOCRYSTAL-CONTAINING COMPOSITIONS AND METHODS FOR THEIR USE

CROSS-REFERENCES TO RELATED APPLICATIONS

This application is a continuation of International Application PCT/US2014/053487, filed Aug. 29, 2014, which claims the benefit of U.S. Provisional Application No. 61/872,122, filed Aug. 30, 2013, each of which is incorporated herein by reference in its entirety and for all purposes.

BACKGROUND OF THE INVENTION

For decades medical radiation specialists have sought to activate by local radiation beams, a nontoxic, inactive version of a cancer drug, (e.g., a prodrug) selectively at cancers and not body tissues in general. This strategy is attractive because it aims to overwhelm tumor resistance mechanisms by allowing high drug concentrations at tumor foci, while sparing normal tissues and organs from toxicity, and reducing the generally damaging radiation doses needed to control tumor burden. Drug activity focused on areas adjacent to tumors that would destroy the micro metastases that are so challenging to selectively excise or treat would be desirable. Single cell infiltration that significantly diminishes by ablating the active margin of primary and secondary tumors, especially in early disease stages, would also be desirable.

Solutions to these and other issues are provided herein.

BRIEF SUMMARY OF THE INVENTION

There is disclosed herein, inter alia, the novel concept of completely bypassing oxygen quenching by linking a prodrug to a nanocrystal radiation scintillator. See e.g., FIG. 1 and Scheme 1. For example, embodiments are provided herein in which a drug is inactive while linked to the crystal, but in response to radiation the scintillator emits light to break the chemical linker, thereby releasing active drug. Without wishing to be bound by any theory, one rationale underlying this disclosure is that it makes feasible a transformative process for the widespread development of radiation activatable therapeutics. Indeed, embodiments provided herein offer an entirely new pharmacologic approach based on externally controlled, localized drug activation/release. Moreover, embodiments provided herein will work against many localized diseases like localized infections. For example, intravenously injected nanoparticles may concentrate at tumor foci by leaking through typically incomplete tumor vessels, by adhering to tumor microvessels via well-established targeting ligands, and by penetration of the blood brain barrier (BBB) both passively and actively via transferrin ligands. Thousands of drug molecules may be linked to a single 100-150 nm scintillator crystal, and millions of such crystals can be injected. Indeed, 100 nm liposomal nanoparticles can deliver sufficient drug to completely suppress tumor growth in experimental animal models. In embodiments, with the drug molecules bound very closely to the scintillator, radiation-induced drug release can occur with high efficiency.

In a first aspect, there is provided a composition including a scintillator nanocrystal linked to a chemical agent moiety through a scintillator-activated photocleavable linker.

In another aspect, there is provided a method for delivering a chemical agent moiety to a target site. The method includes: (i) providing a composition including a scintillator nanocrystal linked to a chemical agent moiety through scintillator-activated photocleavable linker as disclosed herein to a location at or near a target site and (ii) cleaving the chemical agent from the remainder of the composition by exposing the composition to radiation thereby delivering the chemical agent to the target site. The term "target site" and the like refer, in the usual and customary sense, to a site which can benefit by local administration of the chemical agent moiety. In medical applications, the chemical agent moiety can be a drug moiety, a hormone moiety or a detectable moiety.

In another aspect, there is provided a method of delivering a chemical agent moiety to a subject. The method includes: (i) administering a composition including a scintillator nanocrystal linked to a chemical agent moiety through scintillator-activated photocleavable linker as disclosed herein to the subject, and (ii) cleaving the chemical agent from the remainder of the compound by exposing the composition to radiation thereby delivering the chemical agent to the subject.

BRIEF DESCRIPTION OF THE DRAWINGS

(FIG. 16A) $(Lu_{0.75}Y_{0.2}Pr_{0.05})_2SiO_5$ heated for 2-h; (FIG. 16B) $(Lu_{0.75}Y_{0.2}Pr_{0.05})_2SiO_5$ heated for 4 h.

(FIG. 20A) 0.5 at. %; (FIG. 20B) 1.0 at. %; (FIG. 20C) 1.5 at. %; and (FIG. 20D) 2.0 at. %.

FIG. 24A depicts a histogram showing result after 1 hours of dialysis after irradiation, so only the bound Dox remains; a stepwise response to radiation dose is observed. Legend: for each radiation level (Non-irradiated, 2 gy, 4 gy), the left histogram entry represent Dox absorption in the dialysate, and the right entry is after 1-hr of dialysis. FIG. 24B: After more complete dialysis, 24 hours, it is observed that little bound Dox remains, and there is still a dose response. Legend: for each radiation level (Non-irradiated, 2 gy, 4 gy), the left histogram entry (open rectangle) represent Dox absorption in the dialysate, and the right entry (closed rectangle) is after 24-hr of dialysis.

FIG. 25A: Image of liposomal nanoparticles labeled with BODIPY inside tumor vessels. Liposomes are also permeating from the tumor vessels (arrow). FIGS. 25B-25C: Figures depict in vivo imaging (rodent dorsal skinfold chamber) of disintegration of human M21L melanoma angiogenic vessels at Day 0 (FIG. 25B) and after six days (FIG. 25C) of intravenous liposomal doxorubicin. (tumor is $\alpha v\beta 3$-, vessels are +ve). At Day 0 (FIG. 25B), extended vessels are observed. At Day 6 (FIG. 25C), there are observed loss of tips, vessels which are no longer extended, and loss of tumor mass. Pruning of vessels caused a marked reduction in tumor size.

DETAILED DESCRIPTION

Definitions

Figure 1:
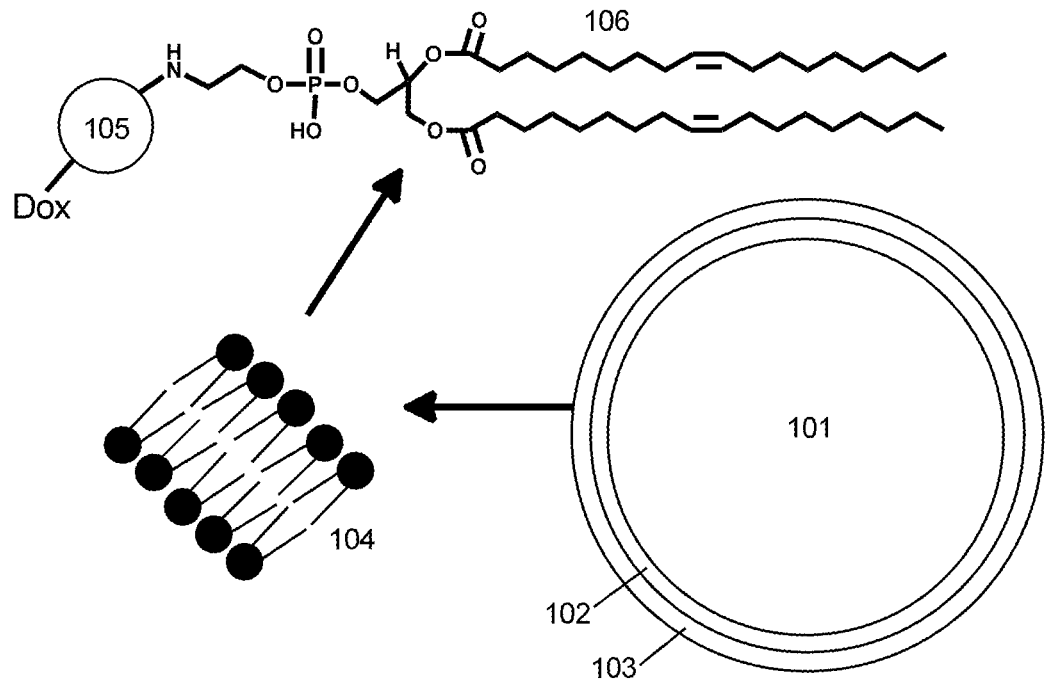
FIG. 1 depicts an exemplary cartoon design scheme for scintillator nanocrystal coated with lipid bilayer and attached to doxorubicin ("Dox" or "Doxil") via a photocleavable linker. The scintillator nanocrystal may be on the order of 100 nm in diameter, and total diameter≈100-150 nm. Legend: 101: scintillator core; 102: inert hydrophilic shell; 103: external lipid bilayer; 104: expanded view of external lipid bilayer, indicated by arrow from 103, and adherent to inert hydrophilic shell; 105: photocleavable linker showing attachment to exemplary lipid bilayer 106 and to chemical agent moiety (e.g., Dox); 106: expanded view of external lipid bilayer, indicated by arrow from 104, e.g., DOPE neutral lipid. Element 106 can be conjugated with chemical agent moiety, e.g., drug (e.g., Dox), polyethylene glycol (PEG), detectable label (e.g., fluorescent label), or other chemical agent moiety disclosed herein. The photocleavable linker can cleave under exposure to UV light (e.g., about 350-360 nm).

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred for the compositions and methods disclosed herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl" by itself or in combination with another term means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substituents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound disclosed herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound disclosed herein includes more than one R group, for example, each of the R groups is independently selected as are each R', R", R''', and R'''' groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF$_3$, —CN, —OH, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CN, —OH, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF$_3$, —CN, —OH, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds described herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the compounds disclosed herein. The compounds disclosed herein do not include those which are known in art to be too unstable to synthesize and/or isolate. The current disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds disclosed herein may exist in tautomeric forms, all such tautomeric forms being within the scope of the compounds disclosed herein.

Unless otherwise stated, structures depicted herein are also meant to include all stereochemical forms of the structure; i.e., the (R) and (S) configurations for each asymmetric center. Therefore, single stereochemical isomers as well as enantiomeric and diastereomeric mixtures of the present compounds, generally recognized as stable by those skilled in the art, are within the scope of the compounds disclosed herein.

Unless otherwise stated, structures depicted herein are also meant to include compounds which differ only in the presence of one or more isotopically enriched atoms. For example, compounds having the present structures except for the replacement of a hydrogen by a deuterium or tritium, replacement of fluoride by $^{18}F$, or the replacement of a carbon by $^{13}C$- or $^{14}C$-enriched carbon are within the scope of the compounds disclosed herein.

The compounds disclosed herein may also contain unnatural proportions of atomic isotopes at one or more of the atoms that constitute such compounds. For example, the compounds may be radiolabeled with radioactive isotopes, such as for example tritium ($^3H$), fluoride ($^{18}F$), iodine-125 ($^{125}I$) or carbon-14 ($^{14}C$). All isotopic variations of the compounds disclosed herein, whether radioactive or not, are encompassed within the scope of the compounds disclosed herein.

The symbol " ∼∼∼ " denotes the point of attachment of a chemical moiety to the remainder of a molecule or chemical formula.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$ etc., wherein each of $R^{13.1}$, $R^{13.2}$, $R^{13.3}$, $R^{13.4}$, etc. is independently defined within the scope of the definition of $R^{13}$ and optionally differently.

Description of compounds disclosed herein is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

"Analog," or "analogue" are used in accordance with plain ordinary meaning within Chemistry and Biology and refer to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analogue is a compound that is similar or comparable in function and appearance but not in structure or origin to a reference compound.

The term "pharmaceutically acceptable salts" is meant to include salts of active compounds that are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds disclosed herein contain both basic and acidic functionalities that allow the compounds to be converted into either base or acid addition salts.

Thus, the compounds disclosed herein may exist as salts, such as with pharmaceutically acceptable acids. The compounds disclosed herein includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, there are provided compounds which are in a prodrug form. Prodrugs of the compounds described herein include those compounds that readily undergo chemical or enzymatic changes under physiological conditions to provide the compounds disclosed herein. Additionally, prodrugs can be converted to the compounds disclosed herein by chemical or biochemical methods in an ex vivo environment. For example, prodrugs can be slowly converted to the compounds disclosed herein when placed in a transdermal patch reservoir with a suitable enzyme or chemical reagent.

Certain compounds disclosed herein can exist in unsolvated forms as well as solvated forms, including hydrated forms. In general, the solvated forms are equivalent to unsolvated forms and are encompassed within the scope disclosed herein. Certain compounds disclosed herein may exist in multiple crystalline or amorphous forms. In general, all physical forms are equivalent for the uses disclosed herein and are intended to be within the scope of the compounds and methods disclosed herein.

As used herein, the term "salt" refers to acid or base salts of the compounds used in the methods disclosed herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refer to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters, including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g., achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the methods disclosed herein should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the measurement of the activity of a protein in the absence of a compound as described herein (including embodiments and examples).

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. Contacting may include allowing a compound described herein to interact with a protein or enzyme that is involved in a signaling pathway.

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. Inhibition may refer to reduction of a disease or symptoms of disease. Inhibition may refer to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions disclosed herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds disclosed herein. One of skill in the art will recognize that other pharmaceutical excipients are useful in the compositions and methods disclosed herein.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions disclosed herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403, 841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions disclosed herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions disclosed herein into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds disclosed herein. Adjustment and manipulation of established dosages (e.g., frequency and duration) are well within the ability of those skilled in the art.

The compounds described herein can be used in combination with one another, with other active drugs known to be useful in treating a disease (e.g., anti-cancer drugs) or with adjunctive agents that may not be effective alone, but may contribute to the efficacy of the active agent. Thus, the compounds described herein may be co-administered with one another or with other active drugs known to be useful in treating a disease.

By "co-administer" it is meant that a compound described herein is administered at the same time, just prior to, or just after the administration of one or more additional therapies, for example, an anticancer agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g., anticancer agents).

Co-administration includes administering one active agent (e.g., a complex described herein) within 0.5, 1, 2, 4, 6, 8, 10, 12, 16, 20, or 24 hours of a second active agent (e.g., anti-cancer agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another. The compounds described herein may be combined with treatments for cancer such as chemotherapy or radiation therapy.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g., toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human. A "cancer-patient" is a patient suffering from, or prone to developing cancer.

"Disease," "disorder" or "condition" refer to a state of being or health status of a patient or subject capable of being treated with the compounds or methods provided herein. Disease as used herein may refer to cancer.

As used herein, the term "cancer" refers to all types of cancer, neoplasm, or malignant or benign tumors found in mammals, including leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The murine leukemia model is widely accepted as being predictive of in vivo anti-leukemic activity. It is believed that a compound that tests positive in the P388 cell assay will generally exhibit some level of anti-leukemic activity regardless of the type of leukemia being treated. Accordingly, the present disclosure includes a method of treating leukemia, including treating acute myeloid leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "sarcoma" generally refers to a tumor which is made up of a substance like the embryonic connective tissue and is generally composed of closely packed cells embedded in a fibrillar or homogeneous substance. Sarcomas which can be treated with a combination of antineoplastic thiol-binding mitochondrial oxidant and an anticancer agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with a combination of antineoplastic thiol-binding mitochondrial oxidant and an anticancer agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with a combination of antineoplastic thiol-binding mitochondrial oxidant and an anticancer agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Anti-cancer agent" is used in accordance with its plain and ordinary meaning and refers to a composition (e.g., compound, drug, antagonist, inhibitor, modulator) having antineoplastic properties or the ability to inhibit the growth or proliferation of cells. In some embodiments, an anti-cancer agent is a chemotherapeutic. An anti-cancer agent may be an agent approved by the FDA or similar regulatory agency of a country other than the USA, for treating cancer.

Examples of anti-cancer agents include, but are not limited to, MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g., U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin, aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g., Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g., Altorhyrtin A and Altorhyrtin C), Spongistatins (e.g., Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g., Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lso-eleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g., gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "nanocrystal" and the like refer, in the usual and customary sense, to a polycrystalline material having a crystallite size less than a micrometer (e.g., 1-10, 1-20, 1-30, 1-40, 1-50, 1-100, 1-200-, 1-500, or even 1-999 nm). The terms "scintillator nanocrystal," "nanocrystal phosphor," "nanophosphor," "nanocrystal radiation scintillator" and the like as used herein refer, in the usual and customary sense, to a nanocrystal which includes a scintillator. The term "scintillator" and the like refer, in the usual and customary sense, to a material that exhibits luminescence when excited by radiation (e.g., ionizing radiation), as known in the art. Thus, a scintillator nanocrystal can robustly scintillate (e.g., by releasing photons) in response to radiation. The scintillator may be energized to release photons by exposure to ionizing radiation including, e.g., X-rays, particle beam radiation, and the like. Scintillator nanocrystals can be held together by covalent or non-covalent forces, as known in the art.

The term "scintillator-activated photocleavable linker" and the like refer, in the usual and customary sense, to a divalent chemical linker which can undergo cleavage upon exposure to light, e.g., light emitted by a scintillator nanocrystal in response to exposure to radiation.

A "detectable moiety" is a composition detectable by spectroscopic, photochemical, biochemical, immunochemical, chemical, magnetic resonance imaging, or other physical means. For example, useful detectable moieties include $^{32}$P, fluorescent dyes, electron-dense reagents, biotin, digoxigenin, paramagnetic molecules, superparamagnetic iron oxide, monocrystalline iron oxide, Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, iodinated contrast agents (e.g., iohexol, iodixanol, ioversol, iopamidol, ioxilan, iopromide, diatrizoate, metrizoate, ioxaglate), barium sulfate, thorium dioxide, gold, fluorophores, two-photon fluorophores, or radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, $^{212}$Bi.

The terms "YAG-Pr" and "YAG-Pr$^{3+}$" refer, in the usual and customary sense, to yttrium aluminum garnet doped with praseodymium (e.g., $Y_3Al_5O_{12}$:Pr).

Absent express indication otherwise, the term "about" in the context of a numeric value refers to the nominal numeric value+/−10% thereof.

I. Compositions

In a first aspect, there is provided a composition including a scintillator nanocrystal linked to a chemical agent moiety through a scintillator-activated photocleavable linker.

Further to any composition disclosed herein, the scintillator nanocrystal can have a diameter (e.g., the longest dimension or the nanocrystal) from about 25 nm to about 300 nm, e.g., about 25-300 nm, about 25-250 nm, about 25-200, about 25-150 nm, about 25-100 nm, about 25-75 nm or about 25-50 nm. The scintillator nanocrystal can have diameter of about 25 nm, 30 nm, 35 nm, 40 nm, 45 nm, 50 nm, 50 nm, 70 nm, 80 nm, 90 nm, 100 nm, 125 nm, 150 nm, 175 nm, 200 nm, 250 nm or 300 nm. The scintillator nanocrystal can have diameter from about 50 nm to about 250 nm, about 50 nm to about 200 nm, about 50 nm or about 150 nm, or about 50 nm to about 100 nm. The longest dimension of the scintillator nanocrystal can be about 1000 nm or less, or about 100 nm or less, or about 10 nm or less. The scintillator nanocrystal can have a longest dimension of about 10-1000 nm, about 10-500 nm, about 10-400 nm, about 10-300 nm, about 10-200 nm, or about 10-100 nm. The longest dimension can be about 5 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 220 nm, 240 nm, 260 nm, 280 nm, 300 nm, 350 nm, 400 nm, 500 nm or even 999 nm.

The term "chemical agent moiety" and the like in the context of compositions and methods disclosed herein refer to a monovalent compound entity attached to the remainder of a composition described herein. In embodiments, the chemical agent moiety can elicit a chemical or biochemical reaction when released from the scintillator nanocrystal through cleavage of the scintillator-activated photocleavable linker. Thus, the methods and compositions disclosed herein may be useful, for example, for controlled delivery of chemical agent moieties via specific temporal and spatial activation. For example, in medical applications, the underlying concept may be to restrict toxic drug effects to tumors and infected tissue by delivering nontoxic, inactive nanoscintillator linked drug selectively to the tumor. A radiation beam (e.g., a low dose radiation beam) can activate the scintillator nanocrystal component, which in turn can emit light to break the scintillator-activated photocleavable linker, resulting in a chemical agent moiety (e.g., drug) being released in an active form at the site of the radiation exposure. Indeed, this can be very localized or include the whole body. The compositions and methods disclosed herein can be useful for tissue engineering, release of hormones or antibiotics, and industrial applications in manufacturing and repair of pipes and coverings with release of multiple components for cements and other agents in a time and location controlled manner in electronics, microfabrication, optics, and related fields.

In embodiments, the chemical agent moiety can be a prodrug. The terms "prodrug," "prodrug moiety" and the like in reference to an embodiment of a compound described herein, refers to a compound that can undergo cleavage from the scintillator nanocrystal to provide a chemical moiety such as a physiologically active agent. Cleavage can be affected by cleavage of a scintillator-activated photocleavage linker, resulting in release of the chemical agent moiety (e.g., a physiologically active agent, such as a drug).

The scintillator nanocrystal can include a plurality of scintillator activators dispersed within a host crystal lattice. The terms "activator" in the context of scintillators, "scintillator activator" and the like refer to a chemical species added (e.g., as a dopant) to a crystal (e.g., a nanocrystal) capable of facilitating luminescence (e.g., in response to radiation). In embodiments, the scintillator activator exhibits a high quantum efficiency when excited by radiation to emit photons. The scintillator activator can be any one or more of Cu, Ag, Eu, Ce, Th, Ce, or Pr. The scintillator activator can be any one or more of Ce, Eu or Pr. The scintillator activator can be Ce, Eu or Pr. The scintillator activators can be Ce or Pr. The scintillator activator can be Ce. The scintillator activators can be Eu. The scintillator activators can be Pr. Typically, the scintillator nanocrystal includes a plurality of scintillator activators. The plurality of scintillator activators may be spaced to minimize concentration quenching. The plurality of scintillator activators may be spaced to maximize the overall photon release, luminescence or scintillation from the scintillator nanocrystal to the scintillator-activated photocleavable linker. In embodiments, where the scintillator activator is Pr, the plurality of Pr scintillator activators may be spaced at approximately the Pr—O bond length.

In embodiments, the plurality of scintillator activators constitute about 1 atomic percent of the scintillator nanocrystal. In embodiments, the plurality of scintillator activators constitute about 2 atomic percent of the scintillator nanocrystal. In embodiments, the plurality of scintillator activators constitute about 3 atomic percent of the scintillator nanocrystal. In embodiments, the plurality of scintillator activators constitute about 4 atomic percent of the scintillator nanocrystal. In embodiments, the plurality of scintillator activators constitute about 5 atomic percent of the scintillator nanocrystal. In embodiments, the plurality of scintillator activators constitute about 6 atomic percent of the scintillator nanocrystal. In embodiments, the plurality of scintillator activators constitute about 7 atomic percent of the scintillator nanocrystal. In embodiments, the plurality of scintillator activators constitute about 8 atomic percent of the scintillator nanocrystal. In embodiments, the plurality of scintillator activators constitute about 9 atomic percent of the scintillator nanocrystal. In embodiments, the plurality of scintillator activators constitute about 10 atomic percent of the scintillator nanocrystal. In embodiments, the plurality of scintillator activators constitute about 1-10 atomic percent of the scintillator nanocrystal. In embodiments, the plurality of scintillator activators constitute about 2-9 atomic percent of the scintillator nanocrystal. In embodiments, the plurality of scintillator activators constitute about 3-8 atomic percent of the scintillator nanocrystal. In embodiments, the plurality of scintillator activators constitute about 4-6 atomic percent of the scintillator nanocrystal.

In embodiments, the host crystal lattice is composed of biocompatible materials (e.g., materials that are biologically inert or do not substantially interfere with organism [e.g., human[biological function). Further to any composition disclosed herein, the host crystal lattice can be a chloride host crystal lattice, bromide host crystal lattice, oxide host crystal lattice, iodide host crystal lattice or silicate host crystal lattice. The term "host crystal lattice" and the like refer, in the usual and customary sense, to a plurality of chemical atoms bound together in an approximate lattice structure comprising a plurality of cavities in which molecules of a second, guest component (e.g., a scintillator activator) can reside. Thus, the guest component can be an activator, e.g., an activator as disclosed herein. A "chloride host crystal lattice" is a host crystal lattice which includes chlorine atoms. A "bromide host crystal lattice" is a host crystal lattice which includes bromine atoms. An "oxide host crystal lattice" is a host crystal lattice which includes oxygen atoms. An "iodide host crystal lattice" is a host crystal lattice which includes iodine atoms. A "silicate host crystal lattice" is a host crystal lattice which includes a silicate, as known in the art. The host crystal lattice can be a lanthium bromide host crystal lattice, as known in the art, which includes lanthanum and bromine. The host crystal lattice can be an oxide host crystal lattice or silicate host crystal lattice. The host crystal lattice can be an oxide host crystal lattice. The host crystal lattice can be a silicate host crystal lattice.

Further to any composition disclosed herein, the host crystal lattice can be a garnet host crystal lattice. The term "garnet host crystal lattice" and the like refer, in the usual and customary sense, to a crystalline compound as known in the art including a transition metal or lanthanoid, e.g., Lu, Yb, Tm, Er, Y, Ho, Dy or Tb. The garnet host crystal lattice can include aluminum. The host crystal lattice can be an yttrium aluminum oxide (YAG, e.g., $Y_3Al_5O_{12}$) host crystal lattice, as known in the art. The host crystal lattice can be a gadolinium/yttrium aluminum oxide host crystal lattice or yttrium gallium/aluminum oxide host crystal lattice, as known in the art. The host crystal lattice can be an gadolinium/yttrium aluminum oxide host crystal lattice. The host crystal lattice can be a yttrium gallium/aluminum oxide host crystal lattice.

The scintillator nanocrystal can have the formula $(Y_{1-x}Pr_x)_3Al_5O_{12}$, wherein x is 0.0075, 0.01, 0.0125, 0.015 or 0.0175.

In embodiments, the scintillator nanocrystal emits a photons after excitation from radiation at a wavelength sufficient to cleave the photocleavable linker without damaging biological structures such as cells, animal organs or animal tissue. Further to any composition disclosed herein, the scintillator nanocrystal can emit a photon with emission peaks within (from) about 300 nm to 470 nm. The scintillator nanocrystal can emit a photon with emission peak within (from) about 350 nm to 470 nm. The scintillator nanocrystal can emit a photon with emission peak within (from) about 350 nm to 400 nm. The scintillator nanocrystal can emit a photon with emission peak within (from) about 350 nm to 370 nm. The scintillator nanocrystal can emit a photon with emission peak within (from) about 350 nm to 360 nm. The scintillator nanocrystal can emit a photon with emission peak within (from) about 100 nm to 600 nm.

Further to any composition disclosed herein, the scintillator-activated photocleavable linker can be covalently attached to the chemical agent moiety and a surface of the scintillator nanocrystal. The surface of the scintillator nanocrystal can be a lipid bilayer surface or a silinated surface. The surface can be a lipid bilayer surface, as known in the art. The surface can be a silinated surface, as known in the art.

Further to any composition disclosed herein, the scintillator-activated photocleavable linker (also referred to herein as the "photocleavable linker") can have the formula:

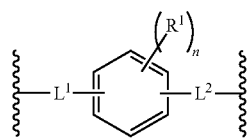
(I)

wherein, $L^1$ and $L^2$ are independently bond, —C(O)—, —C(O)O—, —O—, —S—, —NH—, —C(O)NH—, —NHC(O)—, —S(O)$_2$—, —S(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is independently halogen, —N$_3$, —CF$_3$, —CCl$_3$, —CBr$_3$, —CI$_3$, —CN, —COR$^2$, —OR$^2$, —NR$^2$R$^3$, —C(O)OR$^2$, —C(O)NR$^2$R$^3$, —NO$_2$, —SR$^2$, —S(O)$_{n1}$R$^2$, —S(O)$_{n1}$OR$^2$, —S(O)$_{n1}$NR$^2$R$^3$, —NHNR$^2$R$^3$, —ONR$^2$R$^3$, —NHC(O)NHNR$^2$R$^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^3$ are independently hydrogen, halogen, —N$_3$, —CF$_3$, —CCl$_3$, —CBr$_3$, —CI$_3$, —CN, —COH, —OH, —NH$_2$, —C(O)OH, —C(O)NH$_2$, —NO$_2$, —SH, —S(O)$_{n1}$H, —S(O)$_{n2}$OH, —S(O)$_{n2}$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n is an integer from 0 to 4; n1 and n2 are independently 1 or 2.

$R^1$ can be halogen. $R^1$ can be —N$_3$. $R^1$ can be —CF$_3$. $R^1$ can be —CCl$_3$. $R^1$ can be —CBr$_3$. $R^1$ can be —CI$_3$. $R^1$ can be —CN. $R^1$ can be —COR$^2$. $R^1$ can be —OR$^2$. $R^1$ can be —NR$^2$R$^3$. $R^1$ can be —C(O)OR$^2$. $R^1$ can be —C(O)NR$^2$R$^3$. $R^1$ can be —NO$_2$. $R^1$ can be —SR$^2$. $R^1$ can be —S(O)$_{n1}$R$^2$. $R^1$ can be —S(O)$_{n1}$OR$^2$. $R^1$ can be —S(O)$_{n1}$NR$^2$R$^3$. $R^1$ can be —NHNR$^2$R$^3$. $R^1$ can be —ONR$^2$R$^3$. $R^1$ can be —NHC(O)NHNR$^2$R$^3$. $R^1$ can be substituted or unsubstituted alkyl. $R^1$ can be substituted or unsubstituted heteroalkyl. $R^1$ can be substituted or unsubstituted cycloalkyl. $R^1$ can be substituted or unsubstituted heterocycloalkyl. $R^1$ can be substituted or unsubstituted aryl. $R^1$ can be or substituted or unsubstituted heteroaryl.

In embodiments, $R^1$ is independently halogen, —N$_3$, —CF$_3$, —CCl$_3$, —CBr$_3$, —CI$_3$, —CN, —COR$^2$, —OR$^2$, —NR$^2$R$^3$, —C(O)OR$^2$, —C(O)NR$^2$R$^3$, —NO$_2$, —SR$^2$, —S(O)$_{n1}$R$^2$, —S(O)$_{n1}$OR$^2$, —S(O)$_{n1}$NR$^2$R$^3$, —NHNR$^2$R$^3$, —ONR$^2$R$^3$, —NHC(O)NHNR$^2$R$^3$, $R^{1A}$-substituted or unsubstituted alkyl, $R^{1A}$-substituted or unsubstituted heteroalkyl, $R^{1A}$-substituted or unsubstituted cycloalkyl, $R^{1A}$-substituted or unsubstituted heterocycloalkyl, $R^{1A}$-substituted or unsubstituted aryl, or $R^{1A}$-substituted or unsubstituted heteroaryl. In embodiments, $R^1$ is —NO$_2$. In embodiments, $R^1$ is independently halogen, —N$_3$, —CF$_3$, —CCl$_3$, —CBr$_3$, —CI$_3$, —CN, —COR$^2$, —OR$^2$, —NR$^2$R$^3$, —C(O)OR$^2$, —C(O)NR$^2$R$^3$, —NO$_2$, —SR$^2$, —S(O)$_{n1}$R$^2$, —S(O)$_{n1}$OR$^2$, —S(O)$_{n1}$NR$^2$R$^3$, —NHNR$^2$R$^3$, —ONR$^2$R$^3$, —NHC(O)NHNR$^2$R$^3$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^1$ is independently halogen, —N$_3$, —CF$_3$, —CCl$_3$, —CBr$_3$, —CI$_3$, —CN, —COR$^2$, —OR$^2$, —NR$^2$R$^3$, —C(O)OR$^2$, —C(O)NR$^2$R$^3$, —NO$_2$, —SR$^2$, —S(O)$_{n1}$R$^2$, —S(O)$_{n1}$OR$^2$, —S(O)$_{n1}$NR$^2$R$^3$, —NHNR$^2$R$^3$, —ONR$^2$R$^3$, —NHC(O)NHNR$^2$R$^3$, $R^{1A}$-substituted alkyl, $R^{1A}$-substituted heteroalkyl, $R^{1A}$-substituted cycloalkyl, $R^{1A}$-substituted heterocycloalkyl, $R^{1A}$-substituted aryl, or $R^{1A}$-substituted heteroaryl. $R^{1A}$ is independently halogen, —N$_3$, —CF$_3$, —CCl$_3$, —CBr$_3$, —CI$_3$, —CN, —COR$^2$, —OR$^2$, —NR$^2$R$^3$, —C(O)OR$^2$, —C(O)NR$^2$R$^3$, —NO$_2$, —SR$^2$, —S(O)$_{n1}$R$^2$, —S(O)$_{n1}$OR$^2$, —S(O)$_{n1}$NR$^2$R$^3$, —NHNR$^2$R$^3$, —ONR$^2$R$^3$, —NHC(O)NHNR$^2$R$^3$, $R^{1B}$-substituted or unsubstituted alkyl, $R^{1B}$-substituted or unsubstituted heteroalkyl, $R^{1B}$-substituted or unsubstituted cycloalkyl, $R^{1B}$-substituted or unsubstituted heterocycloalkyl, $R^{1B}$-substituted or unsubstituted aryl, or $R^{1B}$-substituted or unsubstituted heteroaryl. $R^{1B}$ is independently halogen, —N$_3$, —CF$_3$, —CCl$_3$, —CBr$_3$, —CI$_3$, —CN, —COR$^2$, —OR$^2$, —NR$^2$R$^3$, —C(O)OR$^2$, —C(O)NR$^2$R$^3$, —NO$_2$, —SR$^2$, —S(O)$_{n1}$R$^2$, —S(O)$_{n1}$OR$^2$, —S(O)$_{n1}$NR$^2$R$^3$, —NHNR$^2$R$^3$, —ONR$^2$R$^3$, —NHC(O)NHNR$^2$R$^3$, —NHC(O)NHNR$^2$R$^3$, $R^{1C}$-substituted or unsubstituted alkyl, $R^{1C}$-substituted or unsubstituted heteroalkyl, $R^{1C}$-substituted or unsubstituted cycloalkyl, $R^{1C}$-substituted or unsubstituted heterocycloalkyl, $R^{1C}$-substituted or unsubstituted aryl, or $R^{1C}$-substituted or unsubstituted heteroaryl. $R^{1C}$ is independently halogen, —N$_3$, —CF$_3$, —CCl$_3$, —CBr$_3$, —CI$_3$, —CN, —COR$^2$, —OR$^2$, —NR$^2$R$^3$, —C(O)OR$^2$, —C(O)NR$^2$R$^3$, —NO$_2$, —SR$^2$, —S(O)$_{n1}$R$^2$, —S(O)$_{n1}$OR$^2$, —S(O)$_{n1}$NR$^2$R$^3$, —NHNR$^2$R$^3$, —ONR$^2$R$^3$, —NHC(O)NHNR$^2$R$^3$, unsubstituted alkyl, unsubstituted heteroalkyl, unsubstituted cycloalkyl, unsubstituted heterocycloalkyl, unsubstituted aryl, or unsubstituted heteroaryl.

Further to any composition disclosed herein including the structure of Formula (I) and embodiments including, e.g., Formulae (Ia), $L^1$ or $L^2$ can be a bond. $L^1$ or $L^2$ can be —C(O)—. $L^1$ or $L^2$ can be —C(O)O—. $L^1$ or $L^2$ can be —O—. $L^1$ or $L^2$ can be —S—. $L^1$ or $L^2$ can be —NH—. $L^1$ or $L^2$ can be —C(O)NH—. $L^1$ or $L^2$ can be —NHC(O)—. $L^1$ or $L^2$ can be —S(O)$_2$—. $L^1$ or $L^2$ can be —S(O)NH—. $L^1$ or $L^2$ can be substituted or unsubstituted alkylene. $L^1$ or $L^2$ can be substituted or unsubstituted heteroalkylene. $L^1$ or $L^2$ can be substituted or unsubstituted cycloalkylene. $L^1$ or $L^2$ can be substituted or unsubstituted heterocycloalkylene. $L^1$ or $L^2$ can be substituted or unsubstituted arylene. $L^1$ or $L^2$ can be or substituted or unsubstituted heteroarylene.

In embodiments, $L^1$ is a bond, —C(O)—, —C(O)O—, —O—, —S—, —NH—, —C(O)NH—, —NHC(O)—, —S(O)$_2$—, —S(O)NH—, $R^{4A}$-substituted or unsubstituted alkylene, $R^{4A}$-substituted or unsubstituted heteroalkylene, $R^{4A}$-substituted or unsubstituted cycloalkylene, $R^{4A}$-substituted or unsubstituted heterocycloalkylene, $R^{4A}$-substituted or unsubstituted arylene, or $R^{4A}$-substituted or unsubstituted heteroarylene. In embodiments, $L^1$ is unsubstituted alkylene, unsubstituted heteroalkylene, unsubstituted cycloalkylene, unsubstituted heterocycloalkylene, unsubstituted arylene, or unsubstituted heteroarylene. In embodiments, $L^1$ is $R^{4A}$-substituted alkylene, $R^{4A}$-substituted heteroalkylene, $R^{4A}$-substituted cycloalkylene, $R^{4A}$-heterocycloalkylene, $R^{4A}$-substituted arylene, or $R^{4A}$-substituted heteroarylene. $R^{4A}$ is halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{4B}$-substituted or unsubstituted alkyl, $R^{4B}$-substituted or unsubstituted heteroalkyl, $R^{4B}$-substituted or unsubstituted cycloalkyl, $R^{4B}$-substituted or unsubstituted heterocycloalkyl, $R^{4B}$-substituted or unsubstituted aryl, or $R^{4B}$-substituted or unsubstituted heteroaryl. $R^{4B}$ is halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{4C}$-substituted or unsubstituted alkyl, $R^{4C}$-substituted or unsubstituted heteroalkyl, $R^{4C}$-substituted or unsubstituted cycloalkyl, $R^{4C}$-substituted or unsubstituted heterocycloalkyl, $R^{4C}$-substituted or unsubstituted aryl, or $R^{4C}$-substituted or unsubstituted heteroaryl. $R^{4C}$ is halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $L^2$ is a bond, —C(O)—, —C(O)O—, —O—, —S—, —NH—, —C(O)NH—, —NHC(O)—, —$S(O)_2$—, —S(O)NH—, $R^{5A}$-substituted or unsubstituted alkylene, $R^{5A}$-substituted or unsubstituted heteroalkylene, $R^{5A}$-substituted or unsubstituted cycloalkylene, $R^{5A}$-substituted or unsubstituted heterocycloalkylene, $R^{5A}$-substituted or unsubstituted arylene, or $R^{5A}$-substituted or unsubstituted heteroarylene. In embodiments, $L^2$ is unsubstituted alkylene, unsubstituted heteroalkylene, unsubstituted cycloalkylene, unsubstituted heterocycloalkylene, unsubstituted arylene, or unsubstituted heteroarylene. In embodiments, $L^2$ is $R^{5A}$-substituted alkylene, $R^{5A}$-substituted heteroalkylene, $R^{5A}$-substituted cycloalkylene, $R^{5A}$-heterocycloalkylene, $R^{5A}$-substituted arylene, or $R^{5A}$-substituted heteroarylene. $R^{5A}$ is halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{5B}$-substituted or unsubstituted alkyl, $R^{5B}$-substituted or unsubstituted heteroalkyl, $R^{5B}$-substituted or unsubstituted cycloalkyl, $R^{5B}$-substituted or unsubstituted heterocycloalkyl, $R^{5B}$-substituted or unsubstituted aryl, or $R^{5B}$-substituted or unsubstituted heteroaryl. $R^{5B}$ is halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{5C}$-substituted or unsubstituted alkyl, $R^{5C}$-substituted or unsubstituted heteroalkyl, $R^{5C}$-substituted or unsubstituted cycloalkyl, $R^{5C}$-substituted or unsubstituted heterocycloalkyl, $R^{5C}$-substituted or unsubstituted aryl, or $R^{5C}$-substituted or unsubstituted heteroaryl. $R^{5C}$ is halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^2$ or $R^3$ can be hydrogen. $R^2$ or $R^3$ can be halogen. $R^2$ or $R^3$ can be —$N_3$. $R^2$ or $R^3$ can be —$CF_3$. $R^2$ or $R^3$ can be —$CCl_3$. $R^2$ or $R^3$ can be —$CBr_3$. $R^2$ or $R^3$ can be —$CI_3$. $R^2$ or $R^3$ can be —CN. $R^2$ or $R^3$ can be —COH. $R^2$ or $R^3$ can be —OH. $R^2$ or $R^3$ can be —$NH_2$. $R^2$ or $R^3$ can be —C(O)OH. $R^2$ or $R^3$ can be —C(O)$NH_2$. $R^2$ or $R^3$ can be —$NO_2$. $R^2$ or $R^3$ can be —SH. $R^2$ or $R^3$ can be —$S(O)_{n1}H$. $R^2$ or $R^3$ can be —$S(O)_{n2}OH$. $R^2$ or $R^3$ can be —$S(O)_{n2}NH_2$. $R^2$ or $R^3$ can be —$NHNH_2$. $R^2$ or $R^3$ can be —$ONH_2$. $R^2$ or $R^3$ can be —NHC(O)$NHNH_2$. $R^2$ or $R^3$ can be substituted or unsubstituted alkyl. $R^2$ or $R^3$ can be substituted or unsubstituted heteroalkyl. $R^2$ or $R^3$ can be substituted or unsubstituted cycloalkyl. $R^2$ or $R^3$ can be substituted or unsubstituted heterocycloalkyl. $R^2$ or $R^3$ can be substituted or unsubstituted aryl. $R^2$ or $R^3$ can be or substituted or unsubstituted heteroaryl. n can be is an integer from 0 to 4, e.g., 9, 1, 2, 3 or 4. n1 and n2 are independently 1 or 2, e.g., 1 or 2.

In embodiments, $R^2$ is independently hydrogen, halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —$S(O)_{n1}H$, —$S(O)_{n2}OH$, —$S(O)_{n2}NH_2$, —$NHNH_2$, —$ONH_2$, —NHC(O)$NHNH_2$, $R^{2A}$-substituted or unsubstituted alkyl, $R^{2A}$-substituted or unsubstituted heteroalkyl, $R^{2A}$-substituted or unsubstituted cycloalkyl, $R^{2A}$-substituted or unsubstituted heterocycloalkyl, $R^{2A}$-substituted or unsubstituted aryl, or $R^{2A}$-substituted or unsubstituted heteroaryl, wherein n is an integer from 0 to 4. and n1 and n2 are independently 1 or 2. In embodiments, $R^2$ is independently hydrogen, halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —$S(O)_{n1}H$, —$S(O)_{n2}OH$, —$S(O)_{n2}NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl, wherein n is an integer from 0 to 4. and n1 and n2 are independently 1 or 2. In embodiments, $R^2$ is independently hydrogen, halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —$S(O)_{n1}H$, —$S(O)_{n2}OH$, —$S(O)_{n2}NH_2$, —$NHNH_2$, —$ONH_2$, —NHC(O)$NHNH_2$, $R^{2A}$-substituted alkyl, $R^{2A}$-substituted heteroalkyl, $R^{5A}$-substituted cycloalkyl, $R^{2A}$-substituted heterocycloalkyl, $R^{2A}$-substituted aryl, or $R^{2A}$-substituted heteroaryl, wherein n is an integer from 0 to 4. and n1 and n2 are independently 1 or 2. $R^{2A}$ is halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —$S(O)_{n1}H$, —$S(O)_{n2}OH$, —$S(O)_{n2}NH_2$, —$NHNH_2$, —$ONH_2$, —NHC(O)$NHNH_2$, $R^{2B}$-substituted or unsubstituted alkyl, $R^{2B}$-substituted or unsubstituted heteroalkyl, $R^{2B}$-substituted or unsubstituted cycloalkyl, $R^{2B}$-substituted or unsubstituted heterocycloalkyl, $R^{2B}$-substituted or unsubstituted aryl, or $R^{2B}$-substituted or unsubstituted heteroaryl, wherein n is an integer from 0 to 4. and n1 and n2 are independently 1 or 2. $R^{2B}$ is halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —$S(O)_{n1}H$, —$S(O)_{n2}OH$, —$S(O)_{n2}NH_2$, —$NHNH_2$, —$ONH_2$, —NHC(O)$NHNH_2$, $R^{2C}$-substituted or unsubstituted alkyl, $R^{2C}$-substituted or unsubstituted heteroalkyl, $R^{2C}$-substituted or unsubstituted cycloalkyl, $R^{2C}$-substituted or unsubstituted heterocycloalkyl, $R^{2C}$-substituted or unsubstituted aryl, or $R^{2C}$-substituted or unsubstituted heteroaryl, wherein n is an integer from 0 to 4. and n1 and n2 are independently 1 or 2. $R^{2C}$ is halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —S(O)$_{n1}$H, —S(O)$_{n2}$OH, —S(O)$_{n2}$$NH_2$, —NH$NH_2$, —O$NH_2$, —NHC(O)NH$NH_2$, unsubstituted heteroalkyl, unsubstituted cycloalkyl, unsubstituted heterocycloalkyl, unsubstituted aryl, or unsubstituted heteroaryl, wherein n is an integer from 0 to 4. and n1 and n2 are independently 1 or 2.

In embodiments, $R^3$ is independently hydrogen, halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —S(O)$_{n1}$H, —S(O)$_{n2}$OH, —S(O)$_{n2}$$NH_2$, —NH$NH_2$, —O$NH_2$, —NHC(O)NH$NH_2$, $R^{3A}$-substituted or unsubstituted alkyl, $R^{3A}$-substituted or unsubstituted heteroalkyl, $R^{3A}$-substituted or unsubstituted cycloalkyl, $R^{3A}$-substituted or unsubstituted heterocycloalkyl, $R^{3A}$-substituted or unsubstituted aryl, or $R^{3A}$-substituted or unsubstituted heteroaryl, wherein n is an integer from 0 to 4. and n1 and n2 are independently 1 or 2. In embodiments, $R^3$ is independently hydrogen, halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —S(O)$_{n1}$H, —S(O)$_{n2}$OH, —S(O)$_{n2}$$NH_2$, —NH$NH_2$, —O$NH_2$, —NHC(O)NH$NH_2$, unsubstituted heteroalkyl, unsubstituted cycloalkyl, unsubstituted heterocycloalkyl, unsubstituted aryl, or unsubstituted heteroaryl, wherein n is an integer from 0 to 4. and n1 and n2 are independently 1 or 2. In embodiments, $R^3$ is independently hydrogen, halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —S(O)$_{n1}$H, —S(O)$_{n2}$OH, —S(O)$_{n2}$$NH_2$, —NH$NH_2$, —O$NH_2$, —NHC(O)NH$NH_2$, $R^{3A}$-substituted alkyl, $R^{3A}$-substituted heteroalkyl, $R^{3A}$-substituted cycloalkyl, $R^{3A}$-substituted heterocycloalkyl, $R^{3A}$-substituted aryl, or $R^{3A}$-substituted heteroaryl, wherein n is an integer from 0 to 4. and n1 and n2 are independently 1 or 2. $R^{3A}$ is halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —S(O)$_{n1}$H, —S(O)$_{n2}$OH, —S(O)$_{n2}$$NH_2$, —NH$NH_2$, —O$NH_2$, —NHC(O)NH$NH_2$, $R^{3B}$-substituted or unsubstituted alkyl, $R^{3B}$-substituted or unsubstituted heteroalkyl, $R^{3B}$-substituted or unsubstituted cycloalkyl, $R^{3B}$-substituted or unsubstituted heterocycloalkyl, $R^{3B}$-substituted or unsubstituted aryl, or $R^{3B}$-substituted or unsubstituted heteroaryl, wherein n is an integer from 0 to 4. and n1 and n2 are independently 1 or 2. $R^{3B}$ is halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —S(O)$_{n1}$H, —S(O)$_{n2}$OH, —S(O)$_{n2}$$NH_2$, —NH$NH_2$, —O$NH_2$, —NHC(O)NH$NH_2$, $R^{3C}$-substituted or unsubstituted alkyl, $R^{3C}$-substituted or unsubstituted heteroalkyl, $R^{3C}$-substituted or unsubstituted cycloalkyl, $R^{3C}$-substituted or unsubstituted heterocycloalkyl, $R^{3C}$-substituted or unsubstituted aryl, or $R^{3C}$-substituted or unsubstituted heteroaryl, wherein n is an integer from 0 to 4. and n1 and n2 are independently 1 or 2. $R^{3C}$ is halogen, —$N_3$, —$CF_3$, —$CCl_3$, —$CBr_3$, —$CI_3$, —CN, —COH, —OH, —$NH_2$, —C(O)OH, —C(O)$NH_2$, —$NO_2$, —SH, —S(O)$_{n1}$H, —S(O)$_{n2}$OH, —S(O)$_{n2}$$NH_2$, —NH$NH_2$, —O$NH_2$, —NHC(O)NH$NH_2$, unsubstituted heteroalkyl, unsubstituted cycloalkyl, unsubstituted heterocycloalkyl, unsubstituted aryl, or unsubstituted heteroaryl, wherein n is an integer from 0 to 4. and n1 and n2 are independently 1 or 2.

Further to any compound and embodiment thereof disclosed herein, in embodiments one or more of $R^1$, $R^{1A}$, $R^{1B}$, $R^{1C}$, $R^2$, $R^{2A}$, $R^{2B}$, $R^{2C}$, $R^3$, $R^{3A}$, $R^{3B}$, $R^{3C}$, $R^{4A}$, $R^{4B}$, $R^{4C}$, $R^{5A}$, $R^{5B}$, $R^{5C}$ is a size-limited substituent, wherein each substituted or unsubstituted alkyl is independently a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl. Further to any compound and embodiment thereof disclosed herein, in embodiments one or more of $R^1$, $R^{1A}$, $R^{1B}$, $R^{1C}$, $R^2$, $R^{2A}$, $R^{2B}$, $R^{2C}$, $R^3$, $R^{3A}$, $R^{3B}$, $R^{3C}$, $R^{4A}$, $R^{4B}$, $R^{4C}$, $R^{5A}$, $R^{5B}$, $R^{5C}$ is independently a lower substituent, wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl. Further to any compound and embodiment thereof disclosed herein, in embodiments $L^1$ and/or $L^2$ is a size-limited substituent, wherein each substituted or unsubstituted alkyl is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and each substituted or unsubstituted heterocycloalkyl is a substituted or unsubstituted 3 to 8 membered heterocycloalkyl. Further to any compound and embodiment thereof disclosed herein, in embodiments $L^1$ and/or $L^2$ is independently a lower substituent, wherein each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and each substituted or unsubstituted heterocycloalkylene is a substituted or unsubstituted 3 to 7 membered heterocycloalkylene.

The scintillator-activated photocleavable linker having the structure of Formula (I) can have the formula:

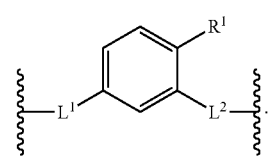

(Ia)

In Formula Ia, $R^1$, $L^1$ and $L^2$ are as described herein, including embodiments thereof. Further to any compositions including the structure of either of Formulae (I) or (Ia), $R^1$ can be —$NO_2$. $L^2$ can be —(CH$_2$)$_{n3}$—O—C(O)—, wherein n3 is an integer from 0 to 5, e.g., 0, 1, 2, 3, 4, or 5. n3 can be 1.

Further to any compositions including the structure of either of Formulae (I) or (Ia), $L^2$ can be bound to the chemical agent moiety. In embodiments, $L^2$ forms part of the chemical agent moiety Further to any composition disclosed herein, the chemical agent moiety can be covalently bound to the scintillator-activated photocleavable linker through an amine group on the scintillator-activated photocleavable linker thereby forming an —NH— connecting moiety. The term "—NH-connecting moiety" and the like refer, in the usual and customary sense, to a second amine acting as a covalent linkage between substituents on the amine nitrogen. Alternatively, the chemical agent moiety includes an —NH— group that serves as the point of attachment of the chemical agent moiety to the scintillator-activated photocleavable linker (e.g. the $L^2$ group). Thus, upon cleavage this —NH— groups becomes an —$NH_2$ group attached to the remainder of the released drug (e.g., as in the Doxorubicin example provided herein).

Further to any composition disclosed herein, the chemical agent moiety can be a drug moiety, a hormone moiety, a metal moiety, a radioprotective moiety, a cement moiety, a nucleotide triphosphate moiety, a protein moiety, a polysaccharide moiety, a neurotransmitter moiety, an enzyme moiety, a tissue factor moiety or a detectable moiety. The chemical agent moiety can be a drug moiety. The chemical agent moiety can be a hormone moiety, as known in the art. The chemical agent moiety can be a metal moiety, e.g., a metal or metal chelate in combination with a metal. The chemical agent moiety can be a radioprotective moiety, as known in the art. The chemical agent moiety can be a cement moiety, as known in the art. Cement moieties in this context can be multivalent reactive species which can bind two or more components to be cemented together. The chemical agent moiety can be a nucleotide triphosphate moiety, as known in the art. The chemical agent moiety can be a protein moiety, as known in the art. Exemplary protein moieties in this context can include antibodies, protein hormones, and cytokines and other cell signaling proteins, as known in the art. The chemical agent moiety can be a polysaccharide moiety, as known in the art. The chemical agent moiety can be a neurotransmitter moiety, as known in the art. The chemical agent moiety can be an enzyme moiety, as known in the art. The chemical agent moiety can be a tissue factor moiety, as known in the art. The chemical agent moiety can be a detectable moiety. When bound to the nanocrystal scintillator, the drug moiety can be a prodrug moiety. The drug moiety can be an anticancer drug moiety or an antibiotic drug moiety. The drug moiety can be an anticancer drug moiety. The term "anticancer drug moiety" and the like refer, in the usual and customary sense, to a drug moiety found useful in the treatment or amelioration of cancer, as known in the art. The drug moiety can be an antibiotic drug moiety, as known in the art.

An exemplary chemical synthesis scheme for a yttrium oxide scintillator nanocrystal is set forth in Scheme 1 following. In the scheme, an aminosilane modified yttrium oxide nanoparticle ("$Y_2O_3$") having a scintillation activator is shown having aminosilane groups eminating from the surface. Reaction of doxorubicin-NHCO conjgated with NHS ester of para-nitrophenylate with the free amine group affords the scintillator nanocrystal linked to a chemical agent moiety through a scintillator-activated photocleavable linker. Subsequent irradiation ("Radiation") of the scintillator nanocrystal affords a photon which is absorbed by the scintillator-activated photocleavable linker causing cleavage. The resulting species are Doxo (containing the resultant —$NH_2$ moiety), $CO_2$, and the scintillator nanocrystal now attached to the remnants of the photocleavage linker.

Scheme 1. Scheme for synthesizing yttrium oxide nanoparticles covalently linked to radiation cleavable doxorubicin or other drug.

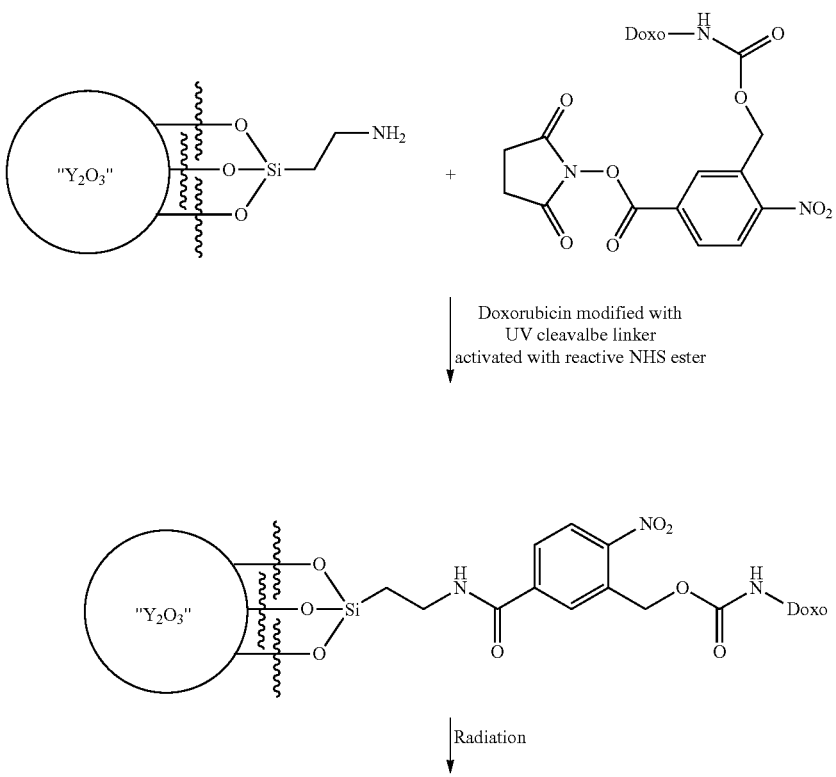

-continued

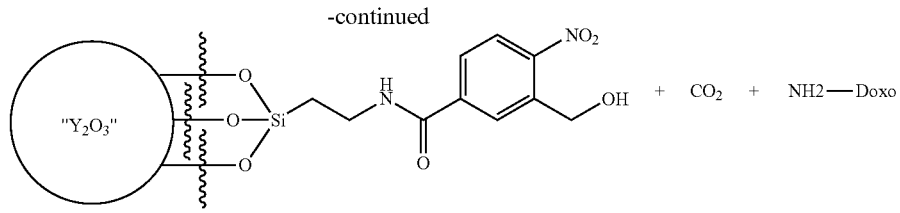

II. Pharmaceutical Compositions

In another aspect, there is provided a pharmaceutical composition including a composition including a scintillator nanocrystal linked to a chemical agent moiety through a scintillator-activated photocleavable linker, as disclosed herein, in combination with a pharmaceutically acceptable excipient (e.g., carrier).

Suitable pharmaceutically acceptable excipients include, for example, pharmaceutically, physiologically, acceptable organic or inorganic carrier substances suitable for enteral or parenteral application that do not deleteriously react with the scintillator nanocrystal linked to a chemical agent moiety through a scintillator-activated photocleavable linker, or any components thereof. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds described herein.

1. Formulations

The compositions described herein can be prepared and administered in a wide variety of oral, parenteral, and topical dosage forms. Thus, the compounds described herein can be administered by injection (e.g., intravenously, intramuscularly, intracutaneously, subcutaneously, intraduodenally, or intraperitoneally). Also, the compounds described herein can be administered by inhalation, for example, intranasally. Additionally, the compounds described herein can be administered transdermally. It is also envisioned that multiple routes of administration (e.g., intramuscular, oral, transdermal) can be used to administer the compounds described herein.

Accordingly, pharmaceutical compositions comprising a pharmaceutically acceptable carrier or excipient and one or more compounds are contemplated.

For preparing pharmaceutical compositions, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the scintillator noncrystal composition. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compositions with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures are injectable, sterile solutions, preferably oily or aqueous solutions, as well as suspensions, emulsions, or implants, including suppositories. In particular, carriers for parenteral administration include aqueous solutions of dextrose, cyclodextrins, saline, pure water, ethanol, glycerol, propylene glycol, peanut oil, sesame oil, polyoxyethylene-block polymers, and the like. Ampoules are convenient unit dosages. The compositions described herein can also be incorporated into liposomes or administered via transdermal pumps or patches. Pharmaceutical admixtures suitable for use include those described, for example, in PHARMACEUTICAL SCIENCES (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and/or thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation can be in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. In embodiments, the unit dosage form can be in the form of an applicator pre-filled with a pharmaceutical composition described herein (for example, a pharmaceutical composition that contains an effective amount of a scintillator nanocrystal linked to a chemical agent moiety through a scintillator-activated photocleavable linker). In embodiments, the pre-filled applicator can be filled with a pharmaceutical composition in the form of a cream, a gel or an ointment that contains a compound described herein.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

2. Effective Dosages

Pharmaceutical compositions include compositions wherein the active ingredient is contained in a therapeutically effective amount, i.e., in an amount effective to achieve its intended purpose. The actual amount effective for a particular application will depend, inter alia, on the condition being treated, as judged by a practioner in the medical or verterinary arts. For example, when administered in methods to treat cancer, such compositions will contain an amount of active ingredient effective to achieve the desired result (e.g., decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds described herein.

Dosages may be varied depending upon the requirements of the patient and the compound being employed. The dose administered to a patient should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compositions that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g., Fingl et al., *In: THE PHARMACOLOGICAL BASIS OF THERAPEUTICS*, Ch. 1, p. 1, 1975. The exact formulation, route of administration, and dosage can be chosen by the individual physician in view of the patient's condition and the particular method in which the compound is used.

III. Methods of Use

In another aspect, there is provided a method for delivering a chemical agent moiety to a target site. The method includes: (i) providing a composition including a scintillator nanocrystal linked to a chemical agent moiety through scintillator-activated photocleavable linker as disclosed herein to a location at or near a target site and (ii) cleaving the chemical agent from the remainder of the composition by exposing the composition to radiation thereby delivering the chemical agent to the target site. The term "target site" and the like refer, in the usual and customary sense, to a site which can benefit by local administration of the chemical agent moiety. In medical applications, the chemical agent moiety can be a drug moiety, a hormone moiety or a detectable moiety.

In another aspect, there is provided a method of delivering a chemical agent moiety to a subject. The method includes: (i) administering a composition including a scintillator nanocrystal linked to a chemical agent moiety through scintillator-activated photocleavable linker as disclosed herein to the subject, and (ii) cleaving the chemical agent from the remainder of the compound by exposing the composition to radiation thereby delivering the chemical agent to the subject.

The subject can be a a cancer patient and the chemical agent moiety can be an anticancer drug agent, and the composition can be administered to the subject in a therapeutically effective amount.

IV. Other Aspects

The following definitions and embodiments apply to only to the compounds disclosed in this section (i.e. section IV) and embodiments P1 to P5 listed below.

In a first aspect, there is provided a radiation activated nanoparticle assembly comprising a multilayered nanoparticle in external contact with a lipid-proreagent. The multilayered nanoparticle includes a scintillator core, an inert hydrophilic shell, and an external lipid bilayer. The lipid-proreagent includes a head group, a plurality of tail groups, and a proreagent attached at the head group with a photocleavable linker.

In embodiments, of the radiation activated nanoparticle assembly, the plurality of tail groups contact the external lipid bilayer.

In embodiments, the proreagent is released from the lipid-proreagent by scission of the photocleavable linker.

In embodiments, scission results from release of light from the scintillator core in response to radiation impinging thereon.

The terms "radiation activated nanoparticle assembly" and the like refer to compounds and assemblies described for Section IV wherein a multilayered nanoparticle is associated with a lipid-proreagent. The association of multilayered nanoparticle with the lipid-proreagent can be covalent, e.g., covalent bonding to the external lipid bilayer of the mulitlayered nanoparticle, or noncovalent, e.g., association with the external lipid bilayer of the mulitlayered nanoparticle by physiochemical processes known in the art, e.g., electrostatic, van der Waals, hydrophobic interaction, and the like.

The terms "prodrug," "prodrug moiety," "proreagent" and the like are used according to the plain ordinary meaning and is intended to represent covalently bonded carriers, which are capable of releasing an active ingredient (e.g., a drug) when the prodrug is administered to a subject. Accordingly, the terms "proreagent" and the like in this context refer to compounds which are covalently bound to a carrier (e.g., lipid moiety) via a linker, e.g., a photocleavable linker. Cleavage of the photocleavable linker results in release of the reagent. In one embodiment, the proreagent includes a therapeutic agent, a biodistribution agent, or a labeling agent. Thus, the term "proreagent" in the context of the release of a therapeutic drug, is synonymous with the term "prodrug." The term "lipid-proreagent" in the context of compounds disclosed herein refers to a proreagent bound to a lipid through a photocleavable linker. The terms "biodistribution agent" and the like refer, in the customary sense, to chemical species which can modulate the distribution of the radiation activated nanoparticle assembly within a subject, as known in the art, e.g., polyethylene glycol, as described herein. The terms "labeling agent" and the like refer, in the customary sense, to chemical species which can provide a detectable signal, e.g., fluorescent or colored dye, radioactive emitter, spin labeling reagent, and the like.

1. EXAMPLES (SECTION IV)

Example 1 (Section IV). Overall Research Design and Scope

Example 1.1 (Section IV). Preparation of Scintillator Nanocrystals

Preparation of scintillator nanocrystals of various compositions and quantification of their quantum light yield, between 360 and 380 nm, can be demonstrated in response to a range of radiation doses and energies. Our target is to attain 28,000-46,000 photons/MeV at doses≤2 Gy which should be attainable as scintillators used for dosimetry robustly emit at low doses.

Example 1.2 (Section IV). Quantum Yield Quantification of Scintillators According to Radiation Dose Nanopowdered scintillators can be exposed to X-rays between 0.1 and 10 Gy (≈1 Gy increments, 2 Gy/minute) and energies between 250 KeV and 6 MeV. The scintillator with the greatest photon yield at low doses (0.1-2 Gy) can be selected for further development as a nanoparticle. Photon emission of ≥28,000 photons at 2 Gy or less is the goal.

Example 1.3 (Section IV). Encapsulation of Scintillators

Encapsulation of the most efficient scintillator with a hydrophilic shell which in turn can be coated with a lipid bilayer is desired. See FIG. 1. Lipids in this bilayer can be chemically linked to a cancer drug, e.g., doxorubicin (Dox). Dox potently suppresses human glioblastoma (GBM) cells in culture, but clinically it causes acute and long term toxicity, which is dose-limiting, so that only a portion of the IC90 dose used in vitro can in the clinical setting be delivered to brain tumors. Linking Dox to a nanocrystal can render it inactive and non-toxic so that high doses may be administered, which in turn can facilitate the accumulation of significant concentrations of the drug within the tumor. The accumulated Dox can then be activated by localized irradiation only in the vicinity of brain tumors.

Example 1.4 (Section IV). Connecting Linker

Exemplary linkers connecting a cancer drug, e.g., Dox, to the lipid coated nanocrystal have been designed, synthesized, and tested to be disrupted by ultraviolet (UV) light at 360 nm. This linker can be adapted for the coated nanocrystal platform (FIG. 1). This linker breakage wavelength was selected because at wavelengths much longer than 350-360 nm the light will not have sufficient energy to break bonds, and at shorter wavelengths photo-induced damage of the drug will begin to occur.

Example 1.5 (Section IV). Rate and Extent of Drug Release

The rate and extent of Dox release with irradiation can be measured and quantified. The potency of the nanocrystal-Dox platform, with/out activating radiation, against human GBM grown in culture can be compared to Dox in free form, and in the context of integrin-based tumor targeting versus non-targeting.

Example 1.6 (Section IV). Maximum Tolerated Dose (MTD)

The maximum tolerated dose (MTD) of free Dox and nanocrystal bound Dox can be assessed with IV tail vein injection, employing protocols well known in the art.

Example 1.7 (Section IV). In Vitro Potency Again Primary Human Glioblastoma Cells in Culture In vitro potency of scintillator nanocrystal-Dox platform against primary human glioblastoma cells in culture can be determined. Established and primary human GBM cell lines grown in vitro can either have the scintillator nanocrystal-Dox platform added, free Dox, nanocrystals only, and can receive a range of radiation doses or no radiation. Survival of the cells can be measured and compared statistically.

Example 1.8 (Section IV). Brain Entry, Biodistribution and Toxicity

Without wishing to be bound by any theory, it is believed that nanoparticles can enter the brain tumors via leaky tumor microvessels. In addition recent reports indicate that PEGylated liposomes bearing Dox cross the blood brain barrier (BBB) and that transferrin ligand (iron) significantly potentiated the movement of liposomes across the BBB. For these reasons related to the ability to permeate tumors and penetrate the BBB, the nanoparticles can incorporate these moieties, and the influence of size on BBB permeation can be assessed using various diameters of nanoparticles, e.g., 100-150 nm and 50 nm.

Biodistribution is an important issue for eventually moving ahead to clinical studies with nanoparticles, although the non-toxic nature of the nanocrystal-Dox prodrug can reduce side effects to major organs assuming the Dox is stably attached to the nanocrystal in the absence of radiation. The in vivo distribution of fluorescent nanocrystals and the yield of Dox after a single injection of free drug or nanocrystal bound Dox followed by irradiation, can be determined for a primary human GBM growing orthotopically, and for normal brain, heart, lung, spleen, liver and kidneys. The fluorescent nanocrystals can allow identification of their location and density, and we can determine the degree of correlation with precise LC mass spectroscopy measurements of actual Dox concentrations in all tissue samples. All organ samples can be examined histologically for any signs of pathology to provide preliminary toxicity data.

Example 1.9 (Section IV). In Vivo Anti-GBM Efficacy

One week after the mice are stereotaxically implanted with tumors they can be injected with free Dox or nanocrystal (50 or 100-150 nm) bound Dox at the previously determined MTD, or nanocrystal alone, then head only or sham irradiated with 1, 2, or 4 GY at four hours after injection. We can use a head only irradiation mouse holder apparatus. There can be two treatments, once a week for two weeks, and then four days after the last treatment. The mice can be sacrificed and the brain and major organs removed. The brain can be sectioned and the tumor volume measured. The mice can be weighed weekly prior to sacrifice. Major organs can be examined by histopathology for evidence of damage.

Example 2 (Section IV). Fabrication and Quantification of Radiation Scintillators

Example 2.1 (Section IV). Fabrication Methodology and Optimizing Light Output Scintillator nanocystals 100-150 nm diameter can be prepared with a photon yield of 28,000-46,000 photons/MeV and emission peaks between 330-365 nm under γ-ray excitation using cerium activated halide compositions such as $K_2LaCl_5$, $BaF_2$, $RbGd_2Br_7$ and $LaC_{13}$. The most important scintillation mechanism is energy transfer by direct electron-hole recombination on the cerium site 23. These scintillators can be prepared by various synthetic methods 15, but for fabrication of core-shell nano-sized particles, optimized low-temperature hydrothermal and co-precipitation methods are believe to be well suited.

Figure 3:
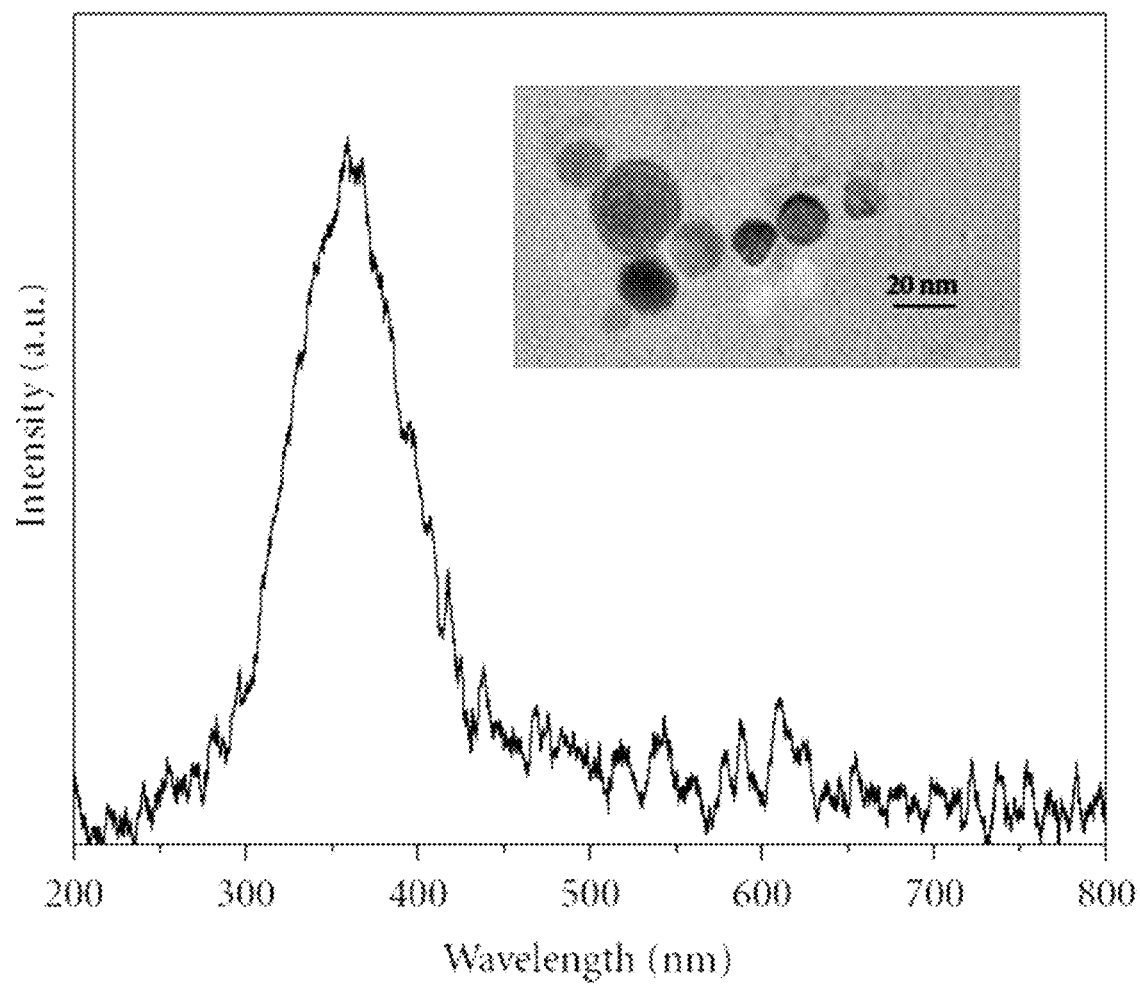
FIG. 3 depicts radioluminescence spectra and transmission electron micrograph of $BaF_2:Ce^{3+}$. Inset: transmission electron micrograph of single core $BaF_2:Ce^{3+}$ prepared by co-precipitation.
Figure 4:
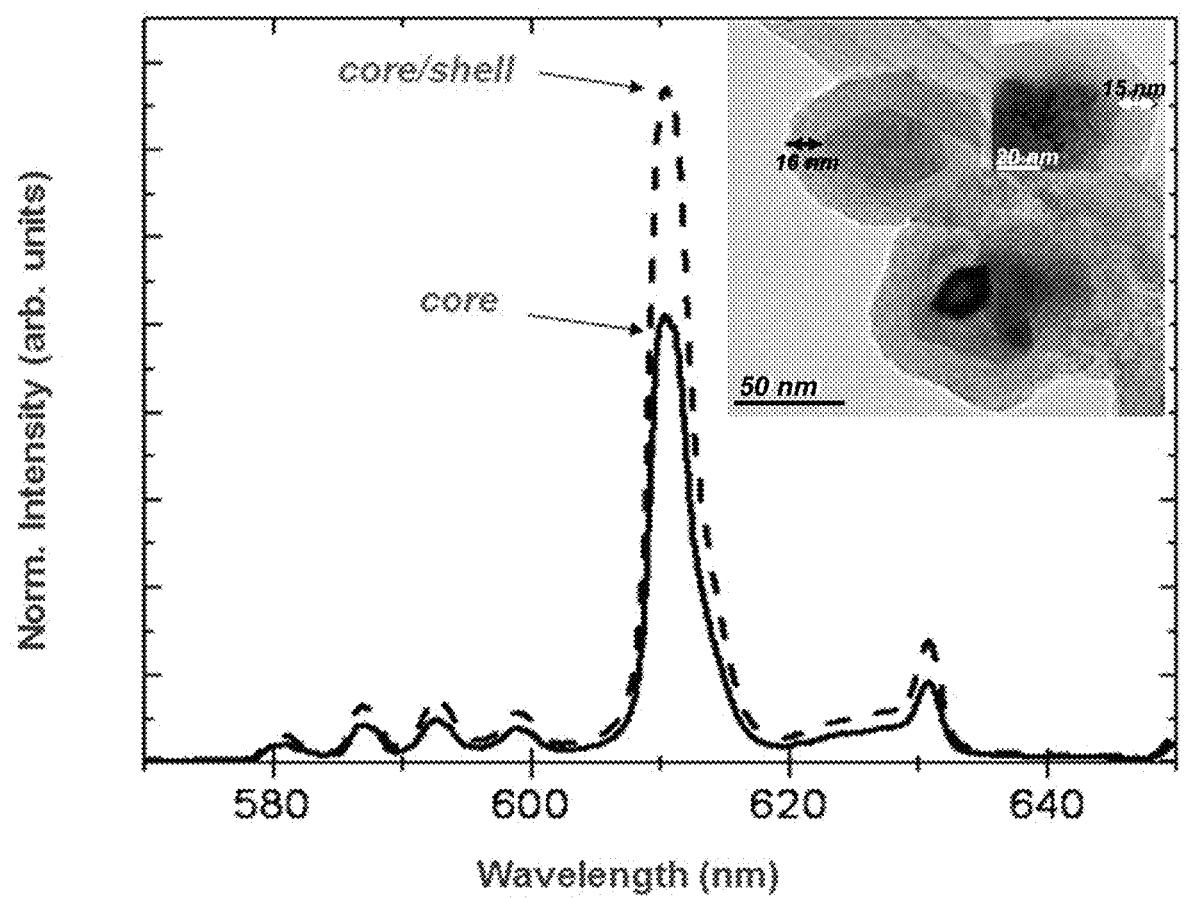
FIG. 4 depicts photoluminescence (PL) emission spectra of $Y_2O_3:Eu^{3+}$ and $Y_2O_3:Eu^{3+}/SiO_2$ core shell particles. Inset: transmission electron micrograph of the core/shell.

The challenge with nano-sized luminescent particles is the reduced quantum efficiency due to poor absorption of the excitation radiation arising from pronounced reflectance losses coupled with nonradiative relaxation at the surface states (as demonstrated in FIG. 3—the signal to noise ratio is small). To alleviate these problems, core/shell nanostructures can be used to stabilize the surface of the nanoparticles. FIG. 3 shows a transmission electron micrograph and radioluminescence spectrum of single core $BaF_2:Ce^{3+}$ prepared by co-precipitation. Note the emission peak at the required wavelength of 360 nm. This co-precipitation method was adapted to create core-shell structures as shown in FIG. 3. The photoluminescence emission intensity was 50% higher for core/shell Y2O3:Eu3+/SiO2 compared to bare core particles (FIG. 4). This strategy can be extended to emitters in the 330-360 nm UV range.

Briefly, the core/shell nanocrystals can be prepared by a Pechini sol-gel process, by dissolving in a nitric acid solution (volume ratio of water and nitric acid=1:1) to form an aqueous solution. Subsequently, 4.2 g citric acid which acts as chelating agent for metal ions, and 2.23 ml ethylene glycol (EG) can be introduced (molar ratio of metal:CA:EG=1:1:2). Then 5 g polyethylene glycol (PEG) as a cross-linking agent can be added into the aqueous solution to effect a PEG concentration of 0.05 g/ml. The solution can be continuously stirred for 10 h at 80° C. to form a transparent gel. This gel can be preheated at 300° C. for 1 h, and then calcined at 800° C. for 1 h in a furnace in air to remove organic materials and to obtain the nanophosphor powders.

Example 2.2 (Section IV). Coating Scintillator Nanocrystals with an Inert Hydrophilic Surface Inert silica can be applied to allow later coating with the lipid bilayer. This process can be started with the hydrolysis of TEOS in alcohol, water, and ammonia. First, 1 g of the core particles can be added to 30 ml 1-propanol. The mixture can be agitated using ultrasonification for 1.5 h to disperse the core particles. Then, 0.5 ml of deionized water, 0.4 ml NH4OH and 0.1 ml TEOS can be added. The ratio between the concentrations of core particles and reagents ($H_2O$, $NH_4OH$ and TEOS) can be adjusted to avoid self-nucleation of silica and thus, the formation of core-free silica spheres. The reaction can be continued in the ultrasonicator to obtain more dispersed core and uniform $SiO_2$ coating on the core. In order to prevent heating of the solution and to better disperse the nanoparticles, ice can frequently be added into ultrasonification bath and the bath temperature fixed at 20° C. Centrifugation can separate reaction products from the suspension and rinsed with ethanol four times. The concentration of H$_2$O and NH$_4$OH in the 1-propanol solution may be controlled, instead of lengthening the deposition time, because the change of concentration of H2O and NH4OH has been noted as a comparatively efficient way to deposit thicker SiO2 shells.

Example 2.3 (Section IV). Quantum Efficiency of Scintillators

The quantum light yield with radiation exposure (1-10 Gy) can be measured with known quantities of nanocrystals in a cuvette and measuring light output with an ultrasensitive CCD array. This work can be performed by adjusting X-ray dose and energy directed at a sample cuvette for materials surface studies. A sensitive CCD detector can be positioned to capture nanopowdered scintillator emission in response to 0.5, 1, 2, 3, 4, 5, 6, 7, and 8 Gy of X-rays applied at energies of 250 KeV to 2, 4 and 6 Mev. The acquired data can be adjusted to account for $4\pi$ (all directions) light emission and, based on the quantity of scintillator material, the quantum yield can be calculated. The scintillator can be selected that generates the most photon yield at low doses, and preferably lower energies.

Example 3 (Section IV). Nanocrystal-Dox Prodrug Platform Assembly

Example 3.1 (Section IV). Nanocrystal Lipid Coating

The most efficient scintillator nanocrystal can be surface modified with a variously hydrophilic, inert material to facilitate the attachment of functionalized lipid components in a bilayer. The surface-functionalization method of the scintillator nanocrystal can utilize alkoxysilane molecules with hydrophilic amino groups at the end—3-aminopropyltriethoxysilane, NH$_2$(CH$_2$)$_3$Si(EtO)$_3$, (3-APTES) (>98%, Alfa Aesar). Eu powders can be dispersed in acetone under mild agitation. Subsequently, 5 vol % 3-aminopropyltriethoxysilane can be added drop-wise, and the solution can be magnetically stirred at the boiling temperature of acetone (56° C.) and under flowing N2 gas for 180 minutes. The solution can be centrifuged and the particles that remain can be washed with acetone and dried in air. These particles can then be dispersed in deionized (DI) water. The lipid bilayer is described in Table 1 and can include multiple types of lipids, e.g., 1, 2, 3, or more types, as well as (i) polyethylglycol moieties, (ii) UV radiation crosslinkable acetylene groups, and (iii) synthetic αvβ3/α5β1 receptor ligands (Table 1). The relative surface composition of the resultant nanoparticles can be similar to what we have successfully used in previous studies for other applications.

TABLE 1

Proposed nanocrystal external lipid layer constituents.

| Constituent | Percent of Outer Shell |
|---|---|
| Fluor (Rhodamine) | 2 |
| DSPC-PEG 2000 | 10 |
| UV Crosslinkable acetylated DOPE | 5 |
| αvβ3/α5β1 ligand (-PEG-DOPE) | 5 |
| Cholesterol | 10 |
| DOPE | 30 |
| DSPC | 28 |

DOPE = dioleophosphadylethnalolamine
DSPC = distearoylphophatylcholineBODIPY = 6-(4,4-difluoro-5-(2-thienyl-4-bora-3a,4a-diaza-s-indacene-3-yl)styryloxy-acetyl)aminohexamido-DOPE

Example 3.2 (Section IV). Integrin Targeting Ligand and Fluorescent Marker Attachment Covalently attached to the lipid bilayer can be an antitumor drug, e.g., Dox, αvβ3 integrin tumor/tumor vessel targeting ligands (cyclic RGD [Arginylglycylaspartic acid]-containing peptides), fluorescent reporter (BODIPY), and/or stealth components (polyethylene glycol [PEG]) for long circulation times. Dox can be linked to the lipid layer using a photosensitive linker (i.e., photocleavalbe linker). In order to attach the RGD tumor (integrin) targeting cyclic peptide, the peptide can initially be conjugated to a short linker, succinimidyl ester-(PEO)4-maleimide, and simultaneously DSPE can be reacted with iminothiolane to produce a free thiol. The DSPE containing the free thiol group can be reacted with the peptide-(PEO)4-maleimide to produce the peptide-lipid conjugates, and these conjugates can be recrystallized in methanol/diethyl ether 1:9 at 4° C. overnight. The exact mass of the peptide-lipid conjugates can be verified by mass spectroscopy.

For BODIPY fluorescent marker conjugation to the external DOPE lipid layer, BODIPY succinamidyl ester can be dissolved in DMSO, to which can be added triethylamine and DOPE dissolved in chloroform. The reaction mixture can be stirred for 60 min, and the solvent removed. The dry residue can be dissolved in chloroform.

Example 3.3 (Section IV). Diameters of Nanoparticles

Various sizes of nanoparticles can be made and evaluated, e.g., a 100-150 nm diameter group for primary tumors and metastatic sites, and a second group of 50 nm diameters with transferrin ligand attached for general brain penetration across the blood brain barrier (BBB). Nanoparticle structural optimization can be guided by charge/size measurements (Malvern Zetasizer) and electron microscopy (see below).

Without wishing to be bound by any theory, it is believed that ultimately from a clinical standpoint the larger particles will primarily be intended to deliver a significant drug payload to primary tumors and vascularized metastatic foci, while the smaller 50 nm particles are intended to more readily penetrate the BBB, release their payload after carefully directed irradiation, and the free drug will engage poorly vascularized, or less leaky tumor areas, as well as infiltrating single cells in areas or normal brain. The behavior and efficacy of nanoparticles having different particle size can be assessed in an animal model.

Example 3.4 (Section IV). Photosensitive Linkage of Dox to the Nanocrystal Lipid Coating This part of the nanoparticle assembly sequence lies at the heart of this potentially transformative technology. The ability to efficiently release Dox previously bound to be non-toxic can be triggered by UV light, e.g., at approximately 350-360 nm. The chemical linker can be the same one we have used to make a light sensitive Dox prodrug, except that for the presently proposed research the linker can attach Dox to the lipid surface of the scintillator nanocrystal.

To prepare the linkage Dox can be dissolved in DCM and with lipid coated nanocrystals, and can be added to 1-(3-nitrophenyl) ethyl carbonochloridate in DCM at 1:1 molar ratio. The reaction mixture can be stirred vigorously with a magnetic Teflon-coated stir bar for 30 min. The linked drug product can be purified by HPLC semiprep purification. Without wishing to be bound by any theory, it is believed that the overall yield of linked drug can be up to 70% or more, 70%, 80%, 90% or more, and that the linkage will be stable at neutral pH.

Figure 2:
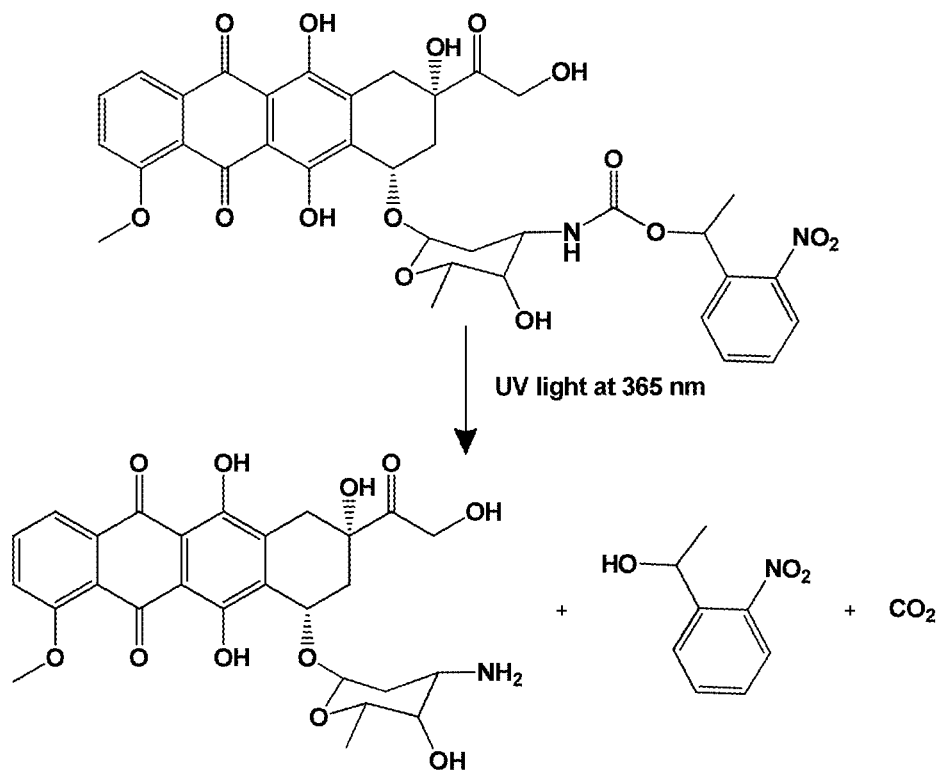
FIG. 2 depicts light activation scheme using a linker, as exemplified in FIG. 1. Cytotoxic Dox is shown below on the left after UV light exposure.

Releasing free drug from the nanocrystal conjugate is based upon the photocleavable characteristic of the nitrophenyl group. The mechanism of photolysis has been adapted from established mechanisms and is shown schematically in FIG. 2. Light absorption at 365 nm causes the electron configurations in the nitrophenyl group to rearrange, inducing the formation of an unstable 6-membered ring with one of the nitro group's oxygen atoms. The destabilization and rearrangement of this ring causes the cleavage, releasing the carbamate group along with drug. The carbamate undergoes hydrolysis in aqueous conditions, producing $CO_2$ and free drug. This linker can attach Dox to the nanocrystal lipid coating.

Example 3.5 (Section IV). Integrin Targeting Ligand Structure and Synthesis

Figure 5:
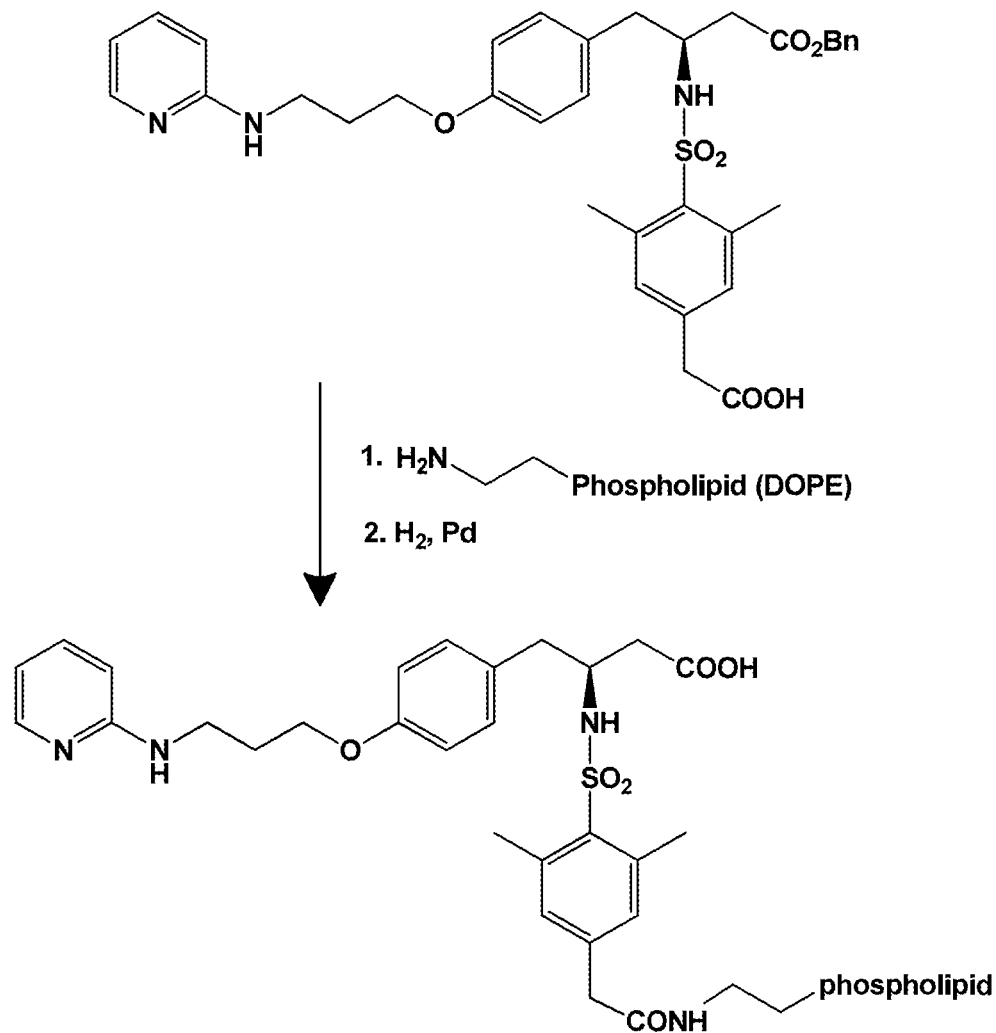
FIG. 5 depicts an exemplary design scheme for the synthesis of a dual, a5B1/avb3 ligand, and conjugation of this ligand to DOPE lipid. The table notation ($IC_{50}$) indicates that biochemical binding of this ligand to both integrins is very effective, i.e., low nanomolar range.

The tumor and tumor vasculature targeting component of the liposome can be synthesized by the reaction of a peg activated-DOPE lipid with reactive covalently linkable $\alpha v \beta 3/\alpha 5 b 1$ ligand, shown in FIG. 5.

Example 4 (Section IV). Physical Characterization of Scintillator Nanoparticle-Dox Platform

Example 4.1 (Section IV). Size, Charge and Morphology

The nanoparticle suspension can be diluted in 1/10 in MilliQ water, and 100 µl of the dilution sized with a Zetasizer using light backscattering. The same instrument can be used to measure the particle net charge expressed in mV. Morphology and size can be further characterized using scanning electron microscopy (SEM). Samples can be prepared by dropping 5 µl of particle suspension onto a polished silicon wafer. After drying the droplet at room temperature overnight, the sample can be coated with chromium and then imaged by scanning electron microscopy (SEM).

Example 4.2 (Section IV). Evaluation of Doxorubicin (Dox) Attachment Efficiency For the assessment of the Dox content the nanocrystal-Dox platform can be dissolved in DMSO containing 0.004% HCl. After ultrasonication for 20 min, the insoluble material can be separated by centrifugation for 15 min at 16,000 g. The concentration of Dox in the supernatant can be measured spectrophotometrically at 480 nm. The attachment efficiency (percentage of Dox bound to nanocrystals) can be calculated as the difference between the initial drug content and the amount of free Dox in the filtrate after separation of the nanoparticles by ultrafiltration.

Example 4.3 (Section IV). Doxorubicin Release from Scintillator Nanocrystals without Irradiation The stability of the nanocrystal-Dox platform and the kinetics of Dox release from the nanocrystals can be investigated in aqueous milieu. Non-irradiated nanocrystal-Dox can be added to Milli-Q water and the release at 1, 4, 6 8, and 12 hours quantified. For the irradiation tests the nanoplatform can be suspended in Milli-Q water, and diluted 25-fold with water. Then the diluted suspension can be incubated at 37° C. under constant stirring at 150 rpm and irradiated with X-rays at doses including 0.5, 1, 2, 3, 4, 5, 6, 7, 8, 9, and 10 Gy at 2 Gy/min and at between 250 KeV and 6 MeV. For analysis 3 ml aliquots of the irradiated and non-irradiated suspensions can be centrifuged (20,000 g for 30 minutes at ambient temperature) to separate the nanocrystals. The concentration of Dox in the supernatant can be measured by spectrophotometry at lambda max=480 nm.

Example 5 (Section IV). In Vitro Potency of Radiation Activatable Nanocrystal-Dox Platform The nanocrystal-drug platform and free Dox can be suspended in physiological saline and added to both established and primary human glioblastoma cell lines (U87, GBM4/8) grown in cell culture, with RPMI medium supplemented with antibiotics, at 370 C and with 30% CO2. Two and four hours after addition of the nanoparticles or drug, separate groups of flasks can be irradiated at doses ranging from 0.5, 1, 2, 3, 4, 5, 6, 7, 8, 9, Gy of X-rays at 2 Gy/min. The test conditions can be: Irradiation alone, irradiation and free drug, irradiation and nanocrystal only, free drug only, irradiation and nanocrystal with bound drug, integrin targeted nanocrystal (50 vs. 150 nm) with bound drug, and non-targeted nanocrystal (50 nm vs. 150 nm) with bound drug.

Twenty-four hours after irradiation the cells can be washed with phosphate buffered saline, replenished with fresh medium, and cultured for an additional 6 days. Cell colonies can be fixed with ethanol, stained with Giemsa, and the cell population expressed as a percentage of the non-irradiated, non-drug controls.

Statistical Analysis: In vitro GBM cell killing by the radiation-activated nanoparticle-drug can be assessed by dividing the average number of viable cells from three plate replicates (per nanoparticle and radiation dose level), by the average of three controls. At a type I error rate of 0.05, using a one-sided t-test, we will have 80% power to evaluate whether a decrease in mean percent viable cells is significantly lower than 100%, conservatively assuming standard deviation percent viable cells is 15%.

Example 6 (Section IV). In Vivo Tumor Accumulation and Kinetics of the Nanocrystal-Dox Platform

Example 6.1 (Section IV). Maximum Tolerated Dose and Clearance Kinetics in Health Mice To determine the in vivo maximum tolerated dose for free and nanocrystal bound DOX (50 nm, 150 nm), both can be administered I.V. to 10 BALB/c mice (total=30 mice) at doses of 0 (PBS), 20, 40, and 60 mg/kg DOX equivalents. The weights and general health of the mice can be monitored until the 14th day after injection, or until mice in the group receiving the highest dose become lethargic and show obvious signs of morbidity such as reduced weight, reduced food intake. At the conclusion of the experiment all mice can be sacrificed and blood can be collected, serum separated and analyzed for serum creatine kinase, lactic dehydrogenase, and serum transaminase to determine the presence of damage to muscle tissue and to the liver at various dose levels.

Preliminary pharmacokinetic (PK) studies can be performed. Briefly, test mice can be given escalating doses of the fluorescence nanocrystal bound Dox. PK studies can be performed on healthy balb/c mice in sets of 8 mice per PK variable. Mice can receive the nanocrystal-Dox by intravenous injection, and the PK variables and their acceptable limits can include; (1) Circulation half-life ($t_{1/2}$>1 hour), (2) Area under the curve (AUC>200 hr/ng/ml), (3) Distribution volume (Vss>2× body water), rate of elimination (CL>50% of blood flow), (4) the ratio of AUC (brain)/blood). Groups of 10 mice can receive either 1 mg/kg, 10 mg/kg, 20 mg/kg, 30 mg/kg, 40 mg/kg or 50 mg/kg inhibitor intravenously via the tail vein. The brains and plasma of different treated mice can be removed at 0.1, 0.5, 1, 2, and 4 hours after receiving inhibitor (two mice per dose at each time point), homogenized and a small aliquot can be removed to measure fluorescence. The homogenate can be spiked with an internal standard, and subjected to organic extraction and LC-Mass spectrometry. A standard curve of concentration/peak area for Dox can serve as a reference and can be correlated with sample fluorescence measurements.

Example 6.2 (Section IV). Pulse Dosing

High-dose pulse regimens, transferrin ligand (iron), and PLGA, can be explored to enhance brain entry of the nanocrystal-Dox platform. The attendant risk of increased toxicity can be avoided by high doses administered for a shorter time period or less frequently. Doses of the MTD, 100 and 300 mg/kg free DOX equivalent can be assessed in terms of brain concentration of drug as previously described in a total of 30 mice. The brains and plasma of different treated mice can be removed and subjected to organic extraction and LC-Mass spectrometry to quantify Dox levels. One goal is to attain a micromolar brain concentration which can demonstrate the need and feasibility of dosing for later preclinical and possibly human studies.

Example 6.3 (Section IV). Tumor Accumulation and Biodistribution

For these studies primary GBM tissue can be acquired from fresh surgical specimens (IRB approval/infrastructure in place) which undergo mechanical and enzymatic dissociation for isolation and in vitro culture of tumor-initiating stem cells. The dissociated tissue can be washed, filtered through a 30 μm mesh and plated onto ultra-low adherence flasks at a concentration of 500,000 to 1,500,000 viable cells/ml. The stem cell isolation medium can include human recombinant EGF, human bFGF and heparin. The tumor initiating stem cells routinely grow in suspension and form spheres comprised of a mix of GBM cell types. Sphere cultures can be passaged by dissociation, washing and resuspension in neural stem cell culture medium. The cells can be concentrated into a compact suspension (200,000 cells/1 μL), and injected stereotaxically into the right frontal cortex of nu/nu mice (3 mm depth). The mice can all be randomized after all of them have been implanted. This model recapitulates the natural history of GBM in human patients, exhibiting infiltrative invasion and an irregular tumor morphology.

The tumor accumulation rate of the integrin-targeted and non-targeted liposomes can be characterized according to nanocrystal fluorescence and LC-Mass spec measurements of Dox. Briefly, at one week after tumor inoculation, the mice can be injected with the lipid coated nanocrystals in increments of two hours after injection, up to 8 hours, and thereafter at 24 hours, mice can be injected with the vascular marker FITC-lectin, and sacrificed. There can be 30 mice per time point for a total of 120 (10 targeted and 10 non-targeted receiving nanocrystal Dox at the MTD/pulsed dosing optimum, and 10 mice receiving free Dox at the free Dox MTD) and at each time point the brain, heart, kidneys, lungs, and spleen can be removed from the cohort of mice. The fluorescence associated with the brain tumor can be imaged using a small animal fluorescence imager.

The tumors can be imaged in brightfield transmitted light mode and fluorescence mode at 4×, 10×, 20× and 40× to determine the extent of nanocrystal associated fluorescence imaged. The images can consist of single focal plane XY frames. The total fluorescence at the tumor site can be quantified and normalized as the proportion of illuminated pixels out of the total image pixels. The other organs can be sectioned and also imaged and then processed for histology. The resultant fluorescence data sets for both targeted and nontargeted liposomes can be plotted for each post-injection time point to show tumor accumulation, and to reveal the optimal time of nanoparticle accumulation at the tumor site to guide radiation exposure. Samples of the tumor, normal brain and other organs can be homogenized, extracted in ethyl acetate, dried and resuspended in water for LC mass spec. The concentration of Dox per μg of tissue can be determined and compared statistically with the percentage fluorescence at each time point. The major organ sections can be examined by a histopathologist for the signs of tissue damage.

Example 7 (Section IV). In Vivo Efficacy and Toxicity of Scintillator Nanocrystal-Dox Platform In order to clearly demonstrate any enhanced efficacy and reduced systemic toxicity provided by the scintillator nanocrystal—Dox prodrug platform, in vivo experiments with a realistic GBM model and the appropriate controls can be done. Testing can be done using an orthotopic cancer stem cell based GBM model that authentically recapitulates the human disease. As described previously human primary GBM can be prepared and implanted stereotaxically into the right frontal cortex of nu/nu mice. We can implant 10 mice per group for a total of 200 mice and the major treatment injection groups can be: (i) saline controls, (ii) coated nanocrystals without liposomes, (iii) free Dox, (iv) coated non-targeted nanocrystals with Doxorubicin, and (vi) coated tumor/tumor vessel targeted nanocrystals with Dox (50 nm nanoparticles and with/out transferrin and 100 nm). The previously determined MTD can determine dosing. The first treatment can be 7 days after tumor implantation. The mice can be treated intravenously once per week for two weeks with the MTD (free Dox and liposomal Dox). At 4 hours after both injections, the mice can be lightly sedated with ketamine administered subcutaneously, and placed in a custom holder with body shielding to receive head only gamma or sham irradiation at 2 Gy/min with 1 or 2 Gy at 1.12 MeV. Three days after the second treatment the mice can be deeply anesthetized with Nembutal and a 2 ml blood sample can be acquired, after which the subjects can be euthanized with $CO_2$ and the brain, heart, lungs, spleen, kidney and liver can be removed for histology. Table 2 shows the set of experiments to be conducted.

TABLE 2

Array of testable conditions using GBM tumor bearing mice.

| Dox | NANOCRYSTAL | TARGETED | HEAD IRRADIATION | PARTICLE SIZE (nm) | Dose (Gy) | Transferrin |
|---|---|---|---|---|---|---|
| — | — | — | sham | 100 | 1.2 | — |
| X | — | — | X | 100 | 1.2 | — |
| — | X | — | sham | 100 | 1.2 | — |
| — | X | — | X | 100 | 1.2 | — |
| X | X | — | sham | 100 | 1.2 | — |
| X | X | — | X | 100 | 1.2 | — |
| X | X | X | X | 100 | 1.2 | — |
| X | X | X | X | 100 | 1.2 | X |
| X | X | X | X | 50 | 1.2 | — |
| X | X | X | X | 50 | 1.2 | X |

Example 7.1 (Section IV). Quantitative Measurements of Tumor Response and Toxicity The measurements and comparisons listed below can be used to compare the experimental groups indicated in Table 2:

1—Primary Tumor Response—The tumor volume can be determined from serial H&E slides using commercial software to define the tumor and calculate volume derived from all slices. The data can be compared statistically between groups.

2—Number of Detectable Metastases—The metastases to surrounding the primary tumor can be mapped from serial H&E sections. The number and mean size of these foci can be compared between the treated groups.

3—Analysis of proliferation—To assess the proliferating cells, immunohistochemical staining with antibodies against Ki67 can be performed. The Ki67-labeling index can be expressed as the ratio of positively stained tumor cells of all cells determined from at least six random high power fields (40× in each subject).

4—Determination of necrotic areas—For evaluation of necrosis the H&E-stained slides can be examined using a semi-quantitative scoring system: 0, no necrotic area; 1, solitary necroses; 2, less than 50% of the tumor area occupied by necroses; 3, more than 50% of the tumor cells per area in the necrotic state.

5—Assessment of Systemic toxicity—All mice can be weighed before tumor implants, daily during drug treatment, and at experiment conclusion, to reveal any accelerated weight loss due to systemic drug toxicity. The samples of blood, lung, liver heart, GI tract, pancreas and kidneys can be prepared and sent the UCS Cancer Center Histology Core for hematology and histopathology. The presence, number and severity of any abnormalities can each be tabulated for every group, and compared statistically between groups.

Statistical Analysis.

ANOVA models can be built to compare a continuous outcome (e.g., tumor volume, number of metastases, toxicity measures—compared separately) between groups and logistic models to compare a binary outcome (e.g., a binarized toxicity outcome). To demonstrate the enhanced efficacy of using targeted nanocrystal-Dox and irradiation within free Dox or nanocrystal-Dox groups among tumor bearing mice, Jonckheere-Terpstra rank-based trend tests can be used for continuous outcomes and Cochran-Armitage trend tests for binary outcomes to test for a trend with respect to the subgroups in the same order as they are listed in Table 2.

Sample Size and Power.

With 10 mice per group, considering the comparison using targeting and the primary tumor response between Dox and nanocrystal-Dox, i.e., tumor volume, using a two-sided t-test, at a type I error rate of 0.05, we will have 80% power to detect a mean difference of 1.4 standard deviations of the tumor volumes, etc. Other comparisons, involving main effects or tests of trend across multiple groups, will have increased power as the sample sizes will be larger.

Example 8 (Section IV). Development of UV-Emitting Nanoscintillators to Release Prodrugs for Treatment of Brain Tumors: Novel Strategy for Drug Delivery on Specific Sites by Using YAG-Pr Nanoscintillators Abstract.

Ultraviolet emitting YAG-Pr nanoscintillators were produced by combustion synthesis and post-annealed in air at 1200° C. The X-ray diffraction analysis revealed the formation of the cubic garnet $Y_3Al_5O_{12}$ crystalline structure and TEM revealed the morphology and size of nanocrystalline clusters that were successfully deagglomerated with ultrasonic processing. Praseodymium was used as the impurity dopant in this complex structure at concentration levels in range of x=0.5~2.0 at. % that yield strong UV emission band ($\lambda$=300~400 nm) originated from $4f5d \rightarrow {}^3H_4$ transitions within the $Pr^{3+}$ electronic levels efficiently activated with UV photons of shorter wavelength ($\lambda$=292 nm). Radioluminescence experiments were also performed by using high energy x-Ray photons (50 MeV) resulting in a dramatic enhancement of the $4f5d \rightarrow {}^3H_4$ transitions. These nanocrystalline praseodymium-doped yttrium aluminates provide promising optical properties to be used as nanoscintillators in modern medicine for the development of novel drug delivery systems. Thus, it is expected that the UV light activated by the irradiation can trigger the release/activation of a prodrug.

INTRODUCTION

In the last few years, significant progress has been achieved in the field of nanomedicine and bionanotechnology however, design and development of nanomaterials to be used for reliable detection of diseases at an early stage and effective drug-delivery at targeted sites are still in development. Obtaining these nanomaterials in an efficient way represents a tremendous scientific challenge and effort of research.

Inorganic luminescent nanomaterials are known as nanophosphors. These fascinating nanocrystalline compounds posses the property to absorb energy (UV photons, X-ray or Infrared) and convert it into visible light. Phosphors, in general, are composed of a highly stable host lattice that can be doped with a small concentration of impurity atoms (called activators) that produce the luminescence [Oli 1997]. Phosphors are inorganic materials with luminescent properties of interest for optoelectronic devices and radiation detection, including displays, lighting and imaging.

The importance of these class of materials stems mainly form the possibility of achieving unique properties related to the reduced dimensionality and spatial confinement of the energy states, as seen in nanoscale semiconductors [Ref. 1 paper Yukihara], and the possibility of synthesis at much lower temperatures when compared to traditional methods like solid state reaction and crystal growth.

Scintillation is defined by the flash of light produced in a transparent material by the passage of a particle (electron, alpha particle, an ion, or a high-energy photon). The process of scintillation is one of luminescence whereby light of a characteristic spectrum is emitted following the absorption of radiation. The emitted radiation is usually less energetic than the absorbed.

In the last decade, great research efforts are focused on the development of new and more efficient scintillation crystals for detection of ionizing radiation related mainly to imaging systems for medical diagnosis. There is no reports of the use of nanoscintillators for the use in biological systems for drug delivery at specific sites in the body.

Indeed, there is a great interest in developing nanophosphors for specific performance in new fields of medicine and biotechnology. For example it is desirable to synthesize nanophosphors that emit near-UV light ($\lambda$=300~400 nm) when exposed to radiation (X-rays or Gamma) for applications in nanomedicine as drug delivery systems. It is expected that the UV light activated by the irradiation can trigger the release/activation of a prodrug.

The main goal of research in the area of development of new strategies against brain cancer. The design of our proposal is focused on the synthesis of inorganic compounds that are able to interact with known prodrugs, with the objective of developing anticancer agents.

Since all anticancer agents interact with both normal cells and cancerous cells, the idea is to develop an anticancer prototype of action with much greater specificity. That is, strategies that can be manipulated just to destroy malignant tumors, without damaging as far as possible, healthy tissues.

Our model encompasses the development of photosensible nanostructures with anti-cancer potential. The approach of this design is based in two different mechanisms:

1. UV radiation emission due to luminescent nanoparticles activated through minimum interaction with X-rays or Gamma radiation.

2. Radical decomposition of a formulated prodrug through photolysis provided by UV photons from the nanophosphor, and induction of cellular damage by the interaction of the organometallic radicals (prodrug) with the cancer cells.

Thus, the model implies firstly, the design of organometallic based prodrug that under physiological condition are harmless for the cells, but that by exposing these clusters to highly energetic radiation, show cytotoxic activity. Secondly, the combination of luminescent nanoparticles with organometallic prodrug can imply the amplification of cytotoxic effects through the emission of UV photons by activation of the nanophosphors under radiation with higher energy in order to induce damage the malign cells.

Potential advantages of this strategy include: the specificity of the mechanism to kill malignant cells and the use of luminescent nanoparticles and organometallic clusters (in absence of radiation) harmless for the healthy tissues, of easy elimination from the biologic system due their size (less than 50-60 nm) and permeable traffic through the membranes; also the employment of radiation doses, possible lower than required in the conventional radiotherapy.

Figure 6:
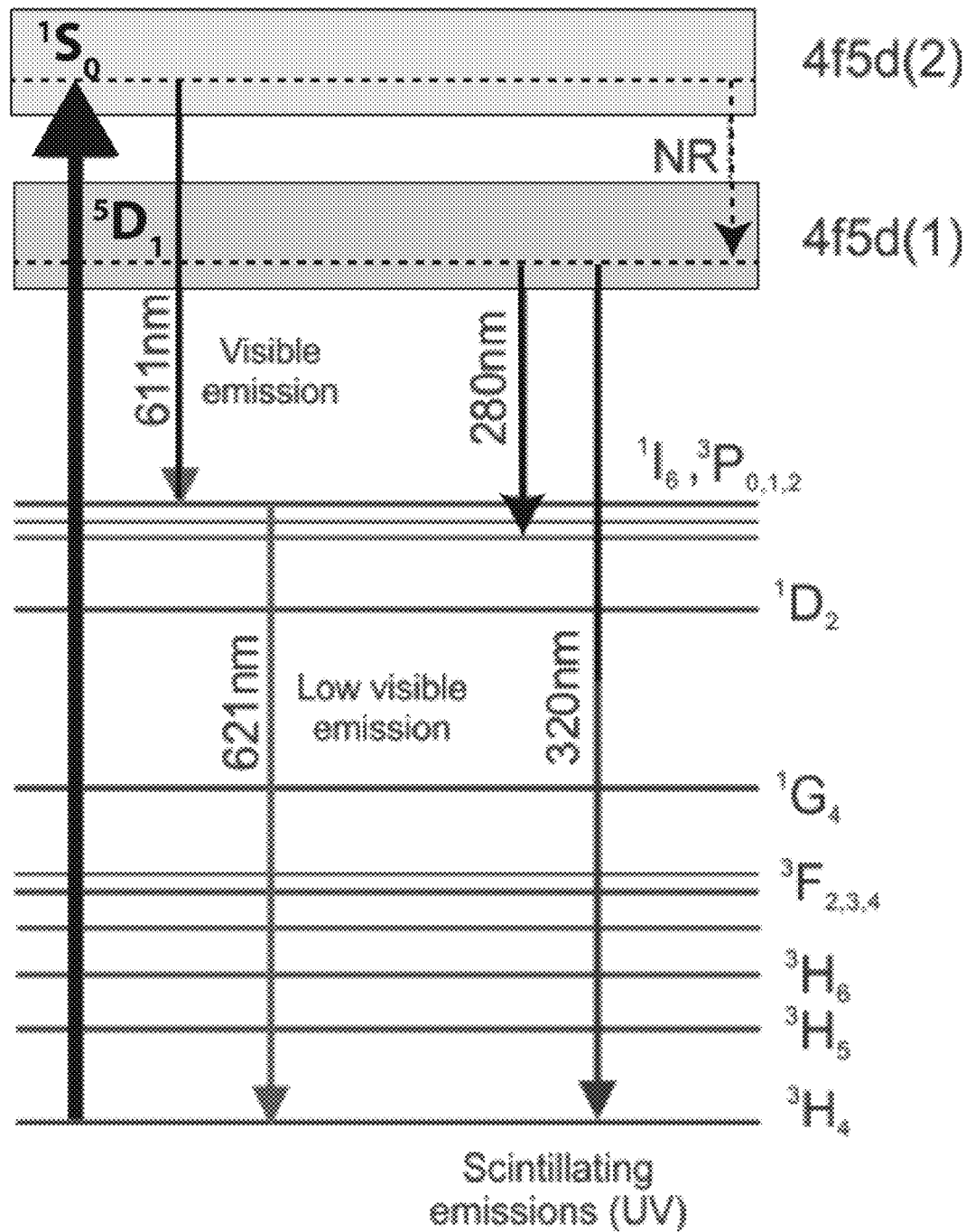
FIG. 6 depicts energy levels in $Pr^{3+}$ ion showing the electronic transitions. The 4f5d(1) and 4f5d(2) levels are boxed.

Nanophosphors with the ability to convert X-rays or Gamma rays into UV or visible photons (scintillators) are of interest. There are several compositions with optical properties that are suitable as scintillators; however, very few offer the possibility to be used in our approach. We have selected Pr-doped yttrium aluminum garnet ($Y_3Al_5O_{12}$:$Pr^{3+}$) since this formula is one of the most chemically stable under energetic radiation (e.g., X-rays or Gamma-rays). It crystallizes in a cubic garnet known as YAG. In this complex crystal yttrium ions can be substituted by rare earths leading to emit photons in a wide range of wavelengths (UV-Vis-IR). In particular praseodymium replaces yttrium to occupy octahedral sites of $D_2$ symmetry in YAG with a ground state is $^3H_4$ multiplet split by crystal field into 9 sublevels. 4f2 states of higher energy give rise to spectrally narrow parity forbidden optical transitions in the visible and the IR. See FIG. 6.

In this investigation we have developed nanophosphors that efficiently emit UV photons in the range of $\lambda$=300~400 nm. This strong UV emission is efficiently activated with X-ray radiation (radioluminescence).

Experimental

Yttrium aluminum garnet doped with praseodymium ($Y_3Al_5O_{12}$:Pr or YAG-Pr) were obtained by the combustion synthesis method [Lopex, O. A., et al., 1997, *J. Lum.*, 90:1]. Commercial precursors for the synthesis were yttrium nitrate [Alfa Æsar $Y(NO_3)_3.6H_2O$ 99.99%], aluminum nitrate [Alfa Aesar $Al(NO_3)_3.6H_2O$ 99.99%], praseodymium nitrate [Alfa Aesar $Pr(NO_3)_3.6H_2O$ 99.99%] and deionized water were pooled together in a reaction beaker. Carbohydrazide [$CH_6N_4O$, Alfa Aesar 98%] fuel was added and stirred for 20 min to form a homogenous solution. The reaction vessel containing the mixture was transferred into a pre-heated at ~530° C. in order to ignite the reaction. After the reaction (3~5 min) a white foamy product is obtained which is finely crushed with mortar and pestle prior to post-annealing treatment at 1200° C. for 2 hr. It has been found that heat treatments are crucial in order to enhance luminescence [Bosze, E. J., et al., 2007 *J. Am. Ceram. Soc.*, 90:2484]. Additional details with a description of the reaction and procedure for producing these phosphors are described in Bosze et al. 2003 [Bosze, G. A., 2003, *Mat. Sci. Eng.*, B97:265]

Typical X-ray diffraction (XRD) patterns of the powders were analyzed using a Phillips X'pert diffractometer equipped with $CuK_\alpha$ radiation ($\lambda$=0.15406 nm). Measurements in a $2\theta$=15-80° range were taken with a step size of 0.02° and a 1 sec dwell per point. Transmission electron microscopy (TEM) images were obtained with a JEOL-2010 operated at 200 kV accelerating voltage. Photoluminescence (PL) spectra were collected with a Hitachi spectofluorometer Model FL-7000. Radioluminescence measurements were performed under a x-Ray photons of 50 MeV. All measurements were performed at room temperature.

Results.

Figure 7:
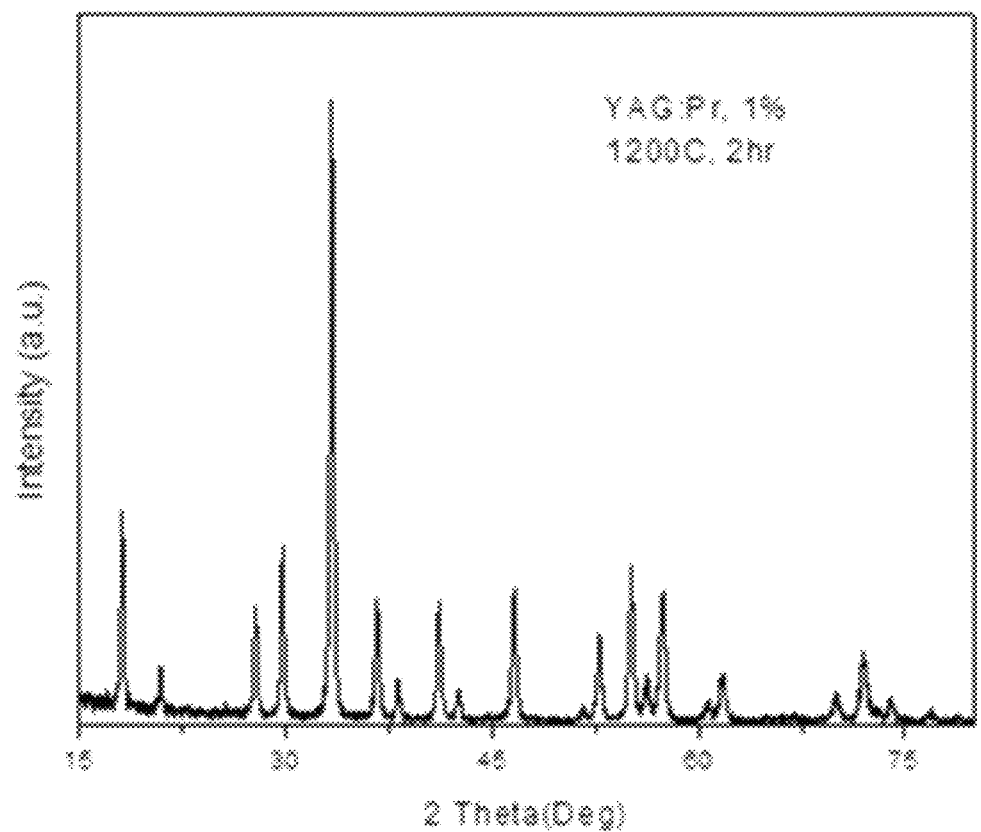
FIG. 7 depicts representative X-ray diffraction (XRD) pattern of the YAG-Pr (1 at. %) obtained by combustion synthesis and post-annealed at 1200° C. for 2 hr.

FIG. 7 shows a typical XRD pattern corresponding to the Pr-doped $Y_3Al_5O_{12}$ nanocrystalline samples produced by combustion synthesis and post-annealed at 1200° C. for 2 hr. This XRD pattern is similar to that reported in the literature for yttrium aluminum garnet crystalline structure. Identical XRD patterns were obtained for all praseodymium concentrations used in the present investigation.

Figure 8:
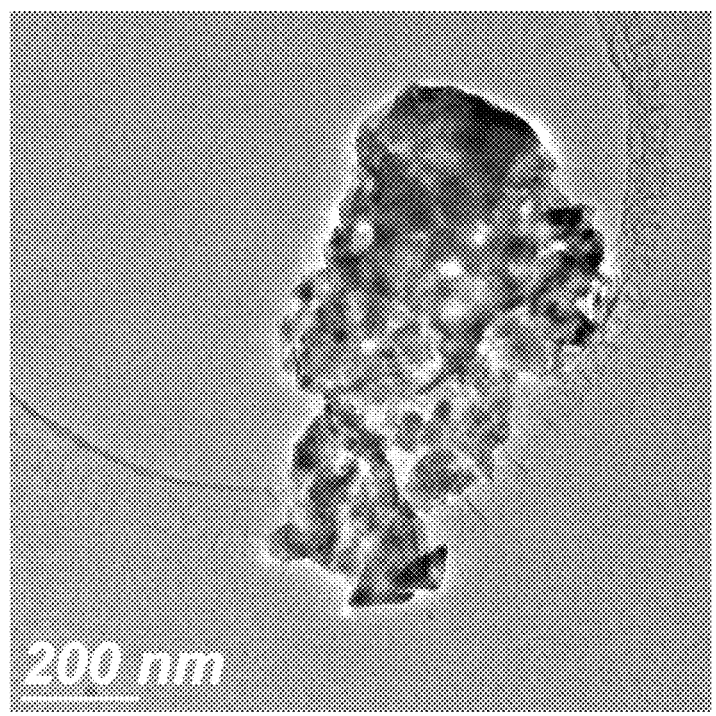
FIG. 8 depicts Transmission Electron Micrograph (TEM) image of the UV-emitting nanophosphor powder $(Y_{1-x}Pr_x)_3Al_5O_{12}$ (x=1.0 at. % Pr) analyzed at 200 kV.

In FIG. 8 a representative TEM (for the same sample as in FIG. 7) of the 1.0 at. % Pr-doped nanophosphor produced by combustion synthesis is shown. Morphology of this sample reveals a large number of irregular nanocrystallites of sizes in the range of 5.0-50.0 nm, with the most frequent size of around 30.0 nm, which confirms this phosphor powder as nanocrystalline material. Some porosity is observed which increases the amount of grain surface area which may cause the enhancement in luminescence intensity.

Figure 9:
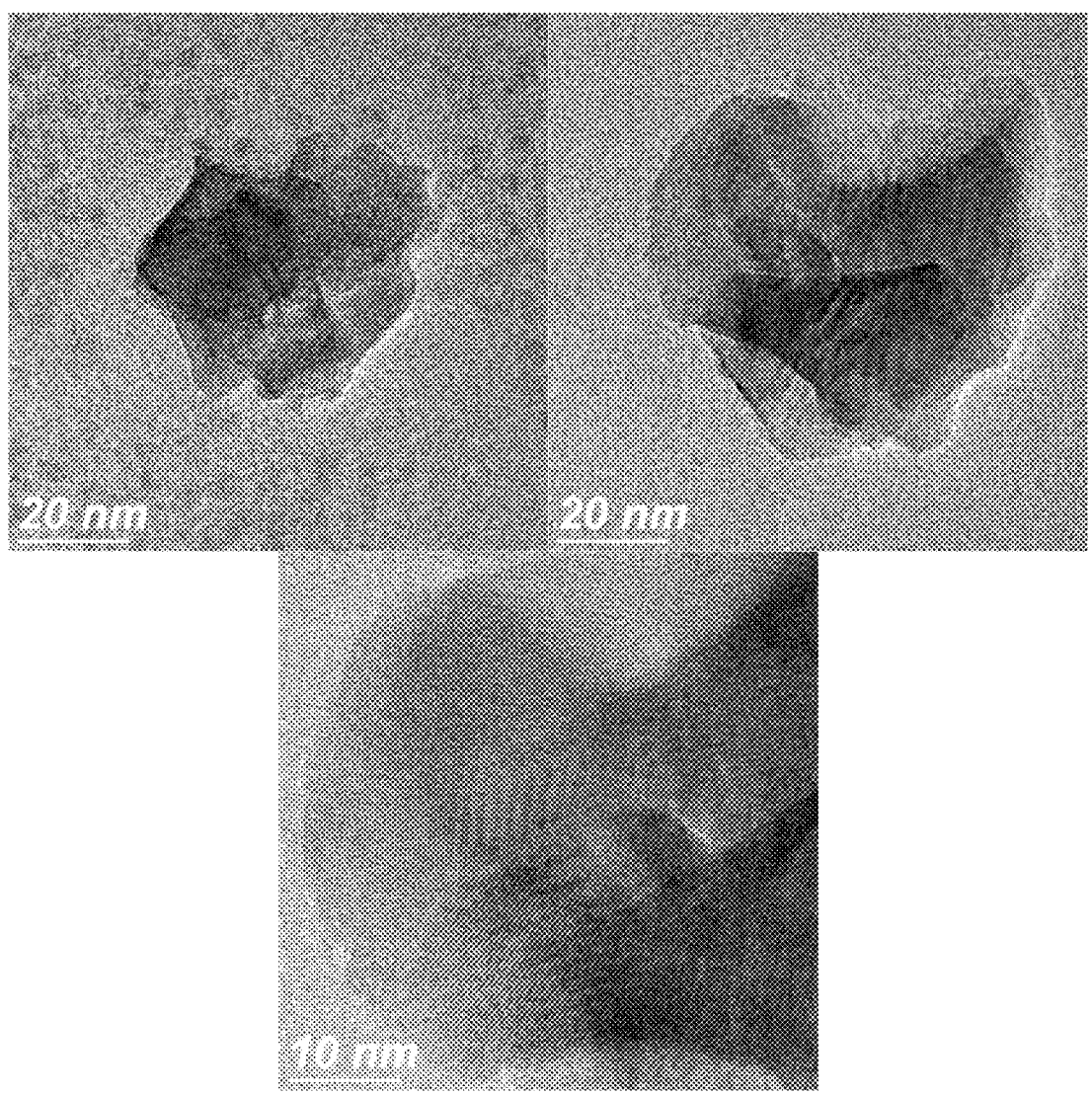
FIG. 9 depicts TEM images of representative samples of the deagglomerated nanophosphors $(Y_{1-x}Pr_x)_3Al_5O_{12}$ after ultrasonication processing of 10 min.

After ultrasonic processing for 10 min in isopropyl alcohol we have succeeded in the deagglomeration of YAG-Pr clusters obtained by combustion synthesis. See FIG. 9. These nanophosphor clusters are exploded by the ultrasonic vibrations at 24 MHz and single YAG; Pr nanoparticles in the range of 10-40 nm or clusters with smaller size of the order of 40-70 nm.

Figure 10:
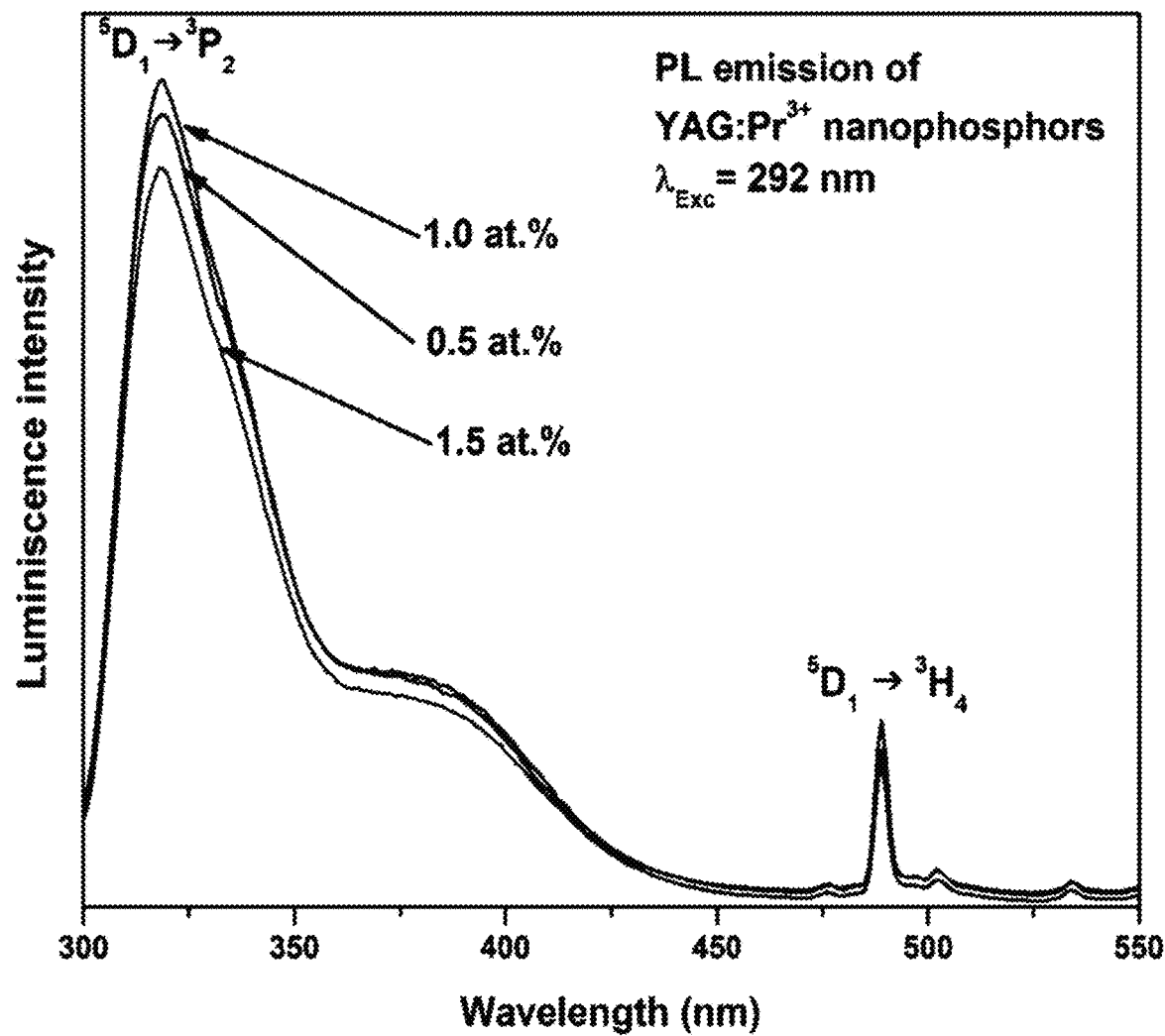
FIG. 10 depicts photoluminescence spectra of $(Y_{1-x}Pr_x)_3Al_5O_{12}$ with different Pr concentration of x=0.5, 1.0, 1.5 at. %. The excitation wavelength for all Pr-doping concentrations was $\lambda_{exc}$=292 nm.
Figure 11:
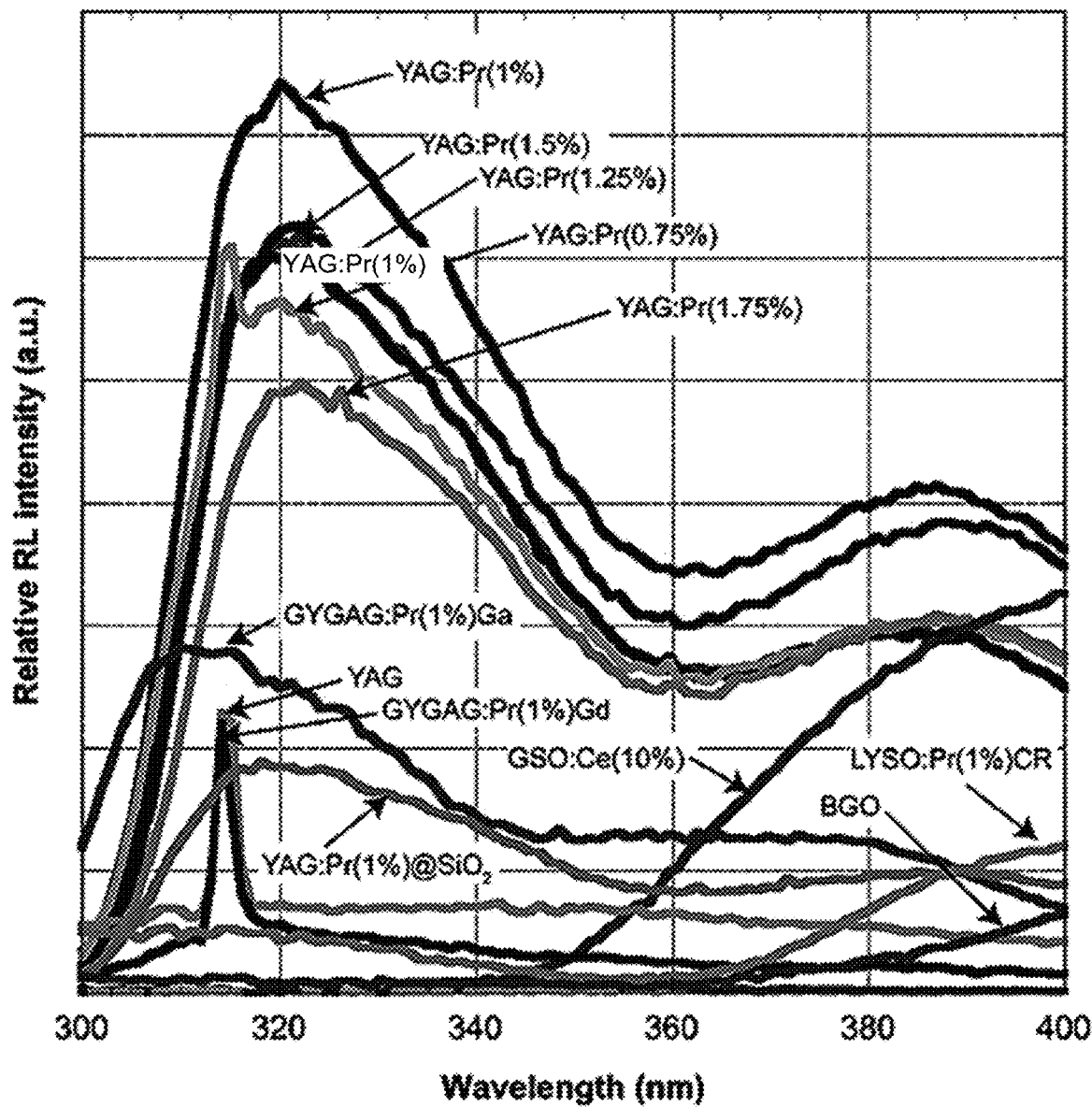
FIG. 11 depicts radioluminescence emission spectra of $(Y_{1-x}Pr_x)_3Al_5O_{12}$ with different Pr concentration of x=0.5, 1.0, 1.5, 1.75 at. %. under X-ray excitation of 50 KeV.

Photoluminescence measurements were also performed for the YAG-Pr nanophosphors. We found an optimum excitation wavelength at $\lambda_{Exc}=292$ nm for all different concentrations of Pr. FIG. 10 illustrates the photoluminescence characteristics for different concentrations of Pr in the YAG host lattice. It can be observed that the maximum PL emission occurs in the sample doped with 1.0 at. % Pr the photoluminescence is optimum. This UV emission contribution centered at $\lambda=320$ nm can be ascribed to $^5D_1 \rightarrow ^3P_2$ and a much lower PL emission band due to $^5D_1 \rightarrow ^3H_4$ electronic transitions inside the $Pr^{3+}$ ion is also detected at $\lambda=490$ nm As depicted in FIG. 11, radioluminescence spectra were investigated for $(Y_{1-x}Pr_x)_3Al_5O_{12}$ with different Pr concentration of x=0.5, 1.0, 1.5, 1.75 at. %. with X-ray excitation under 50 KeV.

Treatment of Solid Tumor.

Figure 25A:
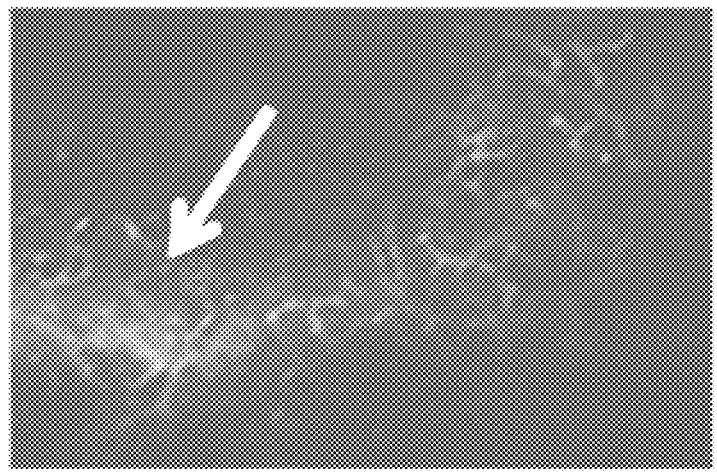
FIGS. 25A-25C. Figures depict photomicrographs of accumulation of nanoparticles at tumors with tumor regression.
Figure 25B:
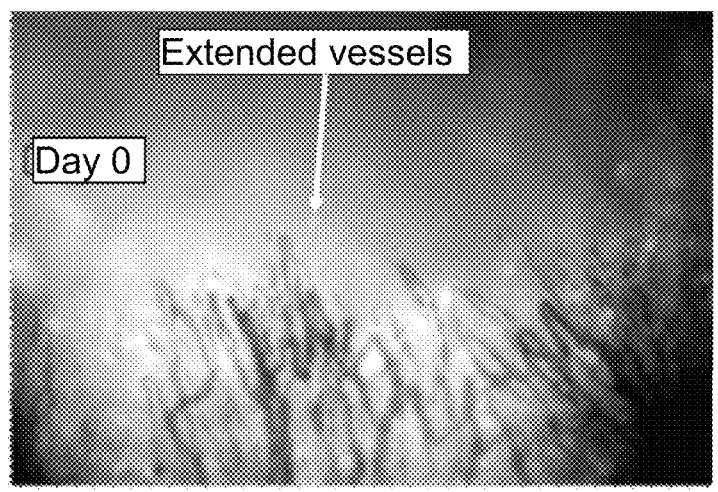
Figure 25C:
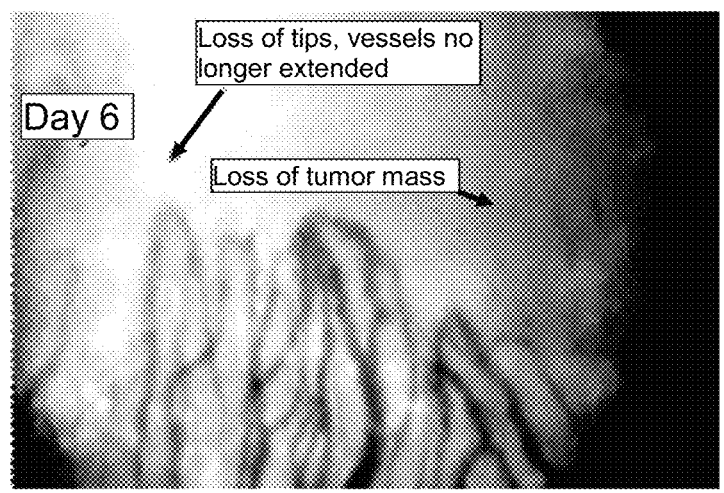

Recent reports by Munson et al., have demonstrated accumulation of liposomes carrying Dox at rat C6 glioma brain tumors with a striking suppression of tumor growth [Munson, J. M. et al. 2012, *Sci Transl Med* 4:127-136; Munson, J. et al. 2013, *Cell Cycle* 12:2200-2209]. This illustrates that liposomal agents can concentrate at brain tumors via leaky vessels (enhanced permeability and retention, EPR-effect) and exert a useful therapeutic effect. We have prepared liposomal Dox and demonstrated accumulation at tumors and effective suppression of tumor growth (FIGS. 25A-25C). Our breast cancer brain metastases model accurately emulates the human disease [Baschnagel, A. et al. *Mol Cancer Ther* 8:1589-1595].

2. EMBODIMENTS (SECTION IV)

Embodiments of the subject matter disclosed herein include Embodiments P1-P5 following.

Embodiment P1

A radiation activated nanoparticle assembly including a multilayered nanoparticle in external contact with a lipid-proreagent, the multilayered nanoparticle including a scintillator core, an inert hydrophilic shell, and an external lipid bilayer; the lipid-proreagent including a head group, a plurality of tail groups, and a proreagent attached at the head group with a photocleavable linker.

Embodiment P2

The radiation activated nanoparticle assembly according to embodiment P1, wherein the plurality of tail groups contact the external lipid bilayer.

Embodiment P3

The radiation activated nanoparticle assembly according to embodiment P1, wherein the proreagent is released from the lipid-proreagent by scission of the photocleavable linker.

Embodiment P4

The radiation activated nanoparticle assembly according to embodiment P1, wherein the scission results from release of light from the scintillator core in response to radiation impinging thereon.

Embodiment P5

The radiation activated nanoparticle assembly according to embodiment P1, wherein the proreagent is a therapeutic agent, a biodistribution agent, or a labeling agent.

V. Examples

A major contribution disclosed herein is a platform (e.g., a composition disclosed herein) that releases an agent from a scintillator nanocrystal by low doses of radiation in place of light so that a photocleavable linker is broken thereby releasing the agent. In this way drugs can be utilized as prodrugs and released. Indeed, radiation allows deep penetration, e.g., in tissues which are not susceptible to UV-visible light exposure. The scintillator lights up in response to radiation, thereby breaking a chemical linker, and releases the agent. The radiation can penetrate all tissues and many inert substances completely. Previous inventions have used toxic doses of radiation together with drugs to kill tumors. This results in considerable damage to the host, and limits the area that can be treated. In the approach disclosed herein there is employed low doses (<1 Gy) of radiation at high dose rate and pulsed, which serve to activate the chemical agent (e.g., prodrug). This means that a wide area and delicate anatomical regions can be treated, and treated repeatedly over several weeks with minimal damage to normal tissues. This larger scale of treatment increases the probability that metastatic sites and new metastases will be included in the treatment volume along with the primary tumor. The nanoparticle prodrug platform when decorated with ligands or anitbodies for cell surface receptors may facilitate entry into tumor cells and also traversal of the blood brain barrier. In the latter case while the prodrug would be taken up elsewhere in the body, release of the active drug would only occur in the brain after localized irradiation. Elsewhere the prodrug bound to the nanoscintillator composition would clear.

Example 1. $(Lu_{1-\alpha-\beta}Y_\alpha Pr_\beta)_2SiO_5$ Powders with Fast Decay Time Obtained by the Combustion Synthesis Method Abstract.

UV-emitting $(Lu_{1-\alpha-\beta}Y_\alpha Pr_\beta)_2SiO_5$ ($0.1 \leq \alpha \leq 0.4$, $\beta=0.05$, 0.005) nanophosphors were prepared by combustion synthesis and post-annealed in air at 1200° C. at different annealing times. Structural and optical properties are investigated by X-Ray Diffraction, Raman Spectroscopy and Photoluminescence measurements. The formation of monoclinic $(Lu,Y)_2SiO_5$ solid solution was confirmed by X-ray diffraction as a majority phase and under short-UV excitation the nanophosphors yielded a strong UV-emission consisting of two bands with maximum emissions located at $\lambda=280$ nm and $\lambda=315$ nm, both corresponding to the $Pr^{3+}$ forbidden transitions $^5D_2 \rightarrow 4f$ ($^3P_2$) and $^5D_1 \rightarrow 4f$ ($^3H_4$), respectively. Furthermore, luminescence decay times of 10-16 ns were measured, which depend on the rare earth ion concentration.

INTRODUCTION

In the last decade a great effort has been dedicated to the investigation of luminescent particles for multiple applications including novel types of flat TV's, electroluminescent panels, radiation detectors and scintillator panels for X-Ray radiography among others. In particular. rare earth activated oxides, oxynitrides or silicates have been widely studied due to their d applications in the medical imaging field as detectors (scintillators) in positron emission tomography (PET) equipment [H. Zaidi and A. Alavi. PET Clinics 2 (2) (2007) 109]. LSO powders have been produced to substitute single crystals [D. W. Cooke, et al., J. Appl. Phys. 88 (12) (2000) 7360], and Lu has been replaced by Y for the fabrication of $(Lu,Y)_2SiO_5$ (LYSO) crystals to reduce the high manufacturing cost [H. Loudyi, et al., Opt. Mater. 30 (1) (2007) 26]. There other reference of synthesized Ce-activated LYSO powders by combustion synthesis method, also obtaining a solid solution of the two silicates [M. Aburto-Crespo, et al., J. Lum. (2013) In Press]. Besides $Ce^{3+}$, there are other rare earth ions that can be used as activator ions in a scintillator material; one of them is $Pr^{3+}$ [C. W. E. Van Eijk, et al., IEEE Trans Nucl Sci. 41 (4) (1994) 738]. We here report a new alternative of scintillating materials: the synthesis of $Pr^{3+}$-activated LYSO powders using a low cost and fast method, combustion synthesis. The influence of the Y/Lu ratio and $Pr^{3+}$ concentration on the luminescence properties were examined. The combustion method is a fast and effective way to obtain micro or nano-scaled powders.

Experimental.

The $(Lu_{1-\alpha-\beta}Y_\alpha Pr_\beta)_2SiO_5$ powders were prepared by combustion synthesis using lutetium nitrate [Alfa Aesar $Lu(NO_3)_3 \cdot 6H_2O$ 98.%], yttrium nitrate [Alfa Aesar $Y(NO_3)_3 \cdot 6H_2O$ 99.9965%], nanocrystaline silicon oxide [$SiO_2$], praseodymium nitrate [Alfa Aesar $Pr(NO_3)_3 \cdot 6H_2O$ 99.99%] as the precursors, and hydrazine [Alfa Aesar $N_2H_4$ 98.5%] as the reductive fuel. α varied between 0.1-0.4 and β was either 0.005 or 0.05 (see Table 1-I for sample identification and α and β values). The precursors were fully dissolved in 20 ml of deionized water in a quartz beaker using a magnetic stirrer. After adding the hydrazine, a homogeneous solution was obtained with a gelatinous consistency. The quartz beaker was introduced into the high-pressure stainless steel laboratory-built reactor. Next, the temperature was raised to 105° C. and a continuous argon flow was established in order to purge and create an inert atmosphere. The reactor exhaust valve was closed and the argon inlet opened to pressurize the reactor (3.45 MPa). Using a higher pressure than ambient, nanoparticles are obtained [C. E. Rodríguez-García, et al., J. Phys. D: Appl. Phys. 41 (9) (2008) 092005] and some evidence indicates that a smaller particle size increases the luminescence emission of the phosphor [M. Nikl, et al., IEEE Trans Nucl Sci. 55 (3) (2008) 1035]. Once the reaction was completed, the exhaust valve was opened to release the pressure and the argon was used to flush the reactor until it cooled down to ~40° C. The same procedure was repeated for all samples. All powders were thermally treated in air at 1200° C. for different periods of time ranging from 2-4 h. Table 3 lists the annealing time for each sample.

TABLE 3

Concentrations of $Y^{3+}$ and $Pr^{3+}$, post-synthesis annealing time and photoluminescence decay time for combustion synthesized $(Lu_{1-\alpha-\beta}Y_\alpha Pr_\beta)_2SiO_5$ powders. All samples were thermally treated in air at 1200° C.

|  | x | y | Annealing time (h) | Decay time (ns) |
| --- | --- | --- | --- | --- |
| LYSOP1 | 0.2 | 0.05 | 2 | 16 |
| LYSOP2 | 0.2 | 0.05 | 4 | 11 |
| LYSOP3 | 0.49 | 0.005 | 4 | 10 |

Powder diffraction patterns were obtained over the scattering range $2\theta=10-60°$ with steps of 0.02° using Cu Kα radiation ($\lambda=0.15406$ nm) in a Philips X'pert diffractometer. Photoluminescence (PL) spectra were collected at room temperature with a Hitachi FL-4500 fluorescence spectrophotometer with excitation and emission slit of 2.5 nm and wavelength scan speed of 1200 nm/min. The spectrofluorometer uses a 150 W Xe lamp for sample excitation. The $Pr^{3+}$ decay emissions curves were analyzed with a HORIBA Jobin Yvon SPEX spectrofluorometer with a spectral resolution of 0.25 nm, exciting the samples with a FluoroLog-TCSPC pulse laser-diode, which produces pulses between 100-200 ps with broadband output from 180-780 nm. All the scintillating measurements were also performed at room temperature.

Results and Discussion.

Figure 12:
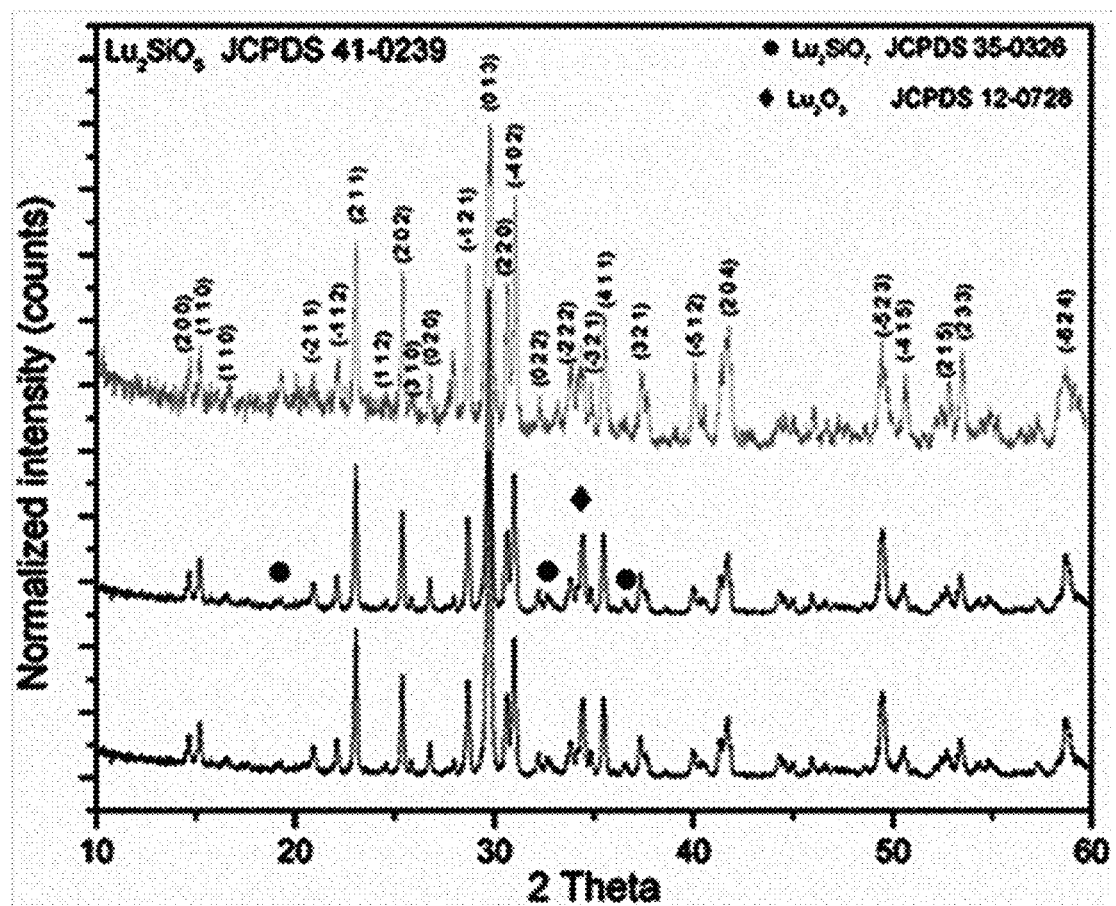
FIG. 12. X-ray diffraction patterns recorded for $(Lu_{1-\alpha-\beta}Y_\alpha Pr_\beta)_2SiO_5$ powders obtained by combustion synthesis and heated in air at 1200° C. (1) $(Lu_{0.75}Y_{0.2}Pr_{0.05})_2SiO_5$ heated for 2 h, (2) $(Lu_{0.75}Y_{0.2}Pr_{0.05})_2SiO_5$ heated for 4 h and (3) $(Lu_{0.505}Y_{0.49}Pr_{0.005})_2SiO_5$ heated for 4 h. Principal indexed peaks correspond to the monoclinic phase $Lu_2SiO_5$ JCPDS 41-0239. Two residual phases (♦) $Lu_2SiO_7$ JCPDS 35-0326 and (●) $Lu_2O_3$ JCPDS 12-0728 can be also observed in some of the patterns.

FIG. 12 shows the powder XRD patterns. Formation of a $(Lu,Y)_2SiO_5$ solid solution was obtained as a majority phase regardless of the composition and post-synthesis annealing time. The diffraction peaks of the $(Lu,Y)_2SiO_5$ powders match perfectly with the reported monoclinic $Lu_2SiO_5$ (JCPDS 41-0239). Small traces of two residual phases were identified as $Lu_2Si_2O_7$ and $Lu_2O_3$. This is in good agreement with XRD data reported by other groups for this compound [H. Loudyi, et al., Opt. Mater. 30 (1) (2007) 26], which confirms the formation of an LYSO solid solution. It is important to note that no Pr oxide phase was detected—a clear indication of excellent $Pr^{3+}$ incorporation into the host lattice.

Figure 13:
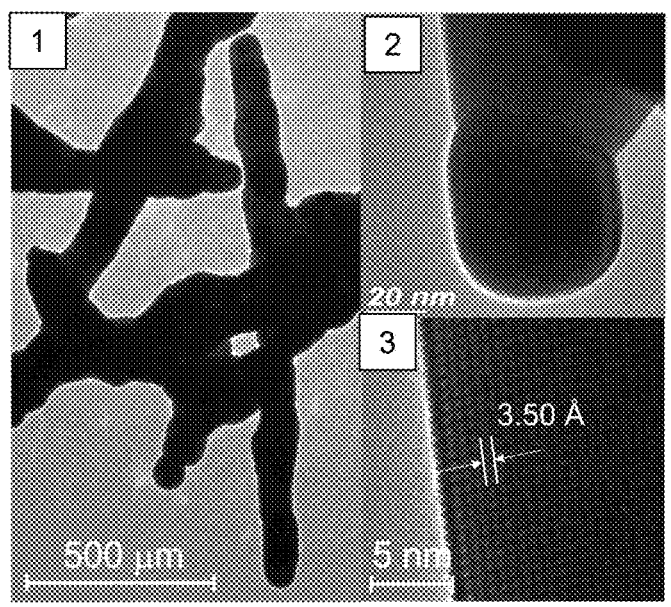
FIG. 13. TEM micrograph of the morphology observed in $(Lu_{0.505}Y_{0.49}Pr_{0.005})_2SiO_5$ powders obtained by combustion synthesis and then heated in air at 1200° C. for 6 h.

TEM micrographs (FIG. 13) show the morphology of sample LYSOP1. FIG. 13 (left panel 1) reveals rough surfaced rods of approximately 0.6 μm length. FIG. 13 (right upper panel 2) shows bars with clearly hemispherical endings of about 70 nm diameter. FIG. 13 (lower panel 3) depicts planes of a crystal with interplanar spacing of 0.350 nm, associated to the (2 0 2) planes.

Figure 14:
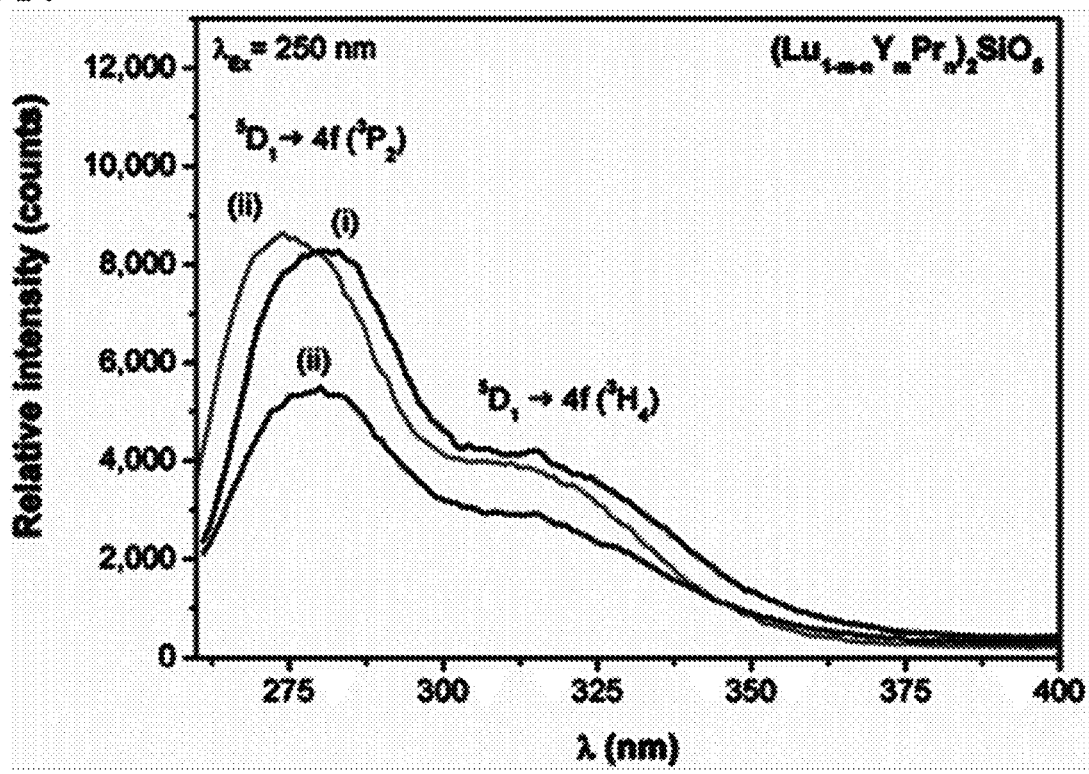
FIG. 14. Emission spectra recorded at room temperature of $(Lu_{1-\alpha-\beta}Y_\alpha Pr_\beta)_2SiO_5$ powders obtained by combustion synthesis and heated in air at 1200° C. (i) $(Lu_{0.75}Y_{0.2}Pr^{0.05})_2SiO_5$ heated for 2 h, (ii) $(Lu_{0.75}Y_{0.2}Pr_{0.05})_2SiO_5$ heated for 4 h and (iii) $(Lu_{0.75}Y_{0.2}Pr_{0.05})_2SiO_5$ heated for 4 h. Maximum emissions peaks centered at $\lambda$=280 nm and $\lambda$=315 nm, corresponding to the $Pr^{3+}$ forbidden transitions $^5D_2 \rightarrow 4f\ (^3P_2)$ and $^5D_1 \rightarrow 4f\ (^3H_4)$, respectively.
Figure 15:
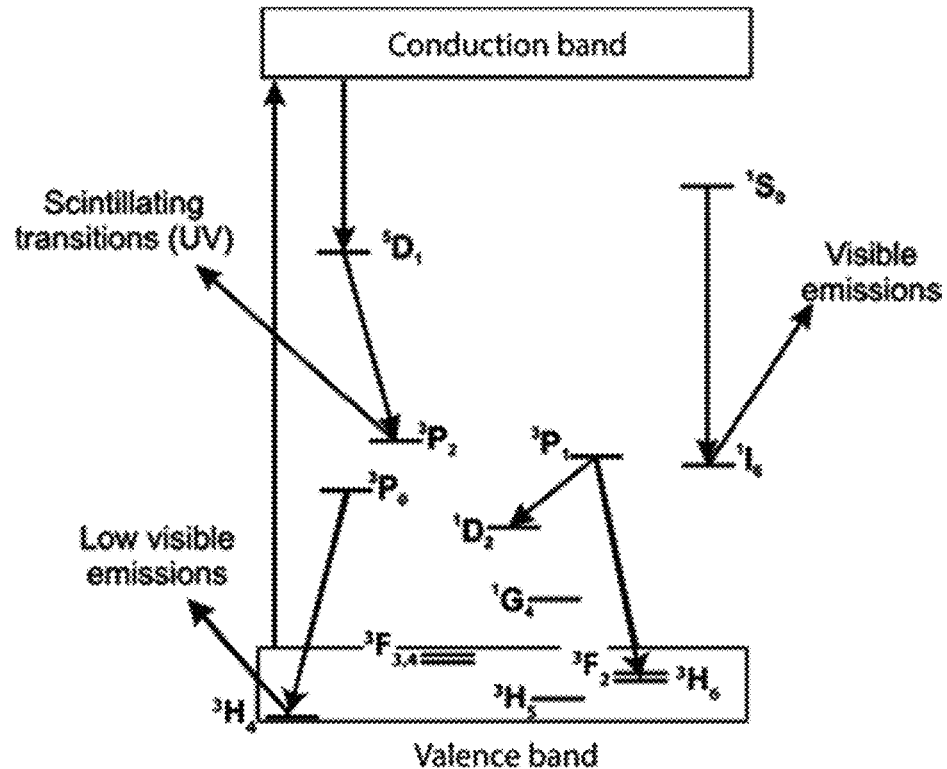
FIG. 15. $Pr^{3+}$ electronic transitions in insulator host lattice.

Photoluminescence (PL) spectra were collected at room temperature with short UV-excitation ($\lambda_{ex}=250$ nm). All samples emitted a visible dim red light. FIG. 14 shows the excitation and emission spectra of all LYSOP samples. The emission spectra range from 257 nm to 350 nm, with two major peaks centered at λ=280 nm and λ=315 nm. $Pr^{3+}$-activated LSO samples with emission spectra from 270 nm to 370 nm have been reported [D. W. Cook, et al., Opt. Mate. 27 (12) (2007) 1781] which correspond to 4f→4f transitions. It should be emphasized that when $Pr^{3+}$ ions are on a moderately strong crystalline field lattice (~6 eV) it is possible to observe the 5d→4f transitions. For the LYSO host materials in this study the band gap was 5.81 eV. On the other hand, the 5d→4f transitions are caused when a rare earth ion is in presence of an electrical field. On the LYSO host lattice, when a rare earth ion replaces a Lu ion, the unit cell has the form $RE_2(SiO_4)O$, (RE=rare earth) [P. C. Ricci, et al., J. Raman Spectrosc. 39 (9) (2008) 1268]. In this study, the negative charge of the silicate ion in the unit cell acts as an electrical field around the $Pr^{3+}$ ion consequently, the $^1S_0$ level moves above the $^5D_1$ level (FIG. 15); a second mechanism that makes the scintillating 5d→4f transitions possible. All spectra show $^5D_2$→4f ($^3P_2$) and $^5D_1$→4 f ($^3H_4$) transitions. The spectrum matches the data reported for LSO scintillator crystals activated with $Pr^{3+}$[M. Nikl, et al., 2005. Chemical Physics Letters. 410 (4-6) (2005) 218].

Figure 16A:
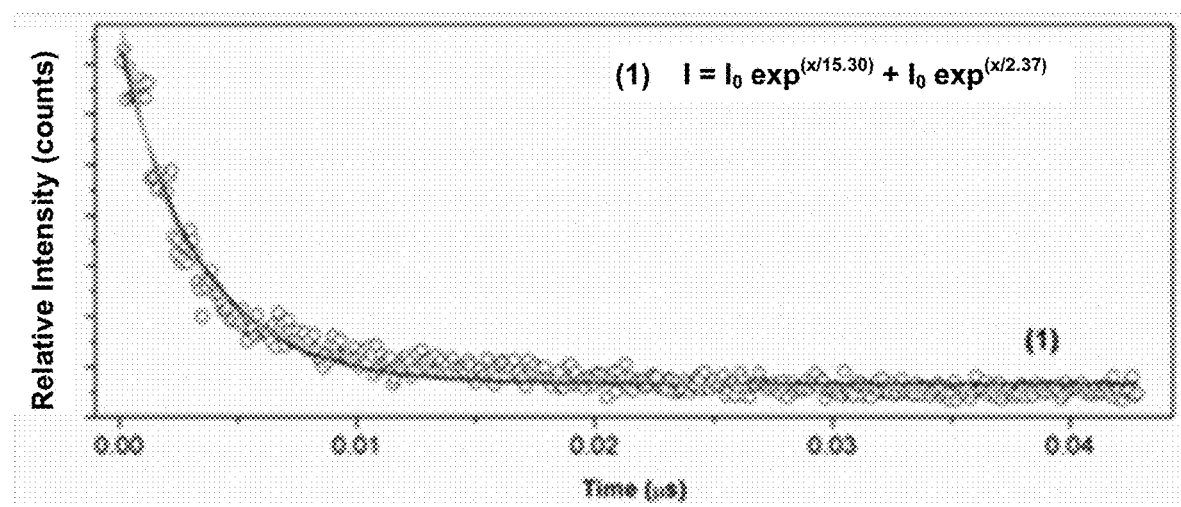
FIGS. 16A-16B. Spectral scintillation decays of samples and heated in air at 1200° C. collected at room temperature ($\lambda_{ex}$=252 nm).
Figure 16B:
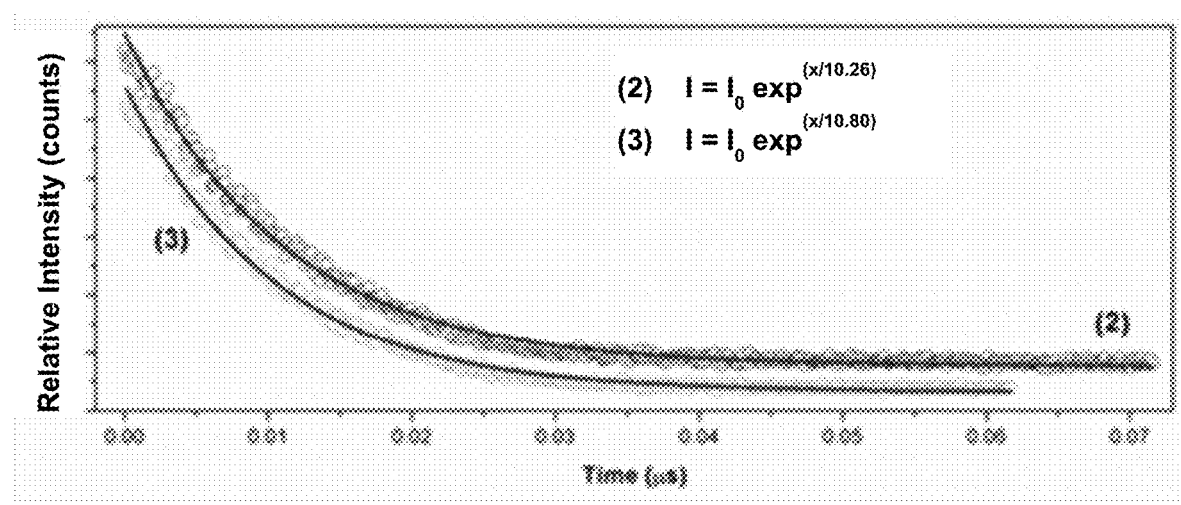
Figure 17A:
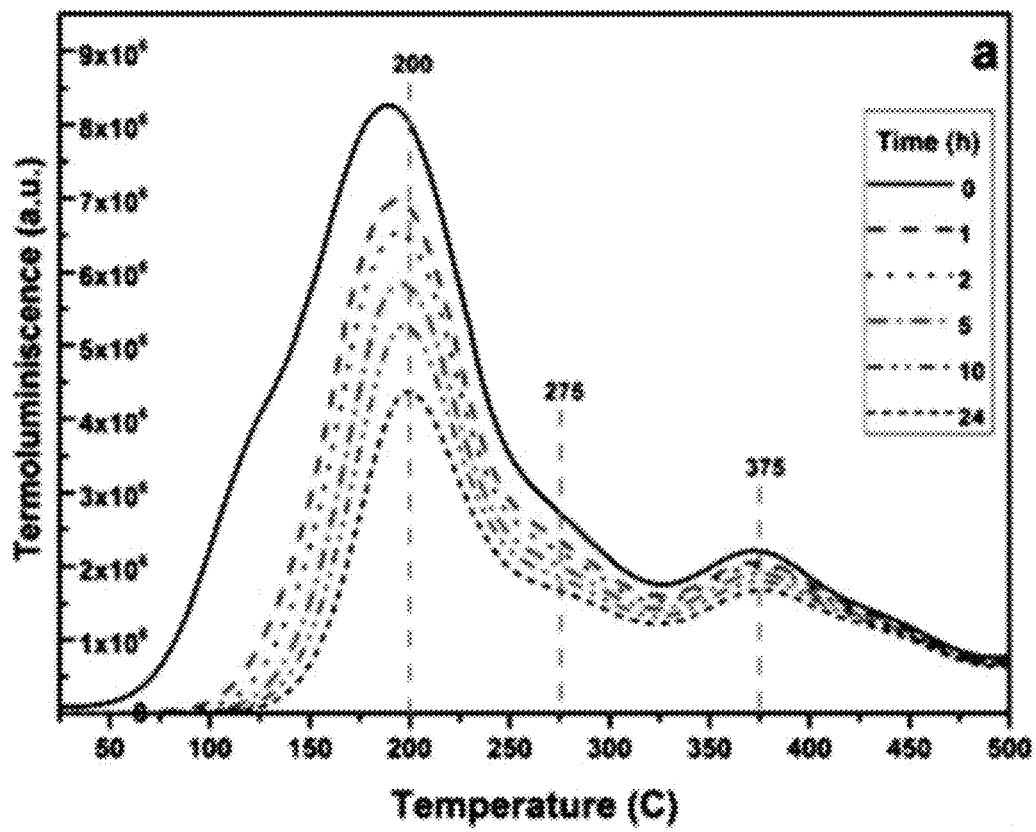
FIGS. 17A-17D. Thermoluminescence (TL) fading curve of YAG nanophosphors doped with 0.5 at. % (FIG. 17A), 1.0 at. % (FIG. 17B), 1.5 at. % (FIG. 17C) and 2.0 at. % (FIG. 17D) of $Pr^{3+}$ in a period of 24 hr. The irradiation dose was 20 Gy.
Figure 17B:
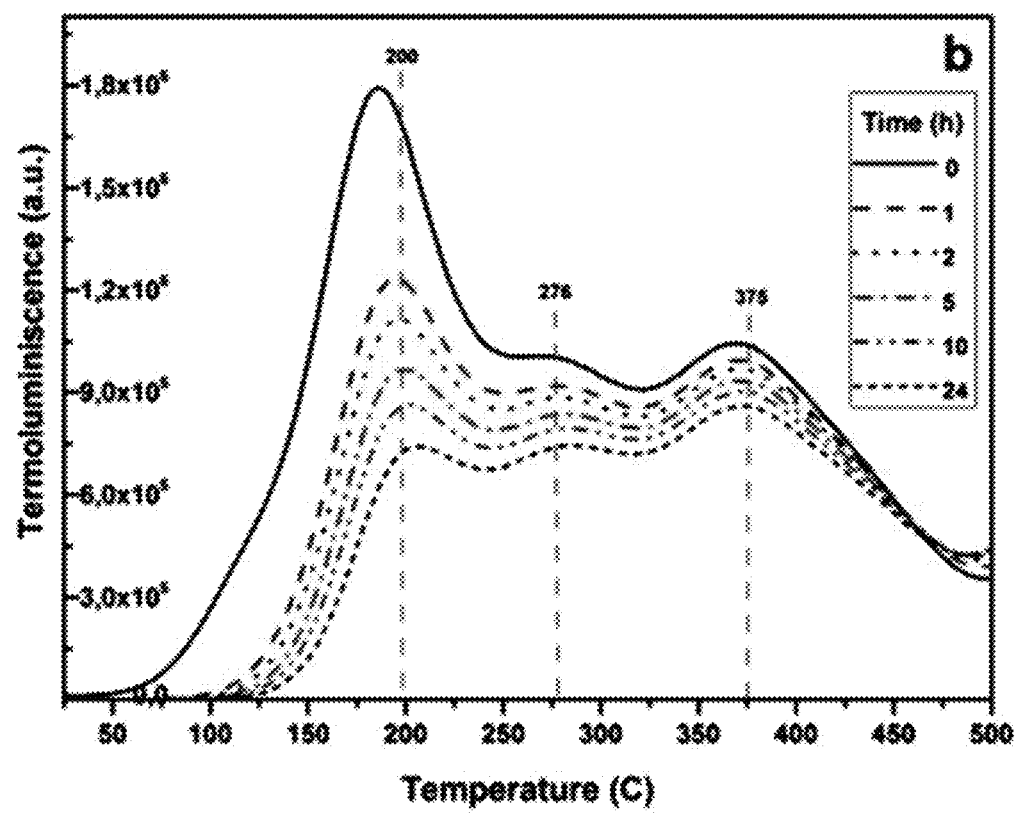
Figure 17C:
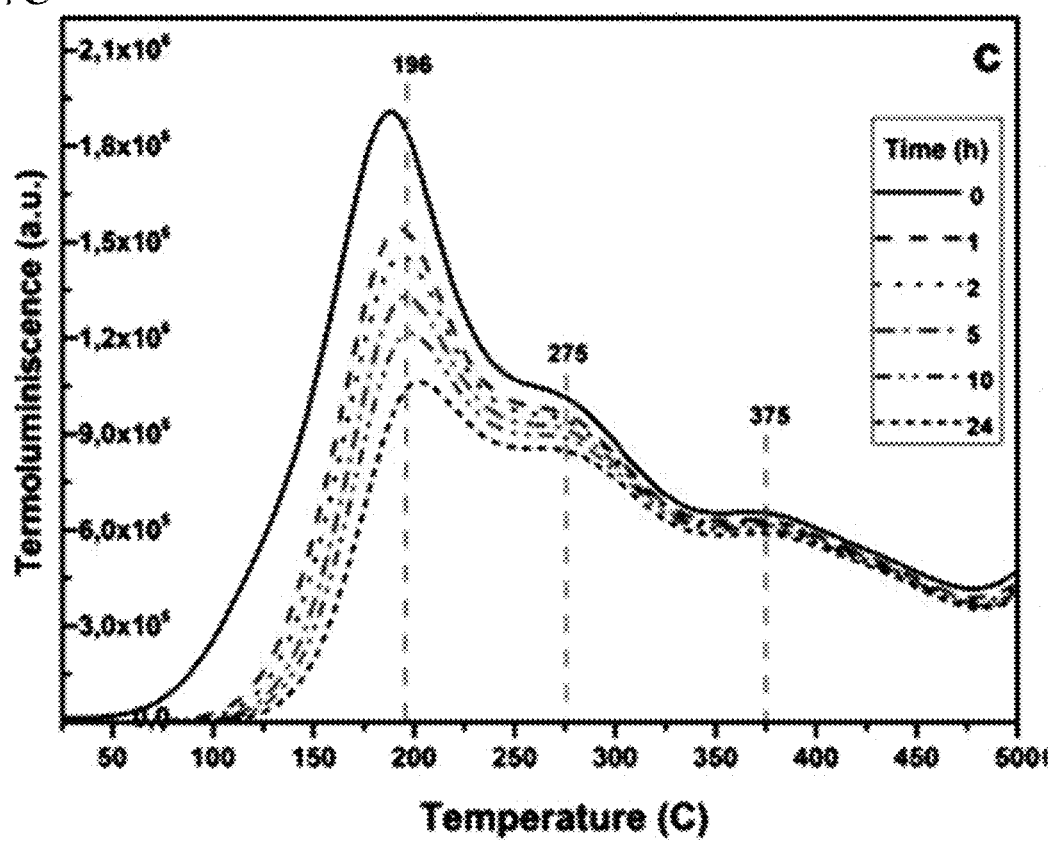
Figure 17D:
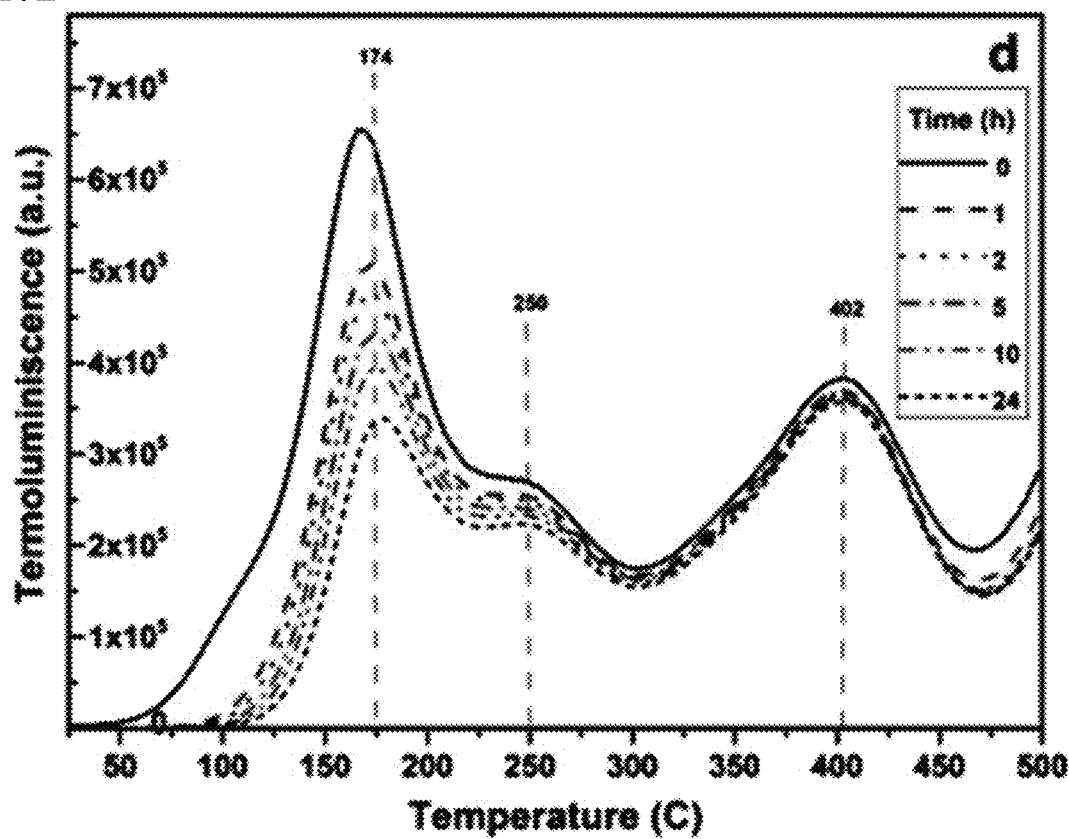

The reported scintillating decay time for LYSO single crystals is of the order of 40 ns [A. J. Wojtowicz, et al., Opt. Mater., 28 (1-2) (2006) 85]. The luminescence lifetime of a phosphor follows an exponential decay [Joseph R. Lakowicz. Principles of Flourescence Spectroscopy, Springer, New York, USA, (1983)], which is represented by the following formula:

$$I=I_o\exp^{-kt}$$

where I is the luminescence emission intensity, $I_o$ is the initial intensity, k is the relaxation rate and t is the decay time [Joseph R. Lakowicz. 1983, Id.]. Room temperature luminescence decay time profiles of the Pr-doped emission monitored at 280 nm upon excitation at 252 nm varied between 10-16 ns as shown in FIGS. 16A-16B. FIG. 16A shows the LYSOP1 sample decay curve corresponding to the emission peak located at 280 nm (FIG. 14). In this case, the decay follows two exponential curves. We assume that the shortest time for sample LYSOP1, is due to a host lattice emission, independent of the activator. FIG. 16B shows the decay curves of samples LYSOP2 and LYSOP3. Both decay curves were fitted only to one exponential curve, so we assume that there is no presence of emission by the host lattice in none of the two samples. The measurement corresponds to the peak located at 275 nm (LYSOP2 sample) and 277 nm (LYSOP3 sample) shown in FIG. 14. Table 3 summarizes the calculated decay times for the set of samples. PET detectors have to work at high count-rates, so it is important that the decay time of the scintillator should be short (less than 40 ns) [C. Ronda, et al., Mater. Res. Soc. Symp. Proc. 1111 (2009) 1111-D08-01]. Decay time of LYSO single crystals can be modified by varying the Y, for higher Y concentrations, scintillating times are longer, but when the concentrations vary between 5-10%, there is no difference in the decay time [M. Nikl, et al., IEEE Trans Nucl Sci. 55 (3) (2008) 1035]. In this study, the sample with the largest concentration of Y and the smaller $Pr^{3+}$ concentration (sample LYSOP3) yields the shortest decay time. The resulting decay time values in this study contrast with the previously decay time values reported for Ce-activated LYSO singles crystals [M. Nikl, et al., IEEE Trans Nucl Sci. 55 (3) (2008) 1035], Ce-activated LYSO powders [C. W. E. Van Eijk, et al., 1994, Id.] or even Pr-activated LSO single crystals [M. Nikl, et al., Journal of Crystal Growth. 292 (2) (2006) 416], but a detailed experiment must be performed in order to clarify the $(Lu_{1-\alpha-\beta}Y_\alpha Pr_\beta)_2SiO_5$ materials behavior.

CONCLUSION

UV emitting $(Lu_{1-\alpha-\beta}Y_\alpha Pr_\beta)_2SiO_5$ (0.1≤α≤0.4, β=0.05, 0.005) powders were successfully synthesized by the combustion synthesis method. The $Pr^{3+}$ was well incorporated into the $(Lu,Y)_2SiO_5$ host lattice as confirmed by X-ray diffraction analysis. Transmission electron microscopy revealed the formation of bar-type crystals of 0.6 μm length. Photoluminescence measurements ($\lambda_{exc}$=250 nm) showed a very bright UV-emission composed of two wide peaks with maximum emissions centered at λ=280 nm and λ=315 nm, both corresponding to the $Pr^{3+}$ forbidden transitions $^5D_2$→4f ($^3P_2$) and $^5D_1$→4 f ($^3H_4$), respectively. Moreover, these powders produce luminescence decay times in the range of 10-16 ns, with the shortest decay time for the sample with the smallest $Pr^{3+}$ concentration. The application of $(Lu_{1-\alpha-\beta}Y_\alpha Pr_\beta)_2SiO_5$ powders as suitable PET components is not verified yet. In future investigations will be necessary to make a radioluminescence analysis to observe their behavior under high-energy excitation.

Example 2. Thermoluminescence and Afterglow Low Dose β Dosimetry Based on Nanocrystalline YAG-$Pr^{3+}$ Produced by Combustion Synthesis Abstract. In this work thermoluminescence (TL) and afterglow (AG) properties of Pr-doped $Y_3Al_5O_{12}$ (YAG-$Pr^{3+}$) nanocrystalline phosphors (30.0 nm) produced by combustion synthesis method were investigated for dosimetric and medical applications. The TL and AG results suggest that $Pr^{3+}$-doped $Y_3Al_5O_{12}$ (YAG-$Pr^{3+}$) nanocrystalline phosphor is an excellent candidate for β irradiation medical dosimeter applications in the range of 0-20 Gy. Both thermoluminescence and afterglow properties were optimal with 0.5% $Pr^{+3}$. Following irradiation AG and TL dosimetry were performed for 0-5 hrs, and more than 5 hrs, respectively. Fluorescence was linear for radiation doses of 0-20 Gy, with no apparent saturation up to 200 Gy.

INTRODUCTION

Materials exhibiting thermoluminescence (TL) and afterglow (AG) properties in response to ionizing radiation are very important as detectors in dosimetric and potentially other medical applications such as photodynamic therapy [Azorin, J., et al., Phys. Stat. Sol. A 138 (1993) 9-46; Bos, A. J., Radiat. Meas., 33 (2001) 737-744; Bos, A. J., Radiat. Meas., 41 (2006) S45-S56]. TL dosimetric materials should possess a wide linearity range with absorbed dose, high sensitivity, low fading, radioresistance, and they should be chemically inert [McKeever, S. W. S., et al., 1995, Thermoluminescence Dosimetry Materials: Properties and Uses, Nuclear Technology Publishing, Ashford, UK]. In the last few years the search for improved thermoluminscent materials has resulted in the characterization of various crystalline oxide rare earth activated materials. Promising candidates include $Lu_2SiO_5$(LSO) and $Y_2SiO_5$ [Zorenko, Y., et al., Opt. Mater., 34 (2012) 1969-1974.], lutetium aluminate perovskite $LuAlO_3$, lutetium yttrium orthosilicate (LYSO) and yttrium aluminum garnet (YAG) [Wojtowicz, A. J., et al., J., Opt. Mater., 28 (2006) 85-93], Interesting luminescence properties have been reported for nanophosphor hosts activated with rare earth ions notably of the garnet group [Speghini, A., et al., Opt. Mater., 33 (2011) 247-257]. The garnet group has the general formula of $X_3Y_2(SiO_4)_3$ where the X site is usually occupied by divalent cations ($Ca^{2+}$, $Mg^{2+}$, $Fe^{2+}$) and the Y site by trivalent cations ($Al^{3+}$, $Fe^{3+}$, $Cr^{3+}$, $Pr^{3+}$) in an octahedral/tetrahedral frame with $(SiO_4)_4$ occupying the tetrahedral. The best garnet candidate for luminescent material is YAG, which provides unique optical properties when doped with trivalent lanthanide ions [Speghini, A., et al., 2011, Id.]. These $Y_3Al_5O_{12}$ (YAG) oxyorthosilicate materials in nanocrystalline form have been studied for thermoluminescent dosimetry (TLD) of ionizing radiation [Zhydachevskii, Ya., et al., Radiat. Meas., 45 (2010) 516-518; Zhydachevskii, Y., et al., Radiat. Meas., 46 (2011) 494-497; Jayaramaiah, J. R., et al., Mater. Chem. Phys., 130 (2011) 175-178; Premkumar, H. B., et al., Spectrochim. Acta, Part A. 96 (2012) 154-162] because they are excellent hosts with high thermal stability [Antic-Fidancev, E., et al., Alloys Compd., 341 (2002). 82-86], high effective atomic number ($Z_{eff}$31.4), high sensitivity and linear response in the dose range $1\times10^{-4}$ to $1\times10^3$ Gy [Zhydachevskii, A. et al., Radiat. Meas., 42 (2007) 625-627]. Praseodymium ($Pr^{3+}$) impurities in yttrium-based compounds are particularly interesting as $Pr^{3+}$ ions occupy several different sites in the complex yttrium dodecahedral lattice [Gruber, J. B., et al., No. HDL-TR-2171, HARRY DIAMOND LABS ADELPHI MD. (1989)].

Recently, luminescent properties of 58 nm YAG-$Pr^{3+}$ crystals were reported together with a model explaining the differences between nano and crystalline forms of YAG-$Pr^{3+}$ [Ozen, G., et al., 2013, Id.]. Moreover, R. A. Rodriguez et al., studied the thermoluminescence (TL) and luminescence of YAG: $Er^{3+}$,$Yb^{3+}$ under high β radiation doses, and found that the introduction of impurities modifies the crystal structure and therefore localized trapping states [Rodriguez, R. A., et al., Opt. Mater., 27 (2004) 293-299]. However, a mechanism for explaining luminescence relaxation is still needed, and accordingly, Yukihara and co-workers [Yukihara, E. G., et al., J. Lumin., 133 (2013) 203-210] have proposed a phenomenological model of energy levels for luminescent recombination to explain thermometry properties of YAG-$Pr^{3+}$. Nonetheless, dosimetric properties for low dose radiation and for medical applications, particularly TL and AG, of YAG-$Pr^{3+}$ nanopowder remained to be addressed both experimentally and theoretically.

Here we analyzed TL and AG dosimetric properties of Pr-doped YAG nanophosphers synthesized by the combustion method at with $Pr^{3+}$ at 0.5, 1.0, 1.5 and 2.0%. In the context of both TL and AG applications, we found that 0.5% $Pr^{3+}$ doping concentration provided the best combination of sensitivity, thermoluminscence output, and afterglow properties. The present data support further exploration of YAG nanophosphors for dosimetric and nanomedical applications.

Experimental

Synthesis of YAG-$Pr^{3+}$ by Combustion Method

Nanocrystalline phosphors of Pr-doped $Y_3Al_5O_{12}$ (YAG-$Pr^{3+}$) were produced by combustion synthesis [Lopez, O. A., et al., J. Lumin., 71 (1997) 1-12]. The starting materials for the synthesis were aluminum nitrate [Alfa Æ Eesar Al(NO_3)_3.6H_2O 99.99%], yttrium nitrate [Alfa Æ Eesar Y(NO_3)_3.6H_2O 99.99%] and praseodymium nitrate [Alfa Æ Eesar Pr(NO_3)_3.6H_2O 99.99%] as precursors that were dissolved in 30 ml of deionized water in a quartz beaker, and then carbohydrazide [$CH_6N_4O$, Alfa Æ Eesar 98%] was added as a reductive fuel forming a homogeneous solution. The chemical precursors were adjusted in order to obtain $(Y_{1-x}Pr_x)_3Al_5O_{12}$ with different $Pr^{3+}$ concentration of x=0.5, 1.0, 1.5 or 2.0 at. %. Quartz beakers containing mixtures with different $Pr^{3+}$ concentrations were individually placed into a pre-heated oven (~530° C.) in order to induce the reaction. After 3-5 minutes the reaction takes place and a white foamy product is obtained which is finely crushed with mortar and pestle prior to post-annealing treatment at 1200° C. for 2 hours. It has been found that heat treatments are crucial in order to enhance luminescence. Additional details with a description of the reaction and procedure for producing these phosphors are described in Bosze et al. [Bosze, E. J., et al., Mater. Sci. Eng. A, 97 (2003) 265-274; Bosze, E. J., et al., J. Am. Ceram. Soc., 90 (2007) 2484-2488].

Characterization.

X-ray diffraction (XRD) analysis of the powders were performed in a Phillips X'Pert diffractometer equipped with $CuK_\alpha$ radiation ($\lambda$=0.15406 nm). Measurements in a 2θ=15-80° range were taken with a step size of 0.02° and a 1 sec dwell per point. Transmission electron microscopy (TEM) images were obtained with a JEOL-2010 operated at 200 kV accelerating voltage. Photoluminescence (PL) spectra were collected with a fluorescence spectrophotometer (Hitachi FL-4500). All measurements were performed at room temperature (RT).

Thermoluminescence and Afterglow Measurements.

The TL and AG experiments and β-irradiation (Sr-90, 40 mCi, 0.1 Gy/s in quartz) were performed in a Risø TL/OSL reader (model TL/OSL DA-20). The AG decay curves were recorded at RT, the heating rate of the TL readouts was 5 K/s, in the temperature range from RT to 350° C. The pellets of 5 mm diameter, 1 mm of thickness and 100 mg used in AG and TL experiments were prepared with powder and exposed to β irradiation.

Results and Discussion.

X-Ray Powder Diffraction.

FIG. 7 shows a typical XRD pattern corresponding to the $Pr^{3+}$ doped $Y_3Al_5O_{12}$ nanocrystalline samples produced by combustion synthesis and post-annealed at 1200° C. for 2 hr. This XRD pattern is similar to that reported in the literature for the YAG crystalline structure [Hess, N. J., et al., J. Mater. Sci., 29 (1994) 1873-1878]. Similar XRD patterns were obtained for all praseodymium concentrations used in the present investigation.

Crystal Structure of YAG-$Pr^{3+}$.

In FIG. 8, a representative TEM (same sample as in FIG. 7) of the 1.0 at. % $Pr^{3+}$-doped nanophosphor is shown. Morphology of this sample reveals a large number of irregular nanocrystallites of sizes in the range of 5.0-50.0 nm, with the most frequent particle size of around 30.0 nm, which confirms this phosphor powder as nanocrystalline material. Some porosity is observed which increases the amount of grain surface area, which may be related to the enhancement in luminescence intensity.

Photoluminescence Property.

Photoluminescence measurements were also performed for the YAG-$Pr^{3+}$ nanophosphors. We found an optimum excitation wavelength at $\lambda_{Exc}$=292 nm for all different concentrations of $Pr^{3+}$. FIG. 10 illustrates the photoluminescence characteristics for three different concentrations of $Pr^{3+}$ in the YAG host lattice. It can be observed that the maximum PL emission occurs in the sample doped with 1.0 at. % $Pr^{3+}$. This UV emission centered at $\lambda$=320 nm can be ascribed to $^5D_1\rightarrow^3P_2$ transition, and a much lower PL contribution due to $^5D_1\rightarrow^3H_4$ electronic transitions within the praseodymium ion is also detected at $\lambda$=490 nm [Kolesov R., et al., Nat. Comm., 3 (2012) 1029-1036].

Thermoluminescence (TL) Measurements.

The TL fading for YAG nanophosphors with 0.5, 1.0, 1.5 and 2.0 at. % concentrations of $Pr^{3+}$ after 1, 2, 5, 10 and 24 hours are shown in FIGS. 17A-17D, respectively. For all samples, TL intensity is inversely proportional to $Pr^{3+}$ concentration. TL glow curves in YAG-$Pr^{3+}$ consist of three broad peaks at approximately 200, 275 and 375° C. It is observed that the 200° C. peak decreases significantly with time whereas the peak at 375° C. remains more stable. This behavior may be ascribed to shallow traps generated by spurious contaminants and high frequency factors for releasing electrons from these traps. In general, thermoluminescent glow curves are composed for both different trapping states and depths corresponding to $Pr^{3+}$ dopant defect centers with different structure position, created during the ionizing radiation stage. In this case, TL fading behavior is mainly due to the higher temperature (375° C.) peak. At this point, it is important to note that similar results consisting in four peaks at 170, 210, 256 and 332° C. (main peak), were reported by the deconvolution of the TL glow signal in nanocrystalline YAG by R. A. Rodriguez and collaborators [Rodriguez, R. A., et al., J. Phys. D: Appl. Phys, 38 (2005) 3854], where they related this TL behavior with the presence of stronger major contents of defects in comparison with single YAG.

As discussed by E. D. Milliken and collaborators [Milliken, E. D., et al., 2012, *J. Lumin.*, 132: 2495-2504]. trivalent lanthanides like $Pr^{3+}$ are likely to act as hole traps that are stable at room temperature because their electronic levels are well above the top of the valence band (2.06 eV). Such defects can capture a hole from the valence band:

$$h_+ + Pr^{3+} \rightarrow Pr^{4+} \quad\quad 1$$

If the trapped hole subsequently captures an electron from the conduction band, emission from this cation will be observed $$e_- + Pr^{3+} \rightarrow (Pr^{3+})^* + h\nu \quad\quad 2$$

They found that the excitation band of the transition 4f ground state to 5d2 level of YAG-$Pr^{3+}$ present peaks of energy estimated to 2.06 eV as the energy difference between $Pr^{3+}$ ground state and the top of the valence band [Milliken, E. D., et al., 2012, Id.].

Figure 18:
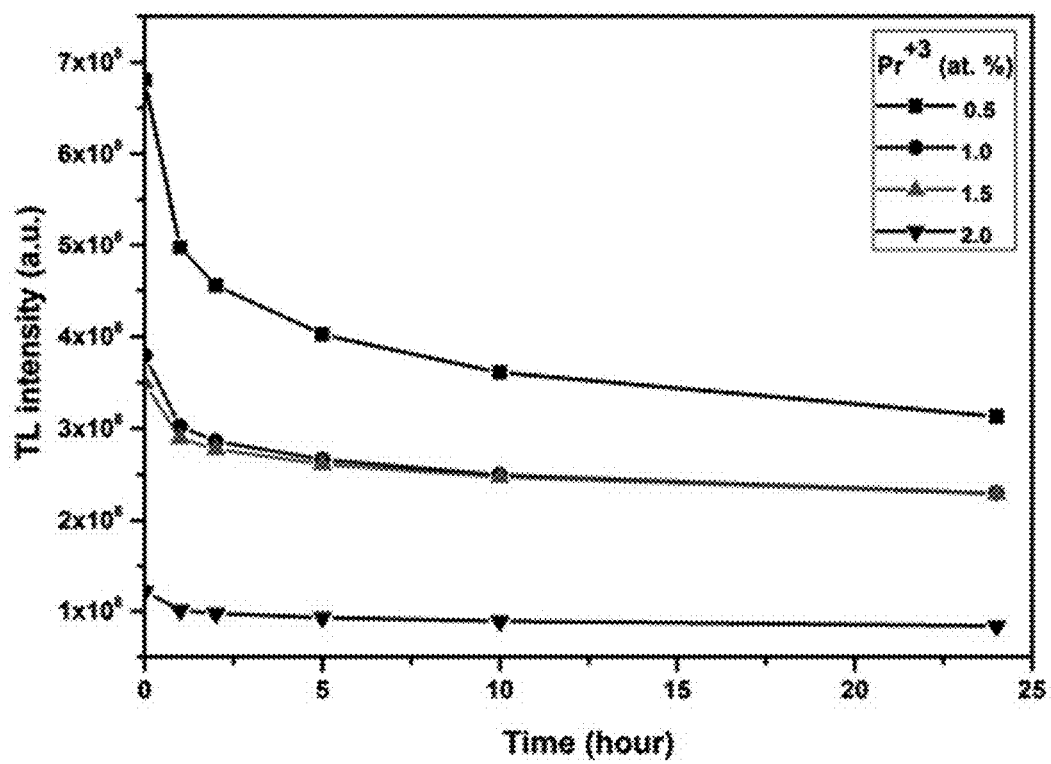
FIG. 18. Thermoluminescence fading of YAG-$Pr^{3+}$ nanophosphors irradiated with β-dose of 1 Gy as a function of time (hr). Legend: $Pr^{+3}$ (at. %): 0.5 (filled box); 1.0 (filled circle); 1.5 (triangle tip up); 2.0 (triangle tip down).

The $Pr^{3+}$ concentration response of β irradiated (20 Gy) YAG samples was investigated by plotting the integrated TL signal as function of time after exposure and is shown in FIG. 18. According to this, we have found that TL of YAG-$Pr^{3+}$ nanophosphors is stable after five hours for all $Pr^{3+}$ concentrations. Moreover, it can be observed that the strongest fading signal is associated with 0.5 at. % $Pr^{3+}$ and, as described before, TL intensity decreases as $Pr^{3+}$ concentration increases.

Figure 19:
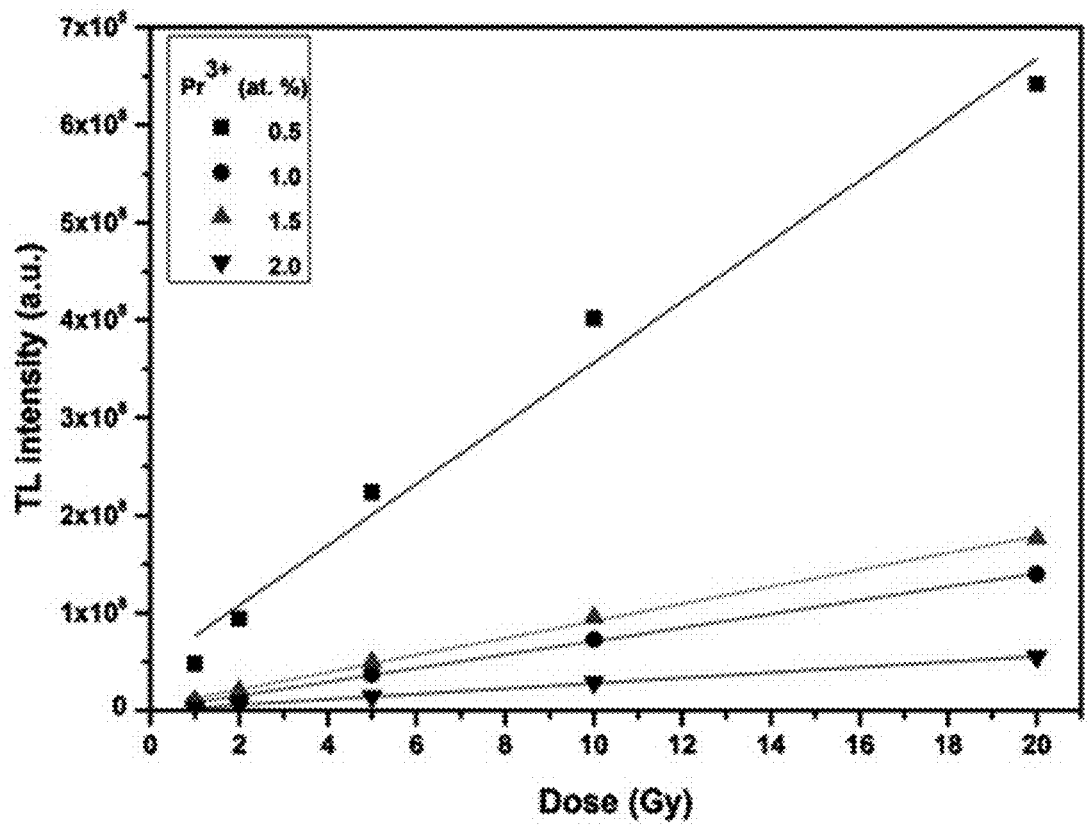
FIG. 19. Thermoluminescence beta dosimetry of YAG-$Pr^{3+}$ in the range of 0-20 Gy. Legend: see FIG. 18.
Figure 20A:
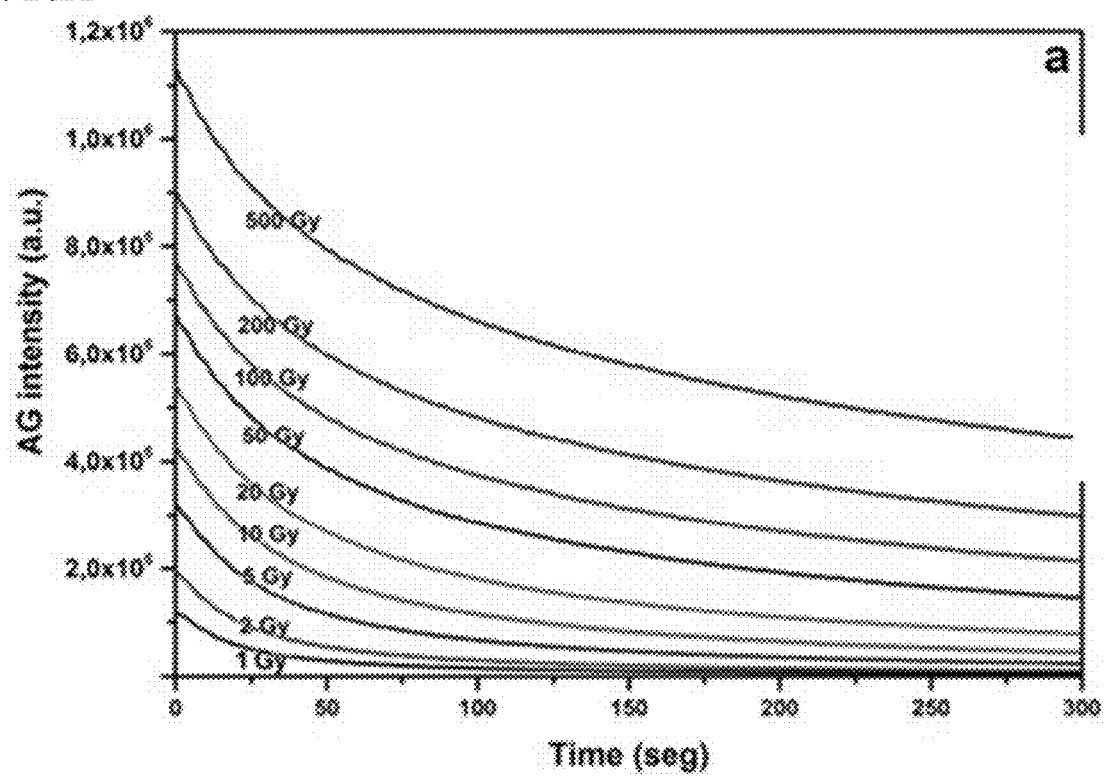
FIGS. 20A-20D. Typical afterglow curves in the range of 1 to 500 Gy for all $Pr^{3+}$ concentrations.
Figure 20B:
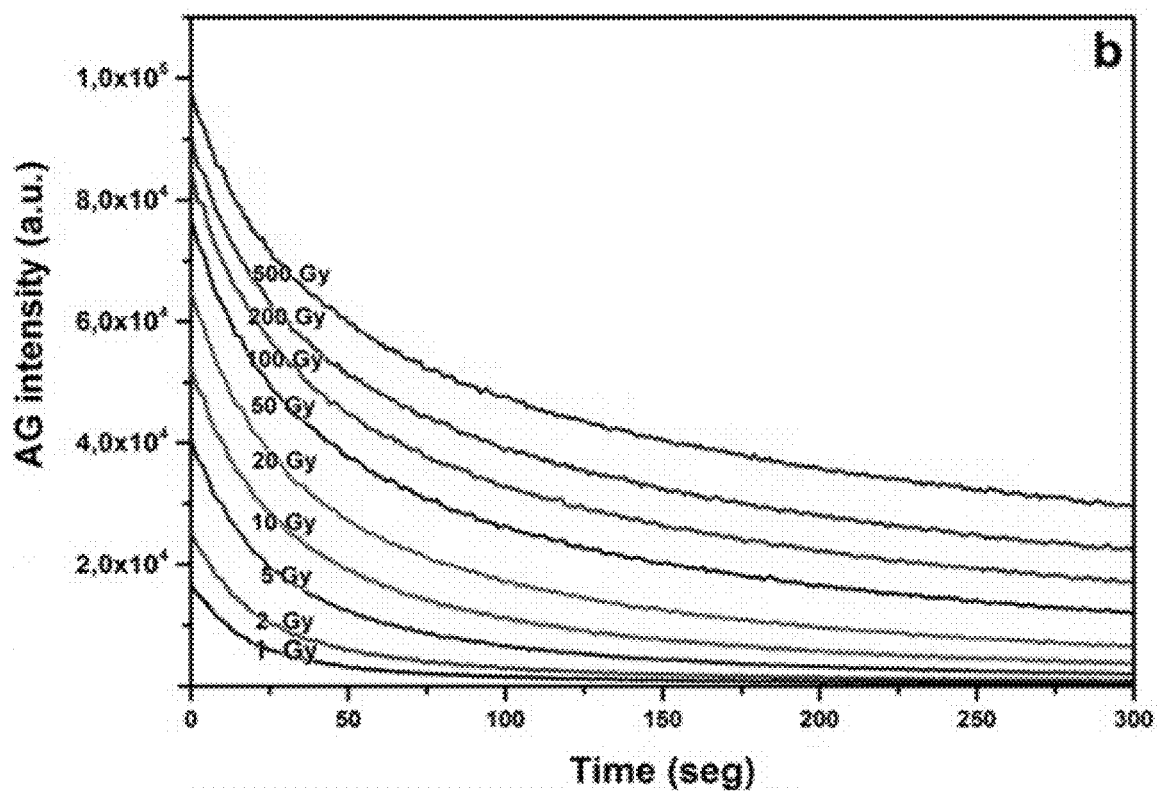
Figure 20C:
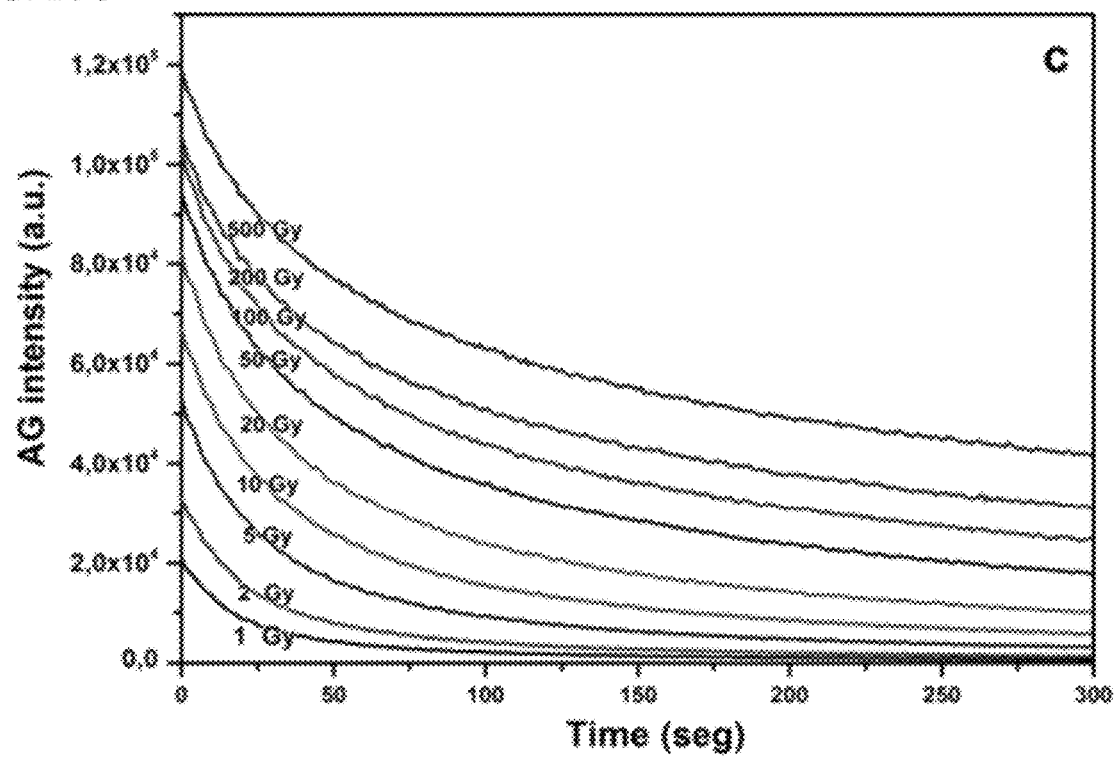
Figure 20D:
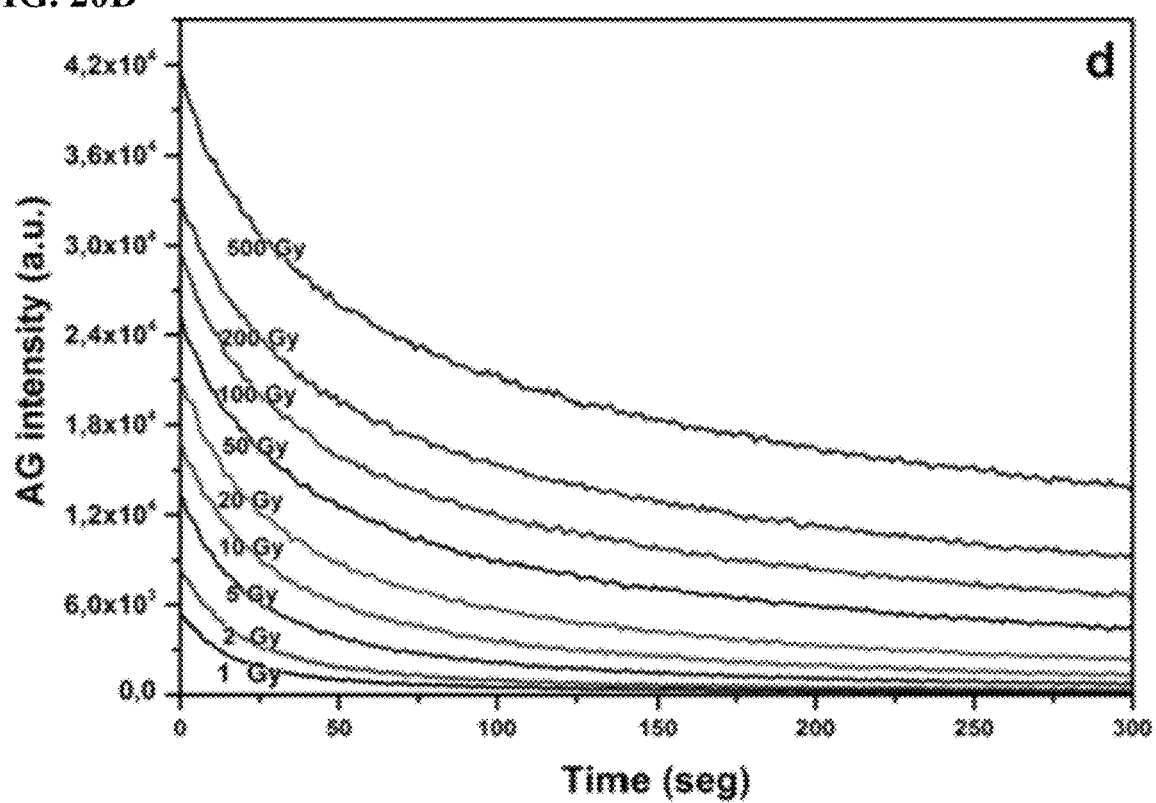

For medical applications we found that YAG-$Pr^{3+}$ showed strong linear TL intensity behavior with doses of β irradiation up to 20 Gy. No apparent TL saturation was observed for 200 Gy but a superlinear response at high doses for all samples. Also, we confirmed that 0.5 at. % $Pr^{3+}$ is most intense for all doses, see FIG. 19. This linear response and low fading makes YAG-$Pr^{3+}$ a good candidate for TL dosimetry.

Afterglow (AG) Curves.

An alternative form to achieve β doses immediately after irradiating tissues in medicine is known as AG decay. In FIGS. 20A-20D the AG decay curves of YAG nanophosphor with four different concentration of $Pr^{3+}$ as a function of the β irradiation dose are compared. This AG corresponds to samples irradiated at 1, 2, 5, 10, 20, 50, 100, 200 and 500 Gy.

For all the samples, it can be observed that intensity increases as the dose increases, as observed in TL behavior. However, opposite to the TL, no saturation was found even to high doses of 500 Gy.

Figure 21:
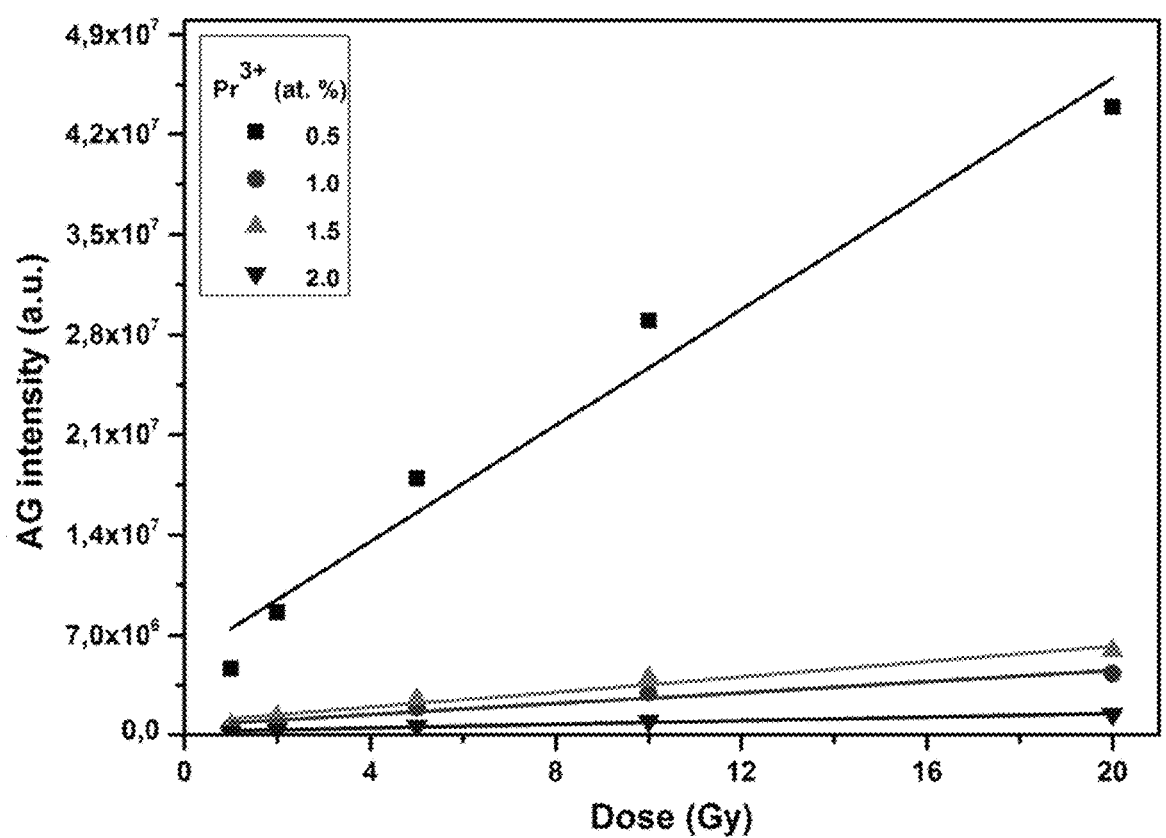
FIG. 21. Afterglow intensity for several $Pr^{3+}$ concentrations. Legend: see FIG. 18.

Also, YAG-$Pr^{3+}$0.5 at. % has the best linear response of AG intensity vs dose, and it is possible to detect low doses as 20 Gy (FIG. 21). It is important to note that although YAG-$Pr^{3+}$2.0 at. % shows the lowest AG response, this sample depicted the highest linearity range, up to 200 Gy.

CONCLUSION

We found that combustion synthesis produces nanocrystalline YAG-$Pr^{3+}$ in the 5-50 nm diameter range. $Pr^{3+}$ is incorporated substitutionally in Y garnet positions as confirmed by XRD and TEM measurements. YAG-$Pr^{3+}$ exhibits an intense TL and AG signal, which is useful for TL-based dosimetry to achieve retrospective doses and for AG dosimetry to determine real time doses. Our results show that samples of YAG-$Pr^{3+}$ incorporating 0.5% of $Pr^{3+}$ during crystal growth are the most optimal for both TL and AG dosimetric approaches. The results support further investigation of YAG-$Pr^{3+}$ nanocrystals for dosimetric and biomedical applications.

Example 3. Photo Emission Properties of Doped Nanocrystals

Photon Emission Per MeV.

The radioluminescence emission properties of the nanoscintillator crystals tabulated in Table 4 following were assayed using methods known in the art. See e.g., Jung, J. Y., et al., *J. Luminescence* 2014, 154:569-577. The term "Act." refers to "activator."

TABLE 4

Photon emission per MeV of X-rays and emission peak wavelength(s)

| Composition | Act. | Luminosity (photons/MeV) | Emission peak (nm) 1 | Emission peak (nm) 2 |
|---|---|---|---|---|
| GdOCl:Ce | $Ce^{3+}$ | 75% of ZnS:Ag | 365 | 410 |
| YOCl:Ce | $Ce^{3+}$ | 52% of ZnS:Ag | 365 | 405 |
| LaBr$_3$:Ce | $Ce^{3+}$ | 74,000 | 375 | |
| CeBr$_3$ | | 68,000 | 371 | |
| LaBr$_3$:Ce | $Ce^{3+}$ | 61,000 | 356 | 387 |
| K$_2$LaCl$_5$:Ce | $Ce^{3+}$ | 49,300 | 347 | 372 |
| LaCl3:Ce | $Ce^{3+}$ | 48,000 | 350 | |
| CeCl3 | $Ce^{3+}$ | 46,000 | 350 | |
| K2LaBr5:Ce | $Ce^{3+}$ | 40,000 | 359 | 391 |
| NaGdCl4:Ce | $Ce^{3+}$ | 39,400 | 350 | 370 |
| GdCl3:Ce | $Ce^{3+}$ | 38,000 | 350 | 370 |
| BaGdCl5:Ce | $Ce^{3+}$ | 35,000 | 363 | 389 |
| Gd2Si2O7:Ce (GPS) | $Ce^{3+}$ | 35,000 | 372 | 394 |
| Rb2LiLaBr6:Ce | $Ce^{3+}$ | 33,000 | 363 | 387 |
| Ba2GdCl7:Ce | $Ce^{3+}$ | 30,000 | 355 | 227 |
| K2CeCl5 | | 30,000 | 370 | |
| Lu2Si2O7:Ce (LPS) | $Ce^{3+}$ | 26,000 | 378 | |
| Cs2NaCeBr6 | $Ce^{3+}$ | 25,000 | 377 | 400 |
| Rb2LiCeCl6 | $Ce^{3+}$ | 23,100 | 370 | |
| Lu2Si2O7:Ce (LPS) | $Ce^{3+}$ | 23,000 | 380 | |
| Cs2LiYCl6:Ce (CLYC) | $Ce^{3+}$ | 21,600 | 370 | |
| PrBr3:Ce | $Ce^{3+}$ | 21,000 | 365 | 395 |
| LuAlO3:Ce | $Ce^{3+}$ | 20,500 | 365 | |
| YAlO3:Ce (YAP) | $Ce^{3+}$ | 20,100 | 365 | |
| Cs2LiYCl6:Ce | $Ce^{3+}$ | 18,400 | 372 | 400 |
| LuPO4:Ce | $Ce^{3+}$ | 17,200 | 360 | |
| CeCl3(CH3OH)4 | $Ce^{3+}$ | 16,600 | 364 | |
| YAlO3:Ce (YAP) | $Ce^{3+}$ | 16,200 | 347 | |
| Y2O3 | SX | 15,480 | 370 | |
| LuAlO3:Ce | $Ce^{3+}$ | 11,400 | 365 | |
| BaBr2:Ce | $Ce^{3+}$ | 10,300 | 370 | 370 |

TABLE 4-continued

Photon emission per MeV of X-rays and emission peak wavelength(s)

| Composition | Act. | Luminosity (photons/MeV) | Emission peak (nm) 1 | Emission peak (nm) 2 |
|---|---|---|---|---|
| KYP2O7:Ce | $Ce^{3+}$ | 10,000 | 380 | |
| Y2O3 | SA | 9,300 | 350 | |
| Y3Al5O12:Pr | $Pr^{3+}$ | 8,000 | 350 | |
| Sc2O3 | SA | 7,700 | 350 | |
| Cs2LiLuCl6:Ce | $Ce^{3+}$ | 7,000 | 370 | 410 |
| Li3YCl6:Ce | $Ce^{3+}$ | 6185 | 360 | 385 |
| NaLuP2O7:Ce | $Ce^{3+}$ | 6,000 | 370 | |
| LuOCl:Ce | $Ce^{3+}$ | 5,500 | 380 | |
| BaCl2:Ce | $Ce^{3+}$ | 5,200 | 349 | 373 |
| LuScBO3:Ce | $Ce^{3+}$ | 4,200 | 370 | |
| YOCl:Ce | $Ce^{3+}$ | 3,500 | 380 | |
| CeBr3+1- | $Ce^{3+}$ | 3218 | 365 | |
| Ca5(PO4)3F:Ce | $Ce^{3+}$ | 3,200 | 354 | 412 |
| CeBr3 +tert-butanol | $Ce^{3+}$ | 3095 | 360 | |
| BaF2:Ce | $Ce^{3+}$ | 2,200 | 360 | |
| CeBr$^{3+}$isobutanol | $Ce^{3+}$ | 1920 | 360 | |
| BaP2O6:Eu | $Eu^{2+}$ | 1,900 | 380 | 470 |
| LaBO3:Ce | $Ce^{3+}$ | 600 | 355 | 380 |
| Ba5(PO4)3F:Ce | $Ce^{3+}$ | 400 | 358 | |
| HfF4 | SA | 300 | 350 | |
| BaF2:Ce | $Ce^{3+}$ | | 350 | |
| LiYSiO4:Bi | $Bi^{3+}$ | | 350 | |
| LaBO3:Bi | $Bi^{3+}$ | | 365 | |

Integrated Intensity (350-370 nm).

Figure 22:
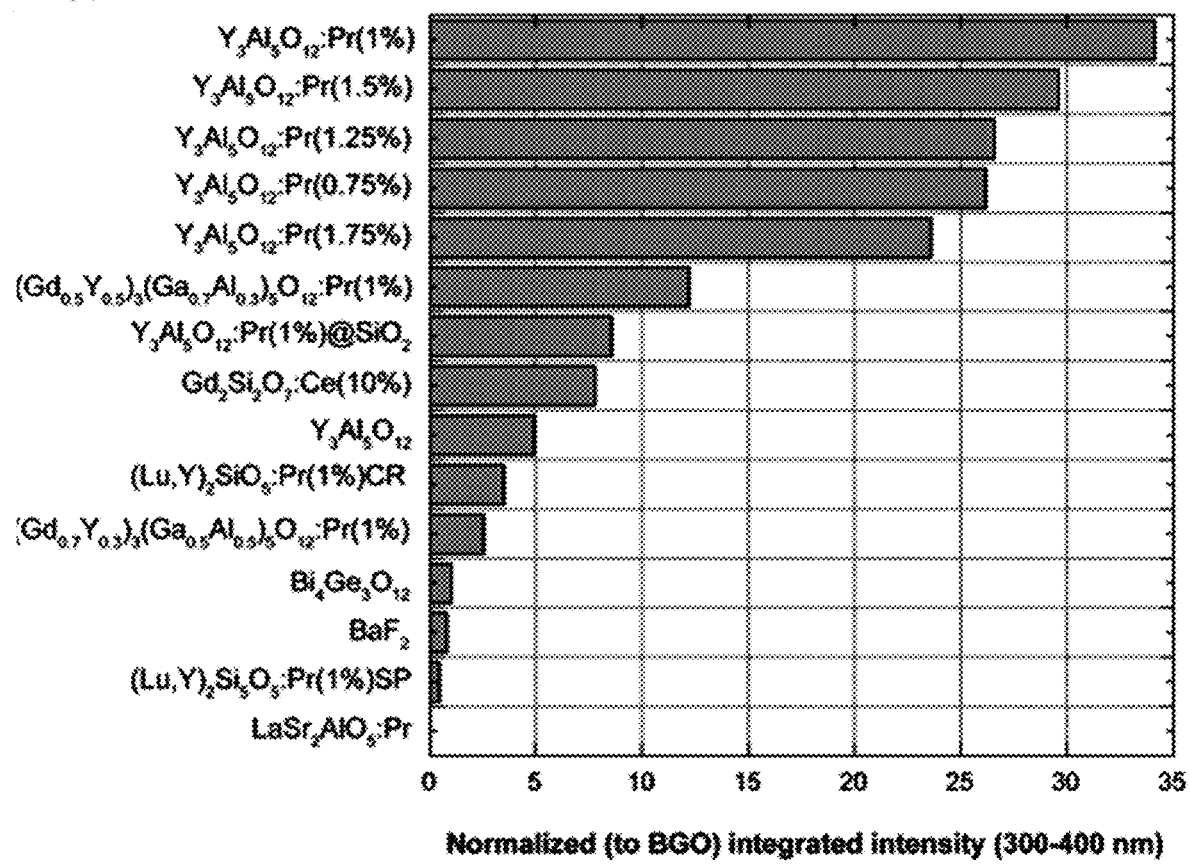
FIG. 22. Integrated radioluminescence emission intensity between 300-400 nm of the nanoscintillators normalized to nanocrystalline $Bi_4Ge_3O_{12}$. CR=combustion reaction, SP=spray pyrolysis. 50 KeV x-rays, short pulse.

The integrated light emission of nanoscintillators that emit in the range 300-400 nm was determined in response to radiation exposure (50 KeV X-rays, short pulse). The results depicted in FIG. 22 demonstrate a significant increase in integrated intensity of YAG-Pr nanoscintillators relative to other indicated samples.

Peak Intensity Versus Emission Wavelength.

Figure 23:
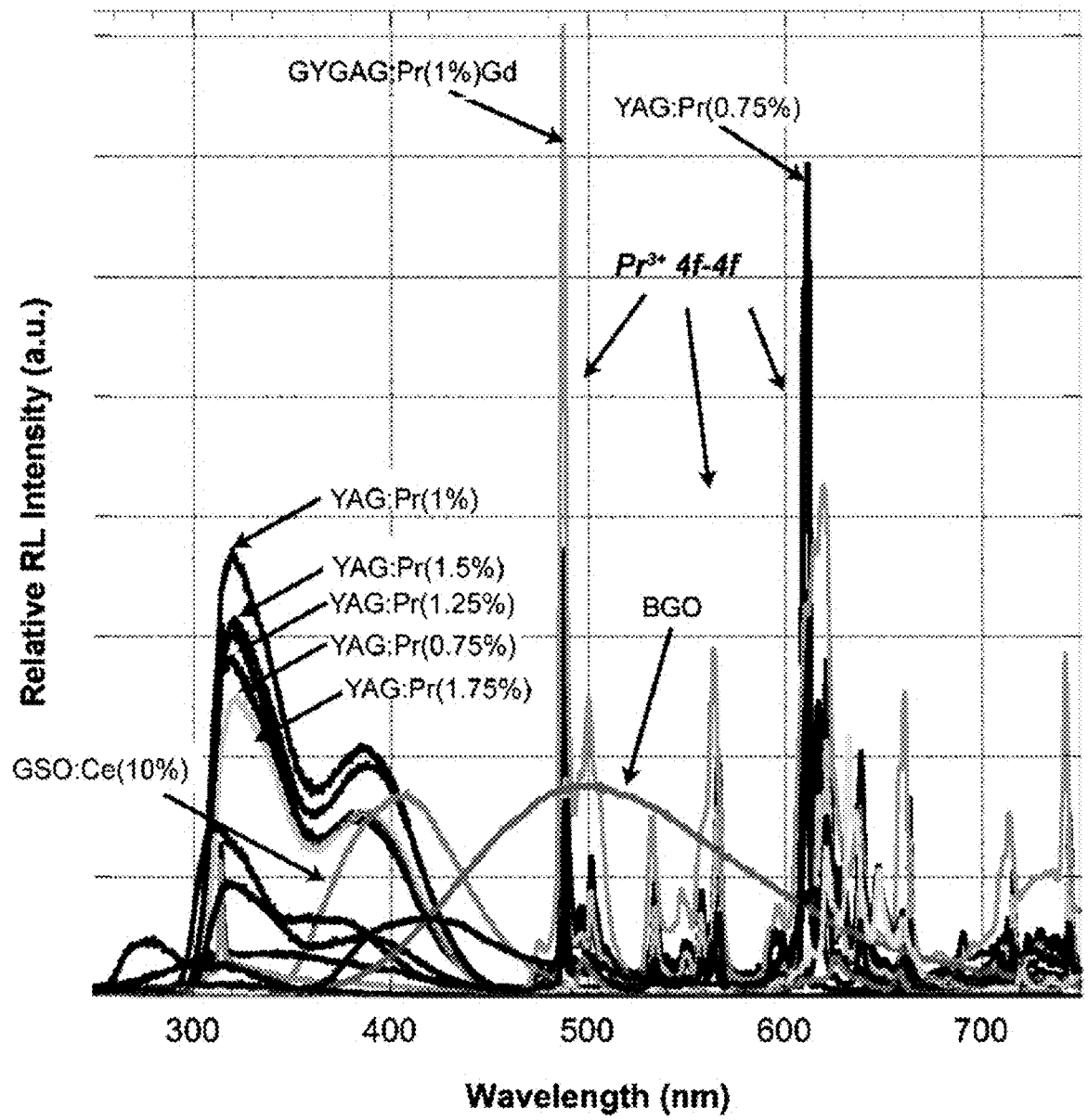
FIG. 23. Radioluminescence spectra emission intensity versus emission wavelength. Peak intensity of emitted light in the range 250-750 nm was determined for the indicated nanoscintillators.

Peak intensity versus wavelength in the range 250-750 nm is depicted in FIG. 23 for the indicated nanoscintillators. See also FIG. 11.

Example 4. Release of Chemical Agent

Figure 24A:
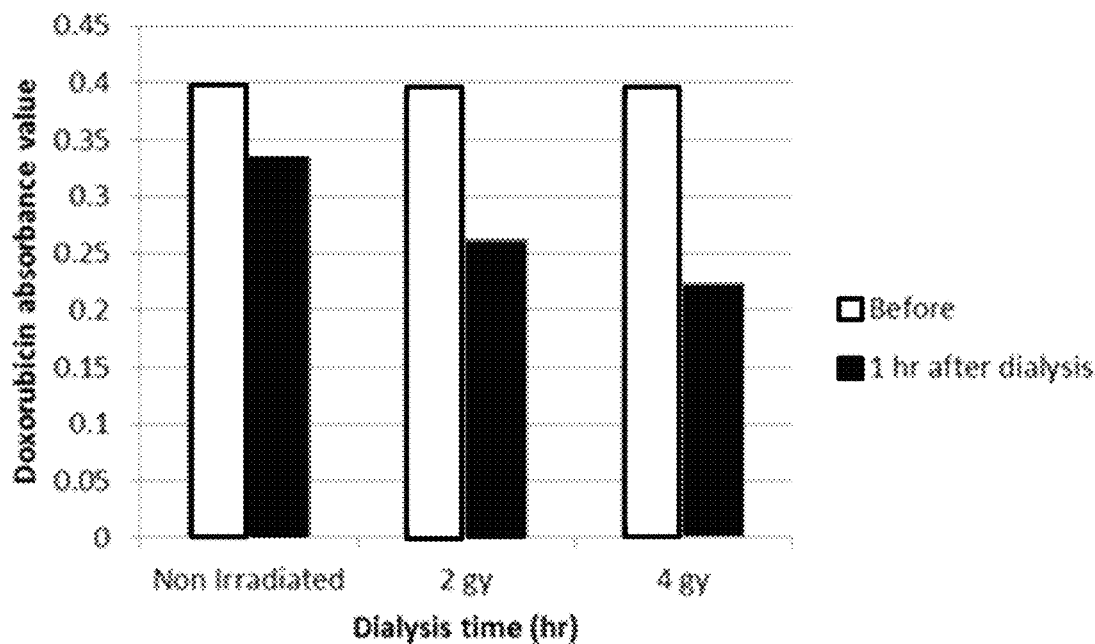
FIGS. 24A-24B. Release of Dox with radiation dose. Dox was attached to a nanoscintillator via a photocleavable linker which was in turn attached to streptavidin which coated the nanocrystal. The system responded to radiation by release of Dox.
Figure 24B:
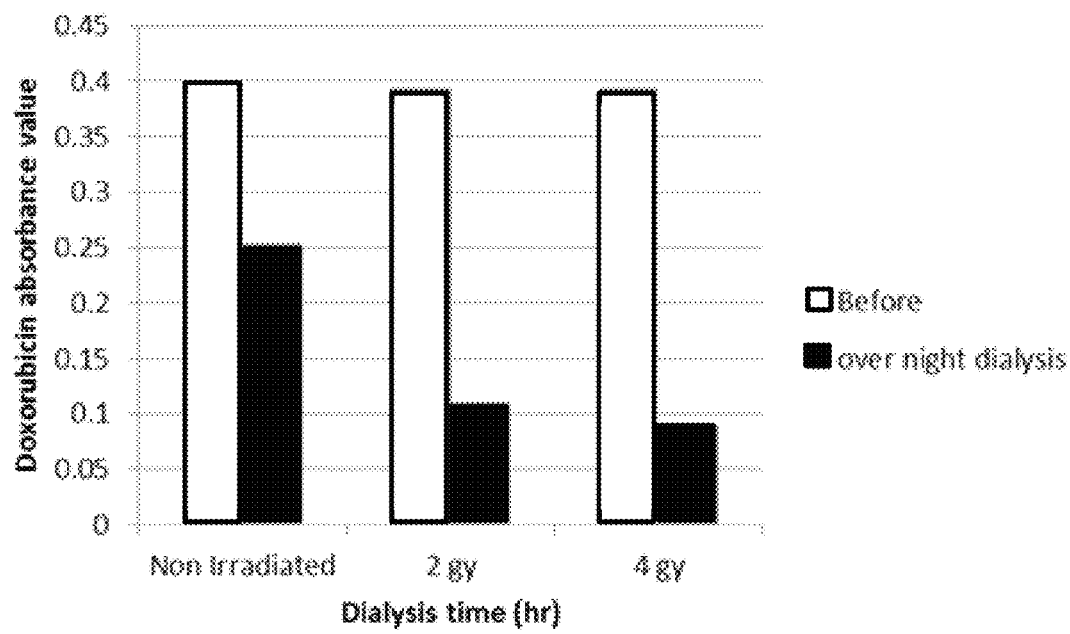

Release of chemical agent, e.g., doxorubicin, can be monitored during dialysis of nanocrystals attached to the chemical agent by methods well known in the art, including e.g., absorption spectroscopy. Doxorubicin was attached to a nanoscintillator (yttrium aluminum crystal doped with praseodymium, YAG-Pr) via a photocleavable linker disclosed herein, which in turn was attached to streptavidin which coated the nanocrystal. Release of doxorubicin was assayed by absorption spectroscopy before and during dialysis as a function of radiation exposure. As depicted in FIG. 24A, at 1-hr after control or radiation exposure (2 Gy or 4 Gy), doxorubicin cleaves from the nanocrystal. The degree of release of doxorubicin correlates with radiation exposure. As depicted in FIG. 24B, after 24-hr dialysis, there is significant cleavage releasing doxorubicin into the dialysis media.

Example 5. Sol-Gel Synthesis of YAG-Pr

Yttrium aluminum garnet ($Y_3Al_5O_{12}$, YAG) doped with praseodymium was synthesized via the sol-gel method. Yttrium acetylacetonate ($Y(C_5H_7O_2)_3$), aluminum acetylacetonate ($Al(C_5H_7O_2)_3$), and praseodymium nitrate ($Pr(NO_3)_3$) were used as precursors. The precursors were mixed with the stoichiometry of Y:Al:Pr=3-x:5:x (x=0.01). Water was slowly added and mixed on a magnetic stirring hot plate at 80° C. until a gel formed. The gel was then calcinated at 700° C. for 3 hours, resulting in the YAG-Pr powder. Previous investigations on sol-gel synthetic methods may be found in Puzyrev, I. S., et al., 2012, *Glass Physics and Chemistry*, 38:427-430. Exemplary methods of sol-gel combustion synthesis of nanocrystalline YAG powers from metal-organic precursors are discussed in Chen, D., et al., 2008, *J. Am. Ceram. Soc.*, 91:2759-2762.

Example 6. Additional Embodiments

Applications of the compositions and methods disclosed herein have great potential in terms of the treatment of cancer, infectious diseases, and industrial applications. For example, a radiation activated prodrug able to significantly improve the management of solid invasive tumors or treat infections with a minimum of side effects would be a highly useful. Another application includes using the disclosed compositions to activate a series of particles carrying different reagents to carry out chemical reactions in machinery or underground pipes or tanks that can be irradiated once enough particles have accumulated. This method could be used to repair or enhance the properties of machinery.

Moreover, the radiation activated prodrug strategy may be useful for a range of solid or diffuse tumors in addition to brain cancer. The nanoparticle prodrug platform when decorated with ligands or antibodies for cell surface receptors may facilitate entry into tumor cells and also traversal of the blood brain barrier. In the latter case while the prodrug would be taken up elsewhere in the body, release of the active drug would only occur in the brain after localized irradiation. Elsewhere the nanoparticle prodrug would clear.

The disclosed methodology is also useful to concentrate antibiotics, in the form of prodrugs, targeted to areas of inflammation/infection. A very low level of localized radiation would be used to liberate the drug(s) creating high local concentrations to overcome bacterial resistance just at the infection site, but the total body dose of the antibiotic would remain low thereby avoiding side effects.

This method may be useful for repairing tubing and conduits. Various components of a cement would be carried to and accumulate at sites needing repair, possibly via an externally applied magnetic field, and local, shaped irradiation would trigger release of cement components in fissures or breaks. This may be particularly useful in corn silos for example, as their internal workings are subject to cracking and they are difficult and costly to repair.

Example 7. Design Considerations

There are disclosed a variety of nanoscintillator compositions useful for the methods disclosed herein. The yttrium-aluminum crystal doped with praseodymium (YAG-Pr) are observed to much more efficiently generate photons in response to radiation than did the barium germanium oxide (BGO) scintillator, $4.5 \times 10^8$ versus $1.5 \times 10^7$, respectively (see e.g., FIG. 22). It is noted that both yttrium and praseodymium in non-soluble form are regarded as essentially non-toxic and yttrium is already used for clinical applications. The YAG-Pr efficiently emitted photons with KeV energy levels of x-rays, to the same extent as would be predicted for MeV levels. Without wishing to be bound by theory, it is believed that this is very positive as it means that low and less damaging energy levels of radiation may be used to activate chemical agents at a desirable site, e.g., anticancer prodrugs (or antibiotics) at tumors, thereby very much sparing normal host tissues. As proof of concept, we attached Dox to the scintillator crystal via a photocleavable linker using streptavidin and were able to obtain a stepwise release of Doc with escalating doses of irradiation using 1.1 MeV gamma rays.

The effectiveness of the nanoscintillator synthesis was determined in two ways. First, using electron microscopy it was demonstrated that particle shape and size, (i.e., 50-100 nm diameter and spherical) were consistent with shape and size criteria. Second, without wishing to be bound by theory, it is believed that the capacity for robust photon emission at the desired wavelength range of 350-470 nm with radiation exposure is acritical criterion of success. This was measured as the photons per MeV ranged from zero to 74,000. Indeed, the YAG-Pr crystals had the highest integrated emission between 350-370 nm ($4.5 \times 10^8$ photons). This wavelength range is useful to break the photosensitive linker (i.e., photocleavable linker) attaching a chemical agent moiety (e.g., doxorubicin therapeutic) to the nanocrystal scintillator. Again without wishing to be bound by theory, it is believed that scintillator wavelengths longer than about 365 nm may not be energetic enough to break the linker, but could additionally interact with the chemical agent moiety. Moreover, wavelengths shorter than about 365 may damage biologcial molecules and the chemical agent.

SUMMARY

We investigated a variety of potential scintillator elements and combinations for efficiency with low doses of radiation. We explored methods of synthesizing the best candidate compositions and the most efficient crystals, and identified the most effective method. We systematically varied synthesis conditions, the percentage of doped, the time of combustion, specialized heating, and the time of ultrasonication to attain the most efficient scintillator crystals. We determined optimum conditions for a sophisticated and successful synthetic regime. We showed that our crystals when irradiated with x-rays robustly emit light of a wavelength that will break a UV photosensitive linker. These crystals which are non-toxic, have a composition which allow coating and attaching of a photocleavable linker with drug. We showed that low energy X-rays, in the KeV range, will cause scintillator nanocrystals to scintillate such that the emitted photons can break the photocleavable linker and release a chemical agent moiety.

VI. Embodiments

Further embodiments include the Embodiments 1-38 following.

Embodiment 1

A composition comprising a scintillator nanocrystal linked to a chemical agent moiety through a scintillator-activated photocleavable linker.

Embodiment 2

The composition of embodiment 1, wherein said scintillator nanocrystal comprises a plurality of scintillator activators dispersed within a host crystal lattice.

Embodiment 3

The composition of embodiment 2, wherein said plurality of scintillator activators are cesium, europium or praseodymium.

Embodiment 4

The composition of embodiment 2, wherein said plurality of scintillator activators are cesium or praseodymium.

Embodiment 5

The composition of embodiment 2, wherein said plurality of scintillator activators are praseodymium.

Embodiment 6

The composition of one of embodiments 1 to 5, wherein said host crystal lattice is a chloride host crystal lattice, bromide host crystal lattice, oxide host crystal lattice, iodide host crystal lattice or silicate host crystal lattice.

Embodiment 7

The composition of embodiment 6, wherein said host crystal lattice is a lanthium bromide host crystal lattice.

Embodiment 8

The composition of embodiment 6, wherein said host crystal lattice is an oxide host crystal lattice or silicate host crystal lattice.

Embodiment 9

The composition of one of embodiments 1 to 5, wherein said host crystal lattice is a garnet host crystal lattice.

Embodiment 10

The composition of one of embodiments 1 to 5 or 9, wherein said host crystal lattice is an yttrium aluminum oxide host crystal lattice or gadolinium/yttrium aluminum oxide or a yttrium gallium/aluminum oxide host crystal lattice.

Embodiment 11

The composition of embodiment 1, wherein said scintillator nanocrystal has the formula $(Y_{1-x}Pr_x)_3Al_5O_{12}$, wherein x is 0.0075, 0.01, 0.0125, 0.015 or 0.0175.

Embodiment 12

The composition of one of embodiments 1 to 11, wherein said scintillator nanocrystal has a diameter from 25 nm to 300 nm.

Embodiment 13

The composition of one of embodiments 1 to 11, wherein said scintillator nanocrystal has a diameter from 50 nm to 250 nm.

Embodiment 14

The composition of one of embodiments 1 to 11, wherein said scintillator nanocrystal has a diameter from 50 nm to 200 nm.

Embodiment 15

The composition of one of embodiments 1 to 11, wherein said scintillator nanocrystal has a diameter from 50 nm to 150 nm.

Embodiment 16

The composition of one of embodiments 1 to 11, wherein said scintillator nanocrystal has a diameter from 50 nm to 100 nm.

Embodiment 17

The composition of one of embodiments 1 to 11, wherein said scintillator nanocrystal has a diameter of less than about 200 nm.

Embodiment 18

The composition of one of embodiments 1 to 17, wherein said scintillator nanocrystal emits photon emission peaks within 300 nm to 470 nm.

Embodiment 19

The composition of one of embodiments 1 to 17, wherein said scintillator nanocrystal emits photon emission peaks within 350 nm to 470 nm.

Embodiment 20

The composition of one of embodiments 1 to 17, wherein said scintillator nanocrystal emits photon emission peaks within 350 nm to 400 nm.

Embodiment 21

The composition of one of embodiments 1 to 17, wherein said scintillator nanocrystal emits photon emission peaks within 350 nm to 370 nm.

Embodiment 22

The composition of one of embodiments 1 to 21, wherein said scintillator-activated photocleavable linker cleaves and releases said chemical agent upon absorbing photons from 100 nm to 600 nm.

Embodiment 23

The composition of one of embodiments 1 to 21, wherein said scintillator-activated photocleavable linker cleaves and releases said chemical agent upon absorbing photons from 350 nm to 400 nm.

Embodiment 24

The composition of one of embodiments 1 to 21, wherein said scintillator-activated photocleavable linker cleaves and releases said chemical agent upon absorbing photons from 350 nm to 370 nm.

Embodiment 25

The composition of one of embodiments 1 to 24, wherein said scintillator-activated photocleavable linker is covalently attached to said chemical agent moiety and a surface of the scintillator nanocrystal.

Embodiment 26

The composition of embodiment 25, wherein said surface is a lipid bilayer surface or a silinated surface.

Embodiment 27

The composition of embodiment 25, wherein said surface is a silinated surface.

Embodiment 28

The composition of one of embodiments 1 to 27, wherein said scintillator-activated photocleavable linker has the formula:

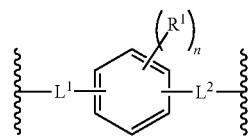

wherein, $L^1$ and $L^2$ are independently bond, —C(O)—, —C(O)O—, —O—, —S—, —NH—, —C(O)NH—, —NHC(O)—, —S(O)$_2$—, —S(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^1$ is independently halogen, —N$_3$, —CF$_3$, —CCl$_3$, —CBr$_3$, —CI$_3$, —CN, —COR$^2$, —OR$^2$, —NR$^2$R$^3$, —C(O)OR$^2$, —C(O)NR$^2$R$^3$, —NO$_2$, —SR$^2$, —S(O)$_{n1}$R$^2$, —S(O)$_{n1}$OR$^2$, —S(O)$_{n1}$NR$^2$R$^3$, —NHNR$^2$R$^3$, —ONR$^2$R$^3$, —NHC(O)NHNR$^2$R$^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ and $R^3$ are independently hydrogen, halogen, —N$_3$, —CF$_3$, —CCl$_3$, —CBr$_3$, —CI$_3$, —CN, —COH, —OH, —NH$_2$, —C(O)OH, —C(O)NH$_2$, —NO$_2$, —SH, —S(O)$_{n1}$H, —S(O)$_{n2}$OH, —S(O)$_{n2}$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n is an integer from 0 to 4; n1 and n2 are independently 1 or 2.

Embodiment 29

The composition of embodiment 28, wherein said scintillator-activated photocleavable linker has the formula:

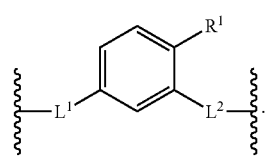

Embodiment 30

The composition of embodiment 28 or 29, wherein $R^1$ is —$NO_2$.

Embodiment 31

The composition of one of embodiments 28 to 30, wherein $L^2$ is —$(CH2)_{n3}$—O—C(O)—, wherein n3 is an integer from 0 to 5.

Embodiment 32

The composition of embodiment 32, wherein n3 is 1.

Embodiment 33

The composition of one of embodiments 28 to 32, wherein $L^2$ is bound to the chemical agent moiety.

Embodiment 34

The composition of one of embodiments 1 to 33, wherein the chemical agent moiety is covalently bound to said scintillator-activated photocleavable linker through an amine group on said scintillator-activated photocleavable linker thereby forming an —NH-connecting moiety.

Embodiment 35

The composition of one of embodiments 1 to 34, wherein said chemical agent moiety is a drug moiety, hormone moiety, a metal moiety, a radioprotective moiety, a cement moiety, a nucleotide triphosphate moiety, a protein moiety, a polysaccharide moiety, a neurotransmitter moiety, an enzyme moiety, a tissue factor moiety or a detectable moiety.

Embodiment 36

The composition of embodiment 35, wherein said drug moiety is an anticancer drug moiety or antibiotic drug moiety.

Embodiment 37

A method of delivering a chemical agent moiety to a target site, said method comprising: (i) providing the composition of one of embodiments 1 to 36 to a location at or near a target site, and (ii) cleaving said chemical agent from the remainder of said compound by exposing said composition to radiation thereby delivering said chemical agent to said target site.

Embodiment 38

A method of delivering a chemical agent moiety to a subject, said method comprising: (i) administering the composition of one of embodiments 1 to 36 to said subject, and (ii) cleaving said chemical agent from the remainder of said compound by exposing said composition to radiation thereby delivering said chemical agent to said subject.

Embodiment 39

The method of embodiment 38, wherein said subject is a cancer patient and said chemical agent moiety is an anticancer drug agent, and wherein said composition is administered to said subject in a therapeutically effective amount.

What is claimed is:

1. A composition, comprising:
   (i) a scintillator nanocrystal comprising $(Y_{1-x}Pr_x)_3Al_5O_{12}$, where x is 0.01;
   (ii) a chemical agent moiety comprising doxorubicin; and
   (iii) a scintillator nanocrystal-activated photocleavable linker comprising:

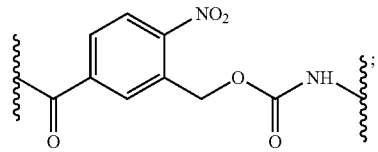 [SMILES: *NC(=O)OCc1cc(C(*)=O)ccc1[N+](=O)[O-]]

wherein said linker operably links said scintillator nanocrystal and said chemical agent moiety.

2. The composition of claim 1, wherein said scintillator nanocrystal comprises a host crystal lattice.

3. The composition of claim 1, wherein said scintillator nanocrystal has a diameter from 25 nm to 300 nm.

4. The composition of claim 1, wherein said composition downconverts incident energy to emission energy that is less than said incident energy; wherein said incident energy comprises energy that is in the X-ray range, the gamma-ray range, or a combination thereof; and wherein said emission energy comprises energy that is in the UV range.

5. The composition of claim 1, wherein said scintillator nanocrystal emits photon emission peaks within 300 nm to 470 nm.

6. The composition of claim 1, wherein said scintillator-activated photocleavable linker cleaves and releases said chemical agent moiety upon absorbing photons from 100 nm to 600 nm.

7. The composition of claim 1, wherein said scintillator-activated photocleavable linker is covalently attached to said chemical agent moiety and a surface of said scintillator nanocrystal.

8. The composition of claim 7, wherein said surface is a lipid bilayer surface.

9. The composition of claim 7, wherein said surface is a silinated surface.

10. The composition of claim 1, wherein said composition can be used to treat tumors, deep tumors, or a combination thereof.

11. The composition of claim 1, wherein said composition can be used to treat an infection.

12. The composition of claim 1, wherein said composition is in a powdered form.

13. The composition of claim 1, wherein said composition is in solid form or suspended in a liquid.

14. A composition comprising:
    (i) a scintillator nanocrystal comprising $(Y_{1-x}Pr_x)_3Al_5O_{12}$, where x is 0.0075, 0.01, 0.0125, 0.015, or 0.0175;
    (ii) a chemical agent moiety comprising an anti-cancer drug moiety; and
    (iii) a scintillator nanocrystal-activated photocleavable linker comprising:

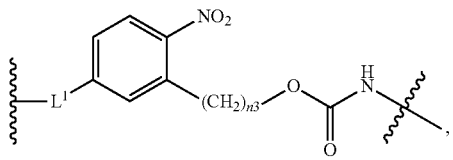 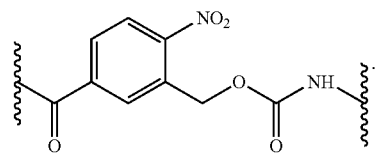

wherein n3 is an integer from 0 to 5; and $L^1$ is bond, —C(O)—, —C(O)O—, —O—, —S—, —NH—, —C(O)NH—, —NHC(O)—, —S(O)$_2$-, —S(O)NH—, substituted or unsubstituted alkylene, substituted or unsubstituted heteroalkylene, unsubstituted cycloalkylene, substituted or unsubstituted heterocycloalkylene, substituted or unsubstituted arylene, or substituted or unsubstituted heteroarylene;

wherein said linker operably links said scintillator nanocrystal and said chemical agent moiety.

15. The composition of claim 14, wherein the anti-cancer drug moiety is doxorubicin.

16. The composition of claim 14, wherein x is 0.01.

17. The composition of claim 14, wherein the scintillator nanocrystal-activated photocleavable linker comprises:

18. The composition of claim 1, wherein the scintillator nanocrystal produces two photon emission peaks between 300 nm and 400 nm when exposed to an X-ray of 50 keV.

19. The composition of claim 1, wherein the scintillator nanocrystal produces a photon emission peak between 350 nm and 400 nm when exposed to an X-ray of 50 keV.

20. The composition of claim 14, wherein the scintillator nanocrystal produces two photon emission peaks between 300 nm and 400 nm when exposed to an X-ray of 50 keV.

21. The composition of claim 1, wherein the scintillator nanocrystal produces a photon emission peak between 350 nm and 400 nm when exposed to an X-ray of 50 keV.

* * * * *

UNITED STATES PATENT AND TRADEMARK OFFICE
CERTIFICATE OF CORRECTION

Page 1 of 1

PATENT NO. : 10,864,272 B2
APPLICATION NO. : 15/052526
DATED : December 15, 2020
INVENTOR(S) : Milan T. Makale et al.

It is certified that error appears in the above-identified patent and that said Letters Patent is hereby corrected as shown below:

In the Specification

At Column 1, after Line 13 and before "Background of the Invention" insert the following:
--STATEMENT AS TO RIGHTS TO INVENTIONS MADE UNDER FEDERALLY SPONSORED RESEARCH AND DEVELOPMENT
This invention was made with Government support under grant no. CA187528 awarded by the National Institutes of Health. The Government has certain rights in this invention.--

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*